(12) United States Patent
　　Batty et al.

(10) Patent No.: US 12,616,468 B2
(45) Date of Patent: May 5, 2026

(54) ARTICULATION SUBSYSTEMS FOR ROBOTIC STAPLING AND CUTTING SYSTEMS

(71) Applicant: CILAG GMBH INTERNATIONAL, Zug (CH)

(72) Inventors: Christopher Batty, Cincinnati, OH (US); Robert Jason Simms, Cincinnati, OH (US); Jonathan Von Stein, Cincinnati, OH (US); Maria Lupp, Cincinnati, OH (US); Jason Bryant, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/775,632

(22) Filed: Jul. 17, 2024

(65) Prior Publication Data

US 2025/0025159 A1　　Jan. 23, 2025

Related U.S. Application Data

(60) Provisional application No. 63/634,201, filed on Apr. 15, 2024, provisional application No. 63/634,171, (Continued)

(51) Int. Cl.
　　*A61B 17/072*　　　(2006.01)
　　*A61B 17/00*　　　(2006.01)
　　(Continued)

(52) U.S. Cl.
　　CPC ........ *A61B 17/072* (2013.01); *A61B 17/0643* (2013.01); *A61B 17/07207* (2013.01);
　　(Continued)

(58) Field of Classification Search
　　CPC ... A61B 17/072; A61B 34/30; A61B 17/0643; A61B 17/07207; A61B 17/07257; A61B 17/07271; A61B 17/07285
　　See application file for complete search history.

(56) References Cited

U.S. PATENT DOCUMENTS 8,292,150 B2　10/2012　Bryant
8,800,838 B2　8/2014　Shelton, IV et al.
　　(Continued)

FOREIGN PATENT DOCUMENTS

EP　　　2768418 B1　　7/2017
EP　　　2811932 B1　　6/2019
　　(Continued)

OTHER PUBLICATIONS

International Search Report and Written Opinion for Related PCT Appl. No. PCT/IB2024/056986, Dated Oct. 24, 2024.

*Primary Examiner* — Michelle Lopez
(74) *Attorney, Agent, or Firm* — Troutman Pepper Locke LLP

(57) ABSTRACT

The present disclosure relates to systems, devices, and subsystems for robotic surgeries. The surgical instrument is a robotic attachment that includes an articulation subsystem comprising a rotatable shaft, a distal channel retainer coupled to an end effector that is pivotable about an articulation pivot point, an articulation bushing slidable between a proximal position and a distal position, an articulation rod extending distally from the articulation bushing and coupled at a distal end to the distal channel retainer; and a rack movable with respect to the longitudinal axis of the rotatable shaft. Movement of the rack with respect to the longitudinal axis imparts an axial force onto the articulation bushing moving the articulation bushing between the proximal position and the distal position. Movement of the articulation bushing between the distal position and the proximal posi- (Continued)

tion actuates the articulation rod causing the distal channel retainer to pivot about the articulation pivot point.

29 Claims, 42 Drawing Sheets

Related U.S. Application Data filed on Apr. 15, 2024, provisional application No. 63/515,001, filed on Jul. 21, 2023, provisional application No. 63/514,972, filed on Jul. 21, 2023.

(51) Int. Cl.
| *A61B 17/064* | (2006.01) |
| *A61B 17/068* | (2006.01) |
| *A61B 17/29* | (2006.01) |
| *A61B 34/30* | (2016.01) |

(52) U.S. Cl.
CPC .... *A61B 34/30* (2016.02); *A61B 2017/00017* (2013.01); *A61B 2017/00367* (2013.01); *A61B 2017/00398* (2013.01); *A61B 2017/00411* (2013.01); *A61B 2017/00477* (2013.01); *A61B 2017/00831* (2013.01); *A61B 2017/00862* (2013.01); *A61B 17/068* (2013.01); *A61B 17/0686* (2013.01); *A61B 2017/07257* (2013.01); *A61B 2017/07271* (2013.01); *A61B 2017/07285* (2013.01); *A61B 2017/2903* (2013.01); *A61B 2217/007* (2013.01)

(56) References Cited

U.S. PATENT DOCUMENTS

| 9,232,979 | B2* | 1/2016 | Parihar ................. A61B 18/18 |
| 10,085,748 | B2 | 10/2018 | Morgan et al. |
| 10,143,524 | B2 | 12/2018 | Koch |
| 10,251,716 | B2 | 4/2019 | Overmyer |
| 10,307,215 | B2 | 6/2019 | Swayze |
| 10,327,854 | B2 | 6/2019 | Overmyer |
| 10,376,276 | B2 | 8/2019 | Overmyer |
| 10,433,920 | B2 | 10/2019 | Overmyer |
| 10,542,982 | B2 | 1/2020 | Beckman |
| 10,675,025 | B2 | 6/2020 | Swayze |
| 10,702,349 | B2 | 7/2020 | Overmyer |
| 10,918,385 | B2 | 2/2021 | Overmyer |
| 10,987,177 | B2 | 4/2021 | Overmyer et al. |
| 11,033,344 | B2 | 6/2021 | Overmyer |
| 11,191,539 | B2 | 12/2021 | Overmyer |
| 11,191,543 | B2 | 12/2021 | Overmyer |
| 11,191,560 | B2 | 12/2021 | Overmyer |
| 11,419,605 | B2 | 8/2022 | Denzinger |
| 11,419,606 | B2 | 8/2022 | Overmyer |
| 11,439,474 | B2 | 9/2022 | Kallenberger |
| 11,446,098 | B2 | 9/2022 | Swayze |
| 11,471,228 | B2 | 10/2022 | Overmyer |
| 11,547,494 | B2 | 1/2023 | Swayze |
| 11,559,366 | B2 | 1/2023 | Overmyer |
| 11,622,825 | B2 | 4/2023 | Overmyer |
| 11,813,032 | B2 | 11/2023 | Overmyer |
| 11,813,746 | B2 | 11/2023 | Overmyer |
| 11,864,954 | B2 | 1/2024 | Overmyer |
| 12,023,116 | B2 | 7/2024 | Overmyer |
| 12,070,287 | B2 | 8/2024 | Overmyer |
| 2003/0130677 | A1 | 7/2003 | Whitman et al. |
| 2007/0023476 | A1 | 2/2007 | Whitman et al. |
| 2009/0114699 | A1* | 5/2009 | Viola .............. A61B 17/07207 227/19 |
| 2014/0263541 | A1 | 9/2014 | Leimbach et al. |
| 2014/0303645 | A1 | 10/2014 | Morgan et al. |
| 2016/0067001 | A1 | 3/2016 | Parihar et al. |
| 2016/0174976 | A1* | 6/2016 | Morgan .............. A61B 17/072 227/175.1 |
| 2016/0174978 | A1 | 6/2016 | Overmyer et al. |
| 2016/0213438 | A1 | 7/2016 | Jogasaki et al. |
| 2019/0021752 | A1 | 1/2019 | Boudreaux et al. |
| 2019/0105117 | A1 | 4/2019 | Brisson et al. |
| 2019/0183491 | A1 | 6/2019 | Shelton, IV et al. |
| 2019/0183504 | A1 | 6/2019 | Shelton, IV et al. |
| 2019/0183592 | A1 | 6/2019 | Shelton, IV et al. |
| 2019/0183597 | A1 | 6/2019 | Shelton, IV et al. |
| 2020/0093489 | A1 | 3/2020 | Parihar et al. |
| 2020/0330120 | A1 | 10/2020 | Koch, Jr. et al. |
| 2020/0375596 | A1 | 12/2020 | Corsetto |
| 2021/0059664 | A1* | 3/2021 | Hensel ................ A61B 17/072 |
| 2021/0059773 | A1* | 3/2021 | Overmyer ............. A61B 34/30 |
| 2021/0059777 | A1 | 3/2021 | Overmyer et al. |
| 2021/0346050 | A1 | 11/2021 | Boudreaux et al. |
| 2022/0105638 | A1* | 4/2022 | Zhang ..................... B25J 13/06 |
| 2022/0105639 | A1* | 4/2022 | Zhang ................... B25J 9/1689 |
| 2022/0125538 | A1 | 4/2022 | Overmyer et al. |
| 2022/0192707 | A1 | 6/2022 | Barakat et al. |
| 2022/0346897 | A1 | 11/2022 | Black et al. |
| 2022/0409310 | A1 | 12/2022 | Overmyer et al. |
| 2023/0001579 | A1 | 1/2023 | Overmyer |
| 2023/0181275 | A1 | 6/2023 | Overmyer |
| 2023/0338051 | A1 | 10/2023 | Robert, Jr. |
| 2023/0355338 | A1 | 11/2023 | Overmyer |
| 2024/0081191 | A1 | 3/2024 | Beckman |

FOREIGN PATENT DOCUMENTS

| EP | 2866697 | B1 | 12/2021 |
| KR | 20150100137 | A | 9/2015 |
| WO | 2020212875 | A1 | 10/2020 |
| WO | 2021038360 | A2 | 3/2021 |
| WO | 2022144818 | A1 | 7/2022 |
| WO | 2023225866 | A1 | 11/2023 |

* cited by examiner

ARTICULATION SUBSYSTEMS FOR ROBOTIC STAPLING AND CUTTING SYSTEMS

CROSS-REFERENCE TO RELATED APPLICATIONS

The present application claims the benefit of, and priority to, U.S. Provisional Application Ser. No. 63/514,972 filed on Jul. 21, 2023, U.S. Provisional Application Ser. No. 63/515,001 filed on Jul. 21, 2023, U.S. Provisional Application Ser. No. 63/634,201 filed on Apr. 15, 2024, and U.S. Provisional Application Ser. No. 63/634,171 filed on Apr. 15, 2024, the disclosures of which are expressly incorporated herein by reference.

FIELD OF INVENTION

The present disclosure generally relates to systems, devices, and subsystems for cutting and stapling tissue. More specifically, the present disclosure relates to systems, devices, and subsystems for attachments for robotic surgeries.

BACKGROUND

Stapling is a crucial aspect of many surgical procedures, such as gastrointestinal, thoracic, and gynecological surgeries. Robotic surgical systems have gained significant recognition in recent years due to their potential to enhance surgical precision and dexterity. However, the development of a dedicated surgical stapling instrument that integrates seamlessly into the surgical workflow of a multi-purpose robot remains an unmet need for many surgeons.

SUMMARY

It is an object of the present designs to provide devices and methods to meet the above-stated needs. The designs can be for systems, devices, and subsystems for stapling attachments for robotic surgeries. The attachments can have several subsystems that can be independently actuated to provide a specific action, such as closing of an end effector of the stapler, articulation of the end effector, rolling of the end effector, and firing of the staples within the end effector.

In one example, the surgical instrument described herein includes an articulation subsystem for a surgical instrument. The articulation subsystem comprises a rotatable shaft having a longitudinal axis and a distal channel retainer coupled to an end effector, the distal channel retainer being pivotable about an articulation pivot point. The articulation subsystem further comprises an articulation bushing slidable between a proximal position and a distal position along the longitudinal axis of the rotatable shaft and an articulation rod extending distally from the articulation bushing and coupled at a distal end to the distal channel retainer. The articulation subsystem further comprises a rack movable with respect to the longitudinal axis of the rotatable shaft, wherein movement of the rack with respect to the longitudinal axis imparts an axial force onto the articulation bushing moving the articulation bushing between the proximal position and the distal position. Furthermore, movement of the articulation bushing between the distal position and the proximal position actuates the articulation rod causing the distal channel retainer to pivot about the articulation pivot point.

The disclosed technology includes an articulation subsystem for a surgical instrument comprising a rotatable shaft having a longitudinal axis, an articulation rod extending along the longitudinal axis of the rotatable shaft and rotationally coupled to the rotatable shaft, and a first articulation bushing slidable from a first position to a second position along the longitudinal axis of the rotatable shaft. The first articulation bushing can be rotationally coupled to the rotatable shaft. The articulation subsystem can further include a first rack movable with respect to the longitudinal axis of the rotatable shaft with the first rack being rotationally independent of the rotatable shaft and the first articulation bushing. The articulation subsystem can further include a first rack gear engaged with the first rack. Rotation of the first rack gear can move the first rack with respect to the longitudinal axis and movement of the first rack with respect to the longitudinal axis can impart an axial force onto the first articulation bushing moving the first articulation bushing from the first position to the second position.

Other aspects of the present disclosure will become apparent upon reviewing the following detailed description in conjunction with the accompanying figures. Additional features or manufacturing and use steps can be included as would be appreciated and understood by a person of ordinary skill in the art.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation. It is expected that those of skill in the art can conceive of and combine elements from multiple figures to better suit the needs of the user.

FIG. 9 is a perspective view of the surgical instrument while

FIG. 19A is a perspective view of the components of the roll subsystem, and FIG. 19B is a top, cross-sectional view of the components of the roll subsystem, according to aspects of the present disclosure.

FIG. 19C shows an example of a shaft with two flat sections (or "flats"), FIG. 19D shows an example of a shaft with a keyway and a worm follower with a corresponding key feature, FIG. 19E shows an example of a shaft with a keyway and a worm follower with a corresponding key feature, and FIG. 19F shows an example of a shaft and a worm follower with corresponding steps, according to aspects of the present disclosure.

FIG. 19G is a side cross sectional view thereof, and FIG. 19H is cross sectional view from the direction indicated in 19G, according to aspects of the present disclosure.

FIG. 19I is a cross sectional view of the roll subsystem, according to aspects of the present disclosure.

DETAILED DESCRIPTION

Specific examples of the present invention are now described in detail with reference to the figures, where identical reference numbers indicate elements which are functionally similar or identical. The examples address many of the deficiencies associated with prior robotic attachment systems, for instance prior systems that did not provide integrated capabilities to close, articulate, roll, and fire, all with the actuation of their designated robotic outputs. The present surgical instrument includes a housing that contains the gearing and other components necessary to effect the close, articulate, roll, and fire features. In particular, the present disclosure provides a detailed discussion of the closure subsystem, articulation system, roll subsystem, and transection subsystem that are usable to close, articulate, roll, and fire an end effector of the device. Use of the term "fire" throughout this disclosure means to advance the distal portions of the transection subsystem distally. "Firing" the components shall be understood to mean cutting, stapling, or both.

Overview

Figure 1:
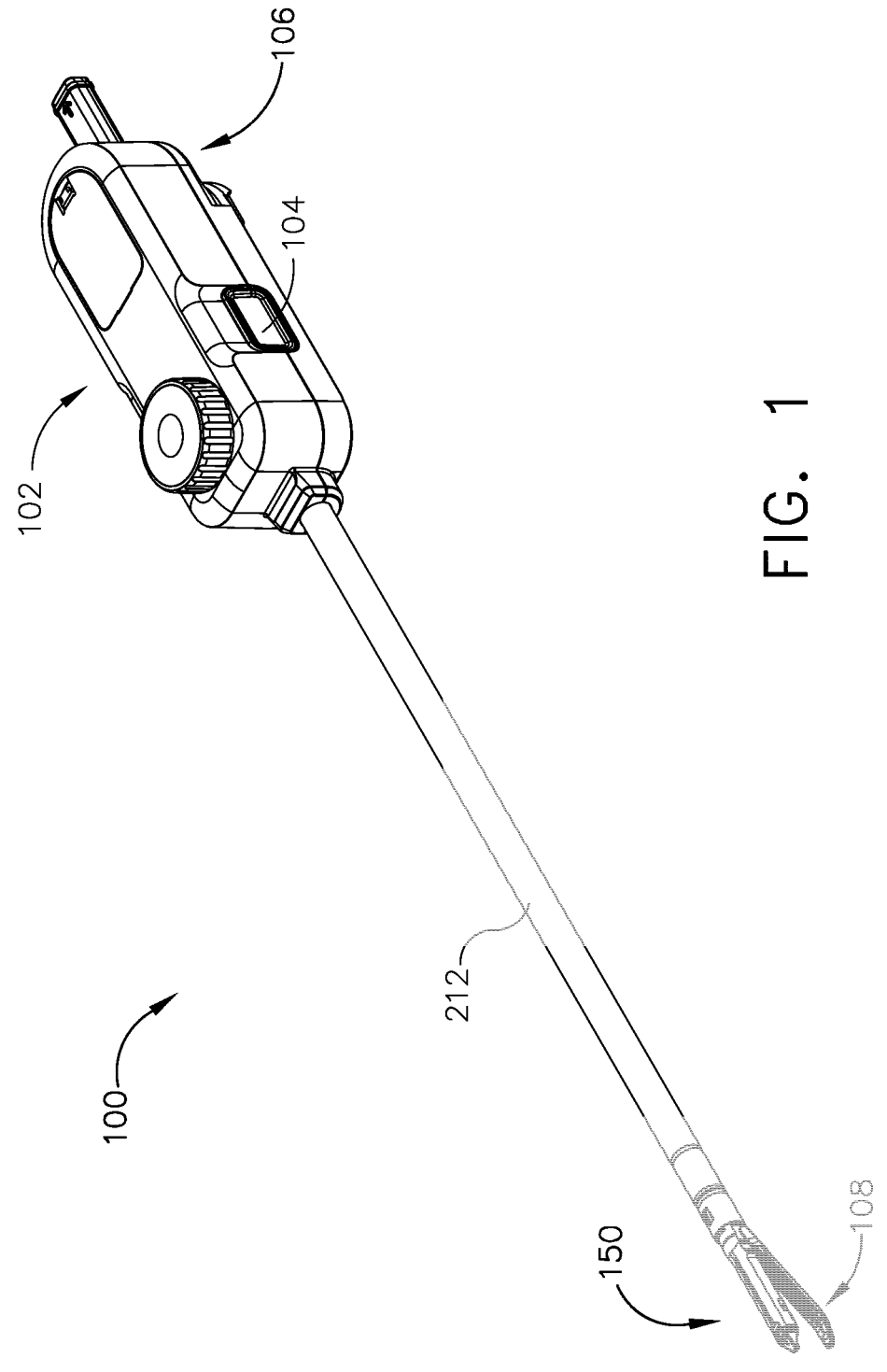
FIG. 1 shows a surgical instrument, according to aspects of the present disclosure.

Turning to the figures, FIG. 1 is a perspective view illustrating a surgical instrument 100, according to aspects of the present disclosure. A housing 102 of the surgical instrument 100 can be attachable to a robotic arm that includes a plurality of outputs, or rotatable disks, that can actuate pucks, or other disks, on the surgical instrument 100. The proximal end 106 of the surgical instrument 100 can be attached to a robotic arm and the distal end 108 of the surgical instrument 100 effects the transection and stapling of patient tissue. The proximal end 106 of the surgical instrument 100 includes a tail cover 114. The surgical instrument can include one or more release buttons 104 that allows the device to be detached from the robotic arm.

Figure 2A:
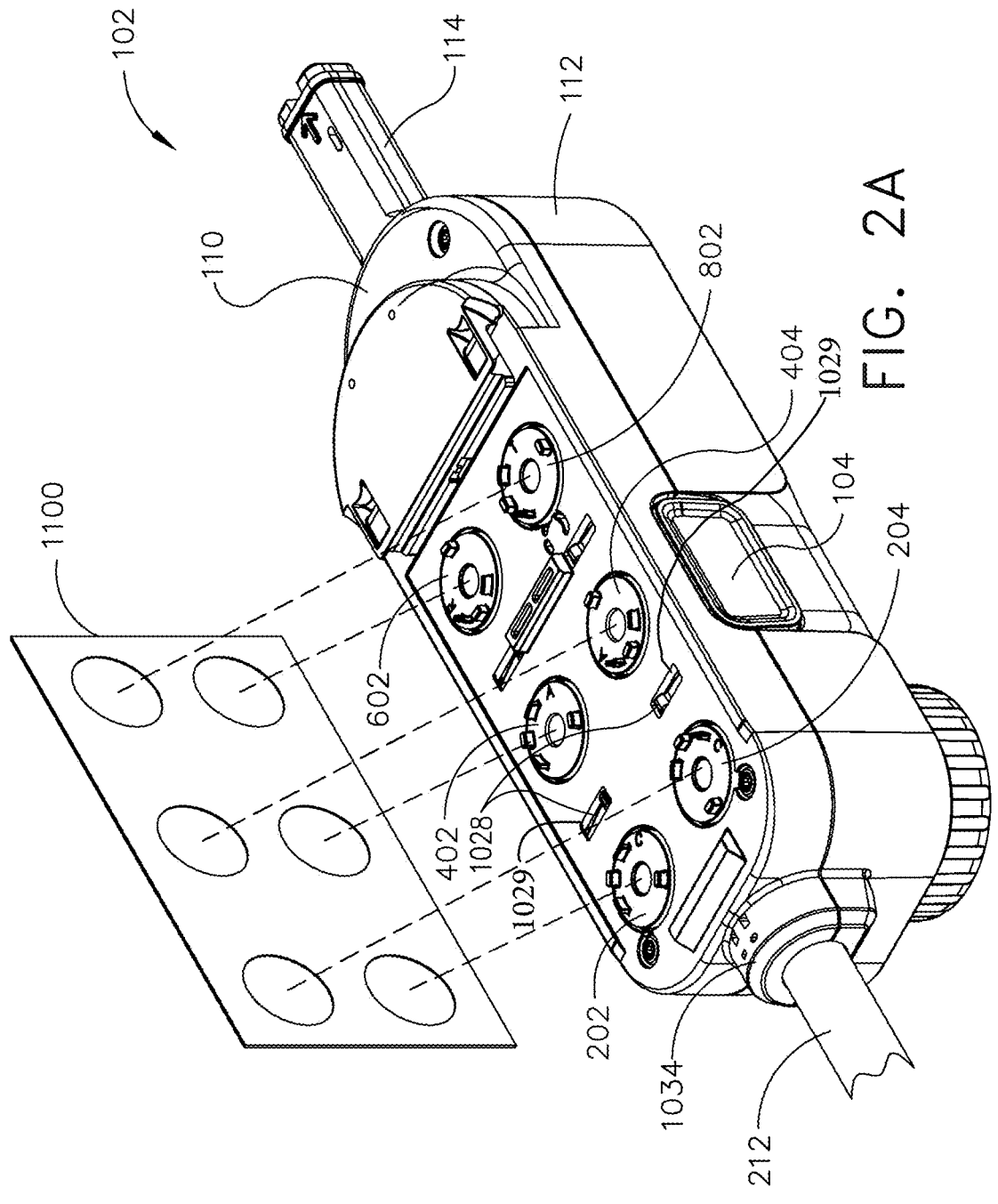
FIG. 2A shows a housing at a proximal end of a surgical instrument, according to aspects of the present disclosure.

FIG. 2A is a perspective view of the housing 102 as shown from the other side from what is shown in FIG. 1. The housing 102 can include a first portion 110 and a second portion 112. The housing 102 includes a series of pucks (e.g., first closure input puck 202, second closure input puck 204, first articulation input puck 402, second articulation input puck 404, roll input puck 602, and transection input puck 802). The pucks include features that enable them to engage with the rotating features of the robotic arm 1100 and a sterile adapter positioned between the surgical instrument 100 and the robotic arm 1100, such that rotation of the pucks can actuate the gears and other components of the closure subsystem 200, articulation subsystem 400, roll subsystem 600, and transection subsystem 800 described herein.

Figure 3A:
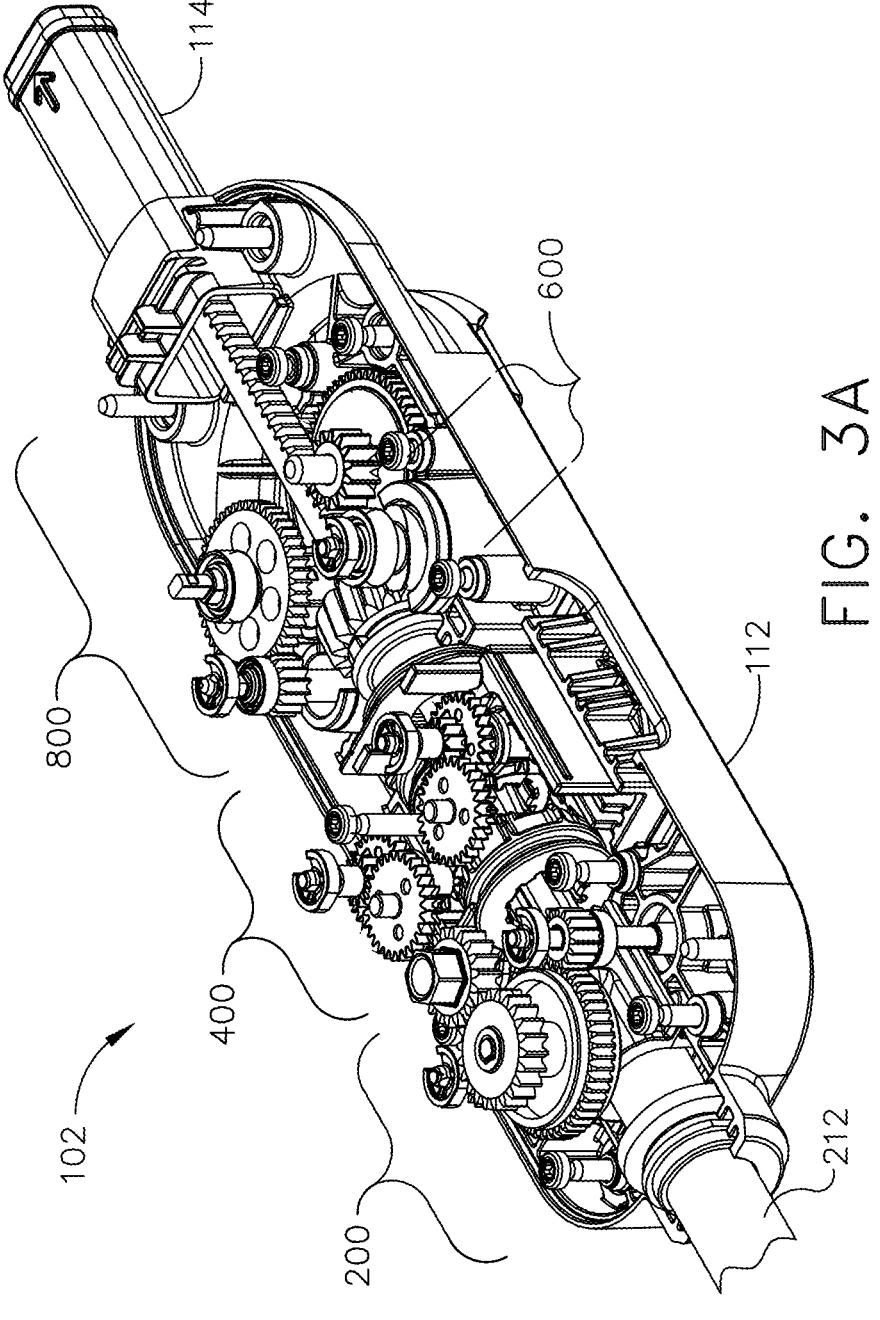
FIGS. 3A and 3B show internal components of a housing at a proximal end of a surgical instrument, according to aspects of the present disclosure.
Figure 3B:
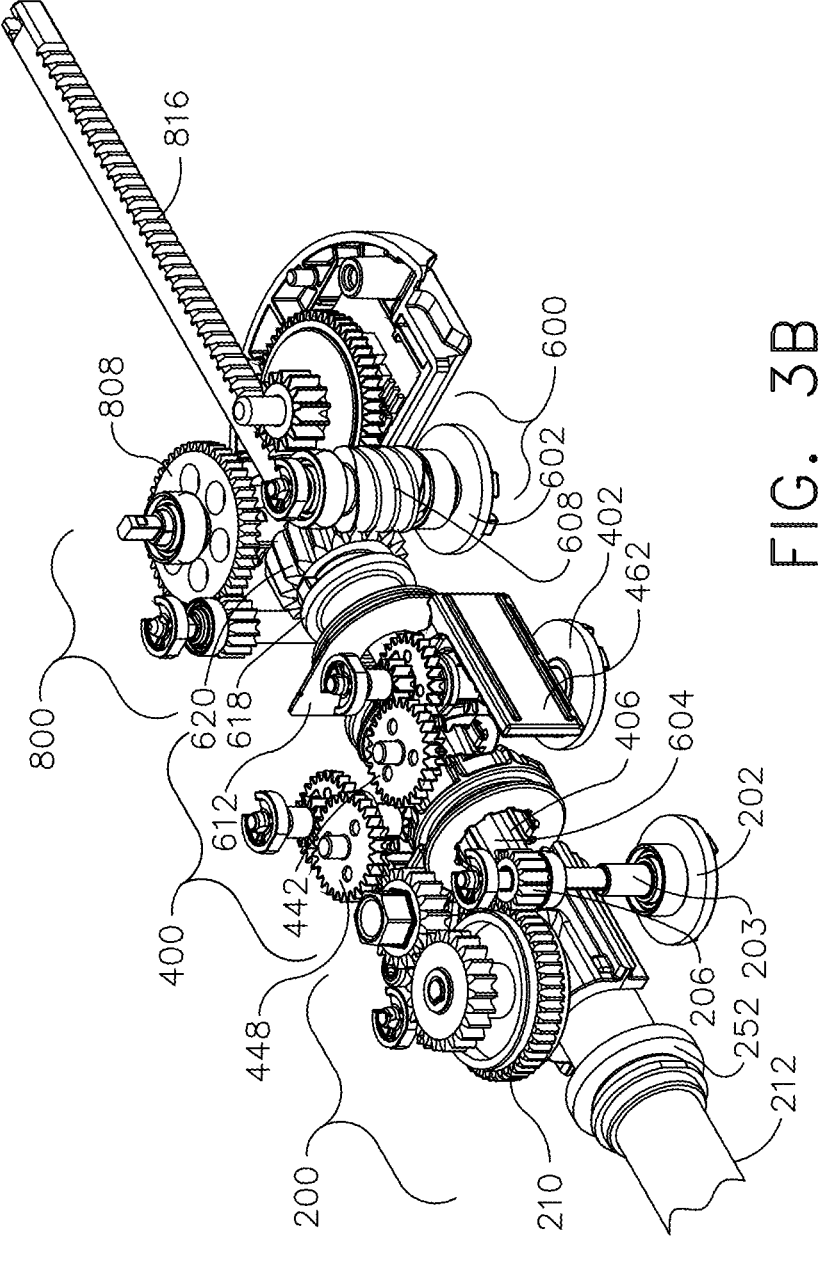

FIGS. 3A and 3B show internal components of the housing 102 at the proximal end 106 of the surgical instrument 100. As shown in FIG. 3A, housing 102 includes components of the closure subsystem 200, articulation subsystem 400, roll subsystem 600, and transection subsystem 800 described herein. As will be described in greater detail herein, the pucks (e.g., first closure input puck 202, second closure input puck 204, first articulation input puck 402, second articulation input puck 404, roll input puck 602, and transection input puck 802) can each be attached to components that extend through the housing 102 and rotationally engage respective components of the closure subsystem 200, articulation subsystem 400, roll subsystem 600, and transection subsystem 800. In this way, rotation of each individual puck causes the end effector to actuate (roll, close or open, articulate, fire staples, etc.) to enable physician to complete a surgery via a robotic system.

Figure 2B:
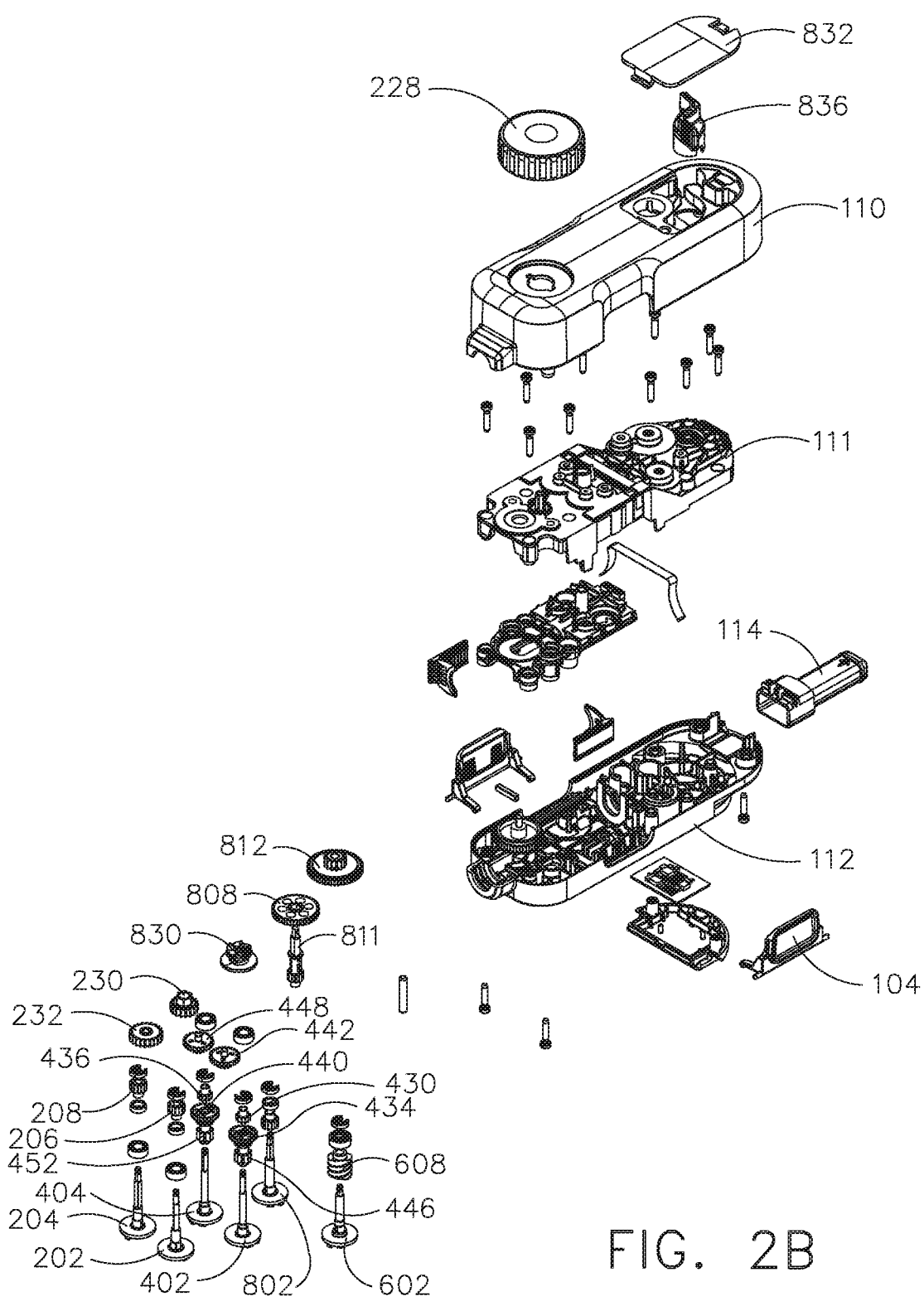
FIG. 2B is an exploded view of the components within a proximal end of a surgical instrument, according to aspects of the present disclosure.

FIG. 3B shows internal components of the surgical instrument 100 shown without an outer housing 102, according to aspects of the present disclosure. The closure subsystem 200 and the articulation subsystem 400 each utilize two different pucks (e.g., first closure input puck 202, second closure input puck 204, first articulation input puck 402, and second articulation input puck 404) for their respective actions, whereas the roll subsystem 600 and transection subsystem 800 each utilize only one puck (e.g., roll input puck 602 and transection input puck 802) for their respective actions. There are certain benefits to the closure subsystem 200 and the articulation subsystem 400 each utilizing two different pucks, including but not limited to providing additional force to increase the closure subsystem's 200 ability to compress tissue and adding input torque and reducing lash to increase responsiveness for articulation. FIG. 2B is an exploded view of the components within a proximal end 106 of the surgical instrument 100. As shown in FIG. 2B, the outer housing 102 can further include an intermediate housing 111 that can be disposed between the first portion 110 and the second portion 112 and help to provide support to the various components in the outer housing 102 as described further herein.

Figure 4:
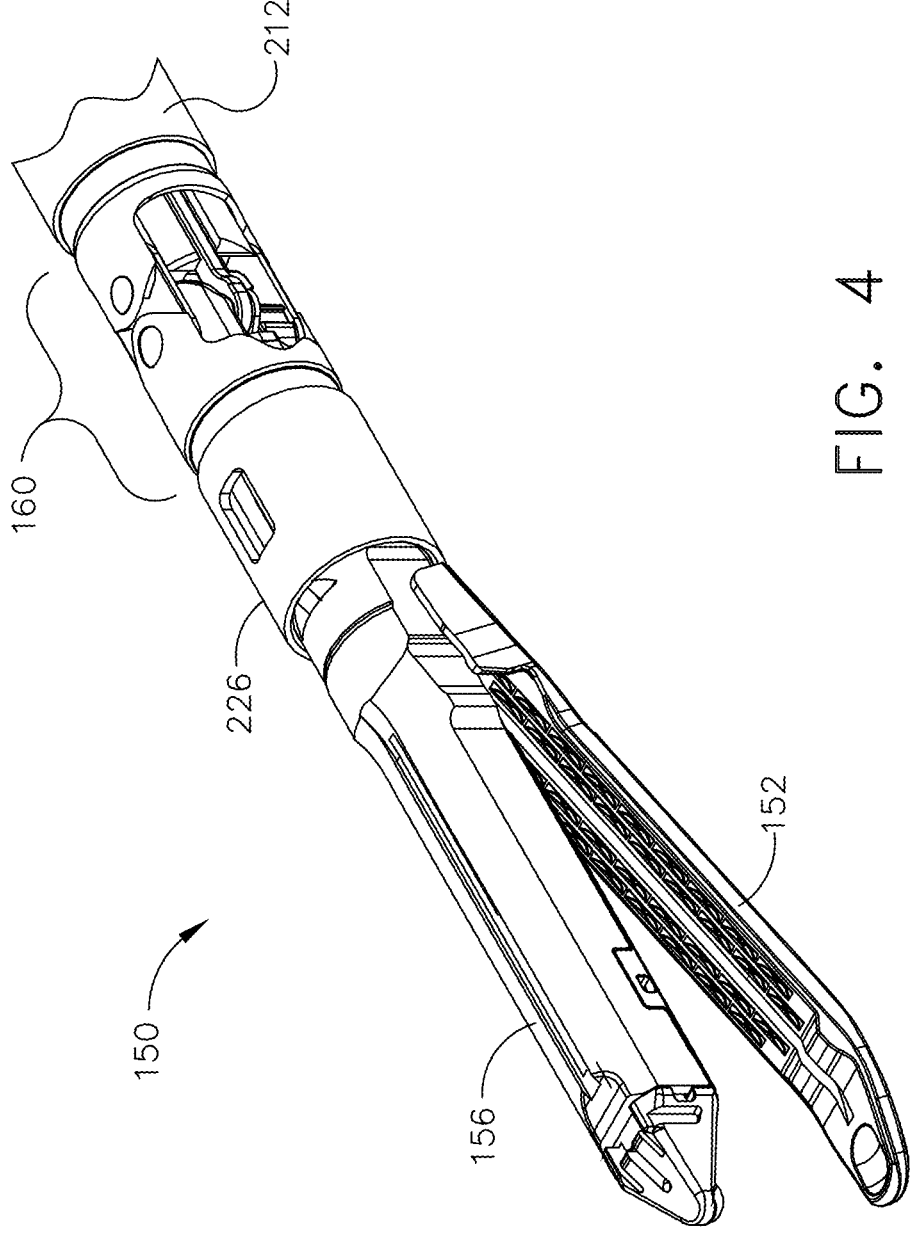
FIG. 4 shows a perspective view of an end effector of the surgical instrument, according to aspects of the present disclosure.

As shown in FIG. 4, the surgical instrument 100 includes an end effector 150 disposed at the distal end 108 of the surgical instrument 100. As shown, the end effector 150 includes an anvil 152 and a channel 156. As will be described in greater detail herein, the anvil 152 can be caused to move with respect to the channel 156 to open and close the end effector 150. Furthermore, as will be described in greater detail herein, the surgical instrument 100 includes a closure ring 226 and a closure tube 212 that can be actuated to cause the anvil 152 to open and close with respect to the channel 156. The anvil 152 can be opened by retracting the closure ring 226 from the anvil 152.

Figures 5A, 5B:
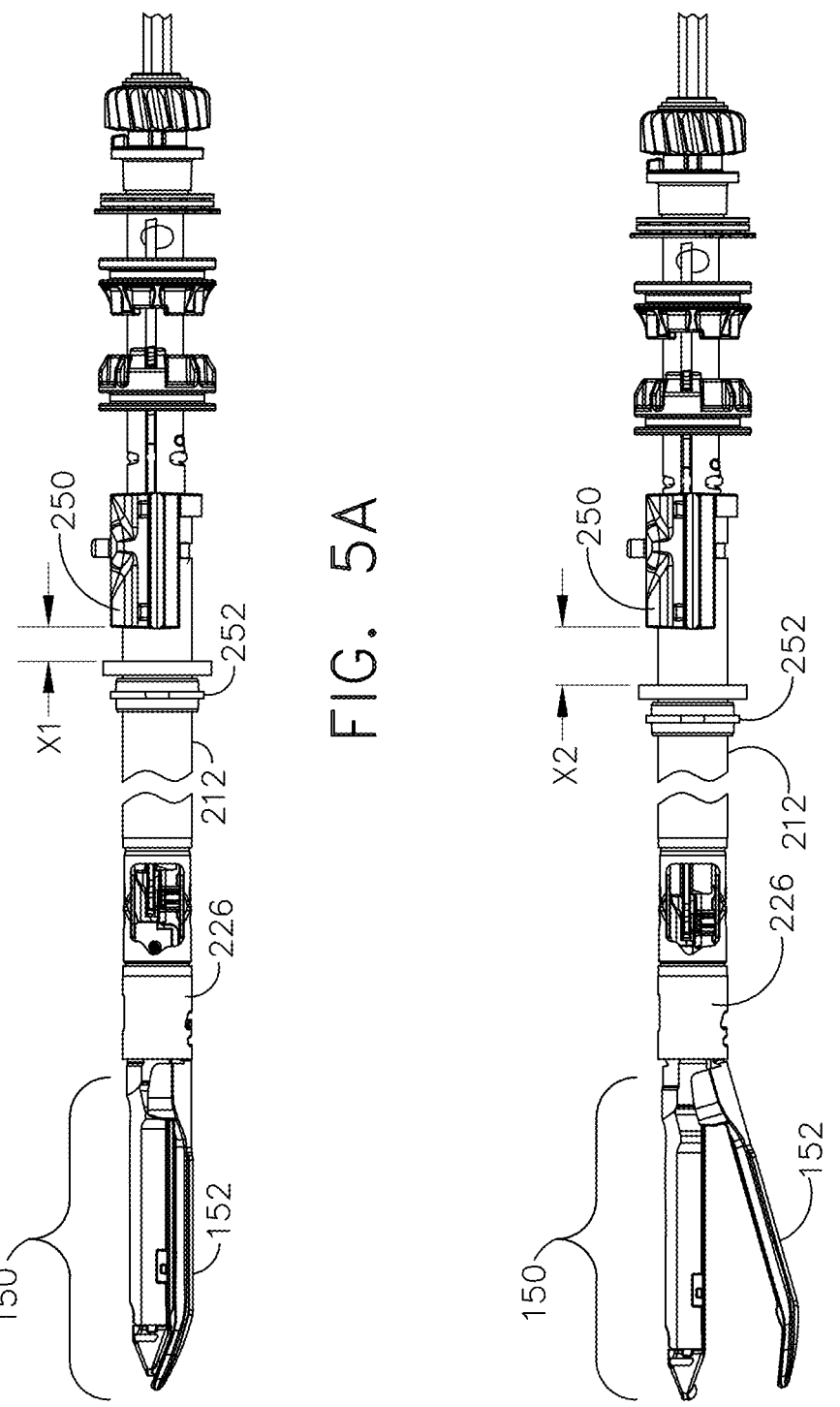
FIG. 5A shows a closure subsystem in a closed configuration, according to aspects of the present disclosure.
FIG. 5B shows a closure subsystem in an open configuration, according to aspects of the present disclosure.

FIG. 5A illustrates an end effector 150 in a closed configuration while FIG. 5B illustrates an end effector 150 in an open configuration. The anvil 152 of the end effector 150 can be opened and closed by operation of a closure ring 226 that is coupled to the anvil 152 and can be slid proximally and distally by the closure tube 212. As the closure ring 226 is slid distally the closure ring 226 causes the anvil 152 to close. As the closure ring 226 is slid proximally, the closure ring 226 causes the anvil 152 to open. The closure ring 226 can be caused to move between the opened and closed position by actuation of the closure tube 212. As the closure tube 212 is slid proximally and distally, the closure tube 212, which is engaged with the closure ring 226, causes the closure ring 226 to also slide proximally and distally, thereby opening and closing the anvil 152.

As shown in FIGS. 5A and 5B, the closure tube 212 can be actuated by movement of a closure yoke 250 between an open position in which the anvil 152 is opened and a closed position in which the anvil 152 is closed. The closure yoke 250 can slide axially in a proximal direction to open the anvil 152 and slide axially in a distal direction to cause the anvil 152 to close. In other words, when the closure yoke is in the open position, a distance X1 between the closure yoke 250 and a distal roll bushing 252 (which remains stationary) will be less than when the closure yoke 250 is in the closed position and a distance between the closure yoke 250 and the distal roll bushing 252 is X2. As will be described in greater detail herein, the closure yoke 250 can be transitioned between the open and closed positions by actuation of several gears.

Figure 6A:
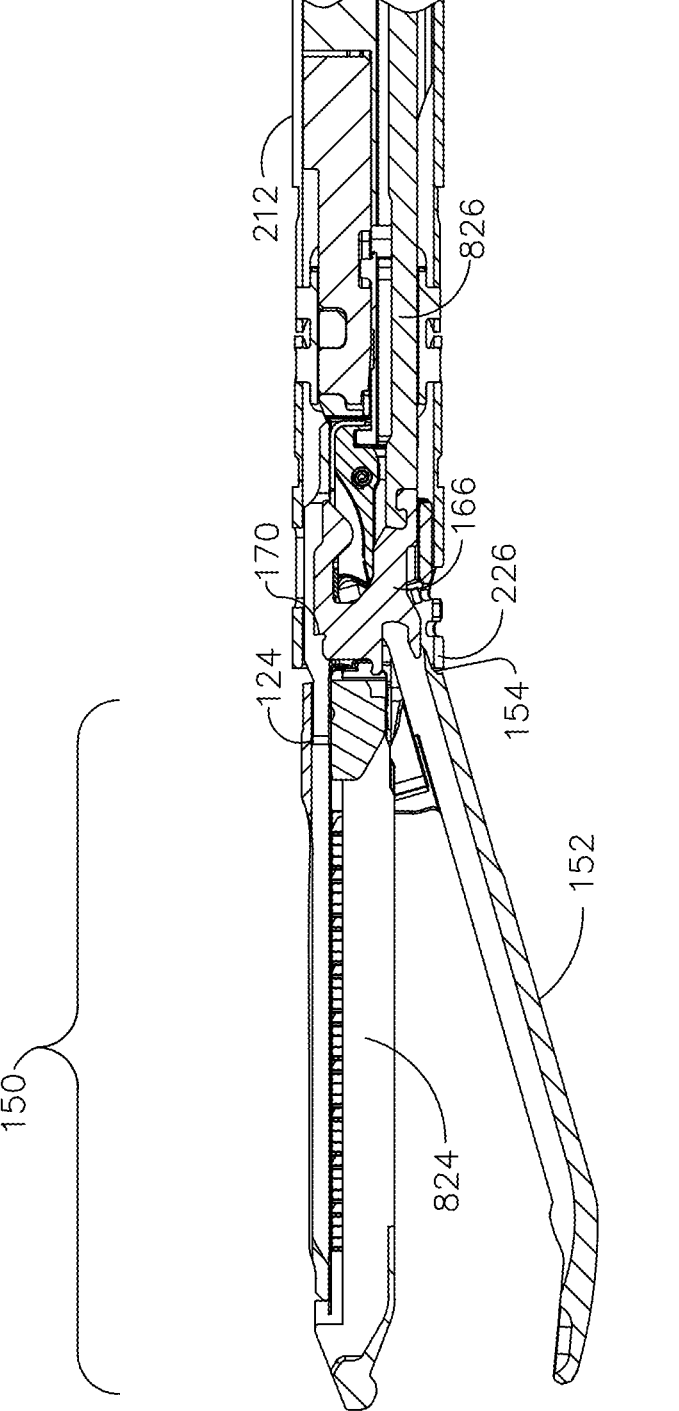
FIG. 6A shows a section view of the end effector and closure subsystem, according to aspects of the present disclosure.

FIG. 6A is a cross sectional view of the end effector 150 showing the end effector 150, the closure ring 226 and the closure tube 212. The closure ring 226 can be coupled to the anvil 152 such that the anvil 152 is caused to open when the closure ring 226 is slid proximally and caused to close when the closure ring 226 is slid distally. In this way, the closure subsystem 200 must be actuated between the opened and closed position to transition the anvil 152 between the open and closed position. In other words, it is not possible to open or close the anvil 152 without also actuating the other components of the closure subsystem 200.

Figure 6B:
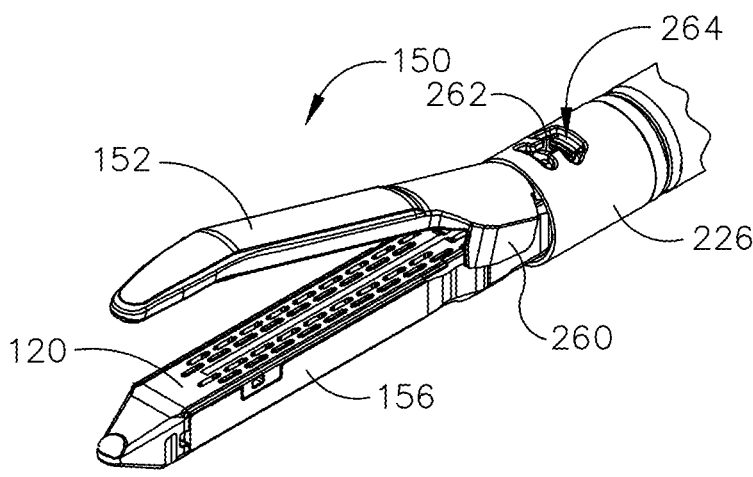
FIG. 6B is a perspective view of the end effector and closure system, according to aspects of the present disclosure.
Figure 6C:
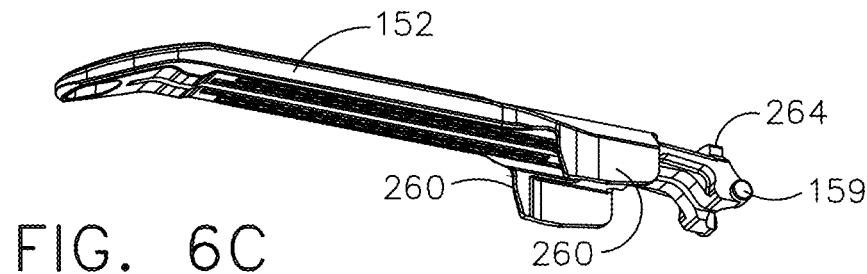
FIG. 6C is a perspective view of the anvil, according to aspects of the present disclosure.
Figure 6D:
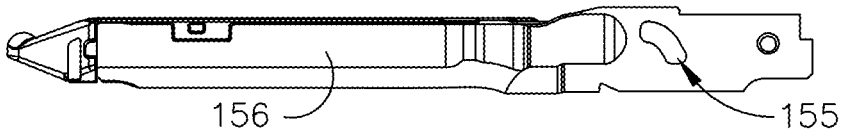
FIG. 6D is a perspective view of the channel, according to aspects of the present disclosure.

FIG. 6B is a perspective view of the end effector showing the anvil 152, the channel 156, a cartridge installed in the channel 120, and the closure ring 226. The anvil 152 includes flanges 260 that can extend outwardly at a proximal end of the anvil 152. As shown in FIG. 6C, the anvil 152 further includes an anvil tab 264 positioned at a proximal end of the anvil 152. The anvil tab 264 is configured to contact one or more closure ring tabs 262 that can extend inwardly from the closure ring 226 to cause the anvil 152 to open and close.

As shown in FIG. 6C, the anvil 152 includes one or more anvil pins 159 that can extend into an opening 155 in the channel 156. Opening 155 is an elongate slot in this example. It should therefore be understood that anvil pin 159 slides along opening 155 in addition to pivoting about its own axis within opening 155. This action may still be regarded as "pivoting" as defined herein, even though the pivot axis translates with anvil pin 159 along opening 155 and is not in a fixed position.

As closure ring 226 translates distally in response to advancement of closure tube 212, closure ring 226 translates relative to anvil 152 to engage anvil 152. Closure ring 226 engages anvil 152 to translate anvil 152 distally by contacting the anvil ramp 154 and causing the anvil 152 to pivot. As anvil 152 continues to translate distally, the closure ring 226 causes the anvil 152 to close. Once end effector 150 is closed, the tissue captured between anvil 152 and channel 156 may be cut and stapled.

Once tissue positioned in the end effector 150 is cut and stapled, anvil 152 may be opened to release the tissue. End effector 150 may then be opened to replace staple cartridge 120 with a new staple cartridge. To open end effector 150, the closure ring 226 can be translated proximally by the closure subsystem 200. As closure ring 226 translates proximally, the one or more closure ring tabs 262 engage the anvil tab 264 to pull anvil 152 proximally. As anvil 152 translates proximally, the anvil 152 pivots away from channel 156 to an open position.

Closure Subsystem

Figures 7A, 7B:
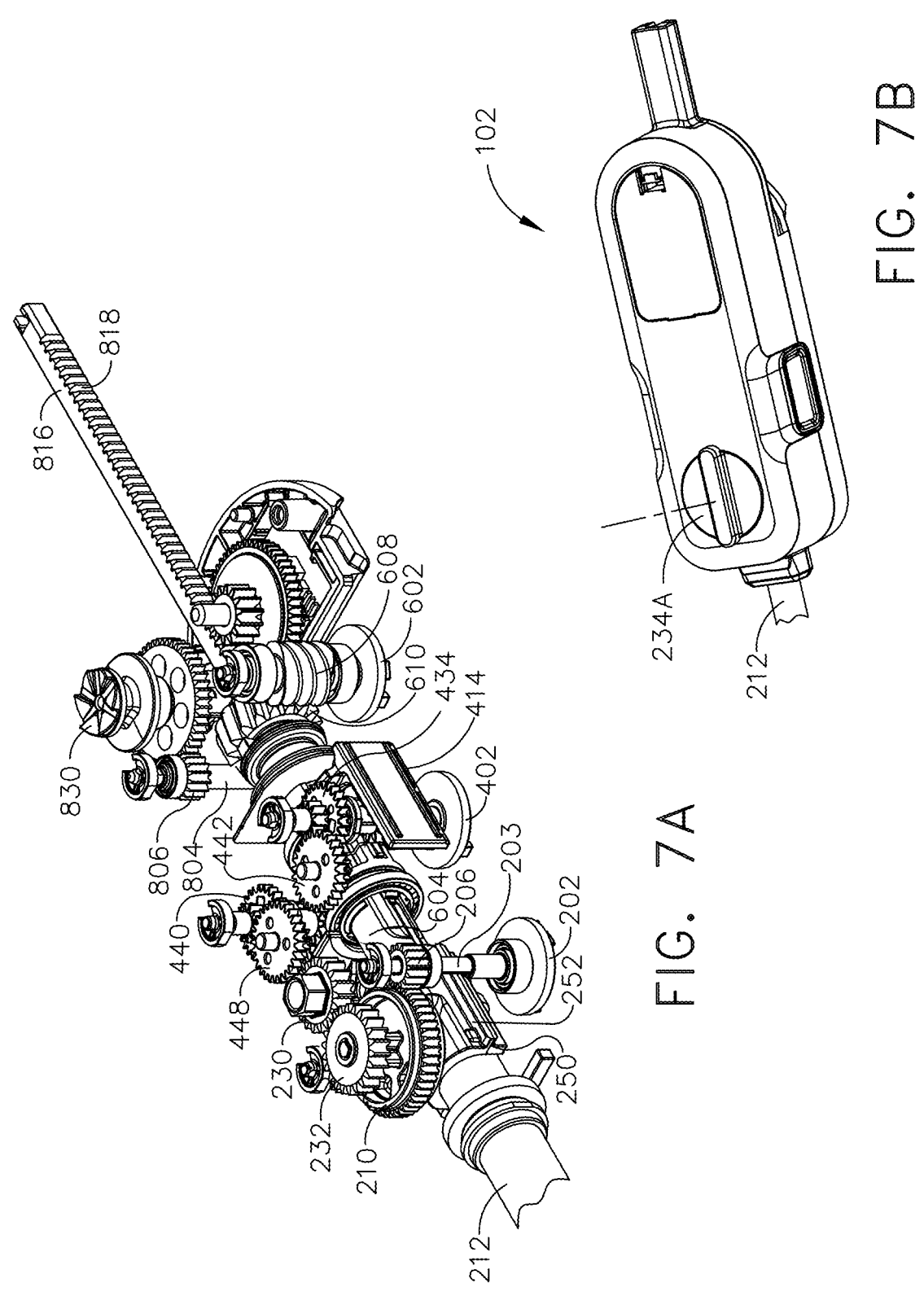
FIG. 7A is a detail view of a closure subsystem, according to aspects of the present disclosure.
FIG. 7B is a perspective view of the housing, according to aspects of the present disclosure.
Figure 7C:
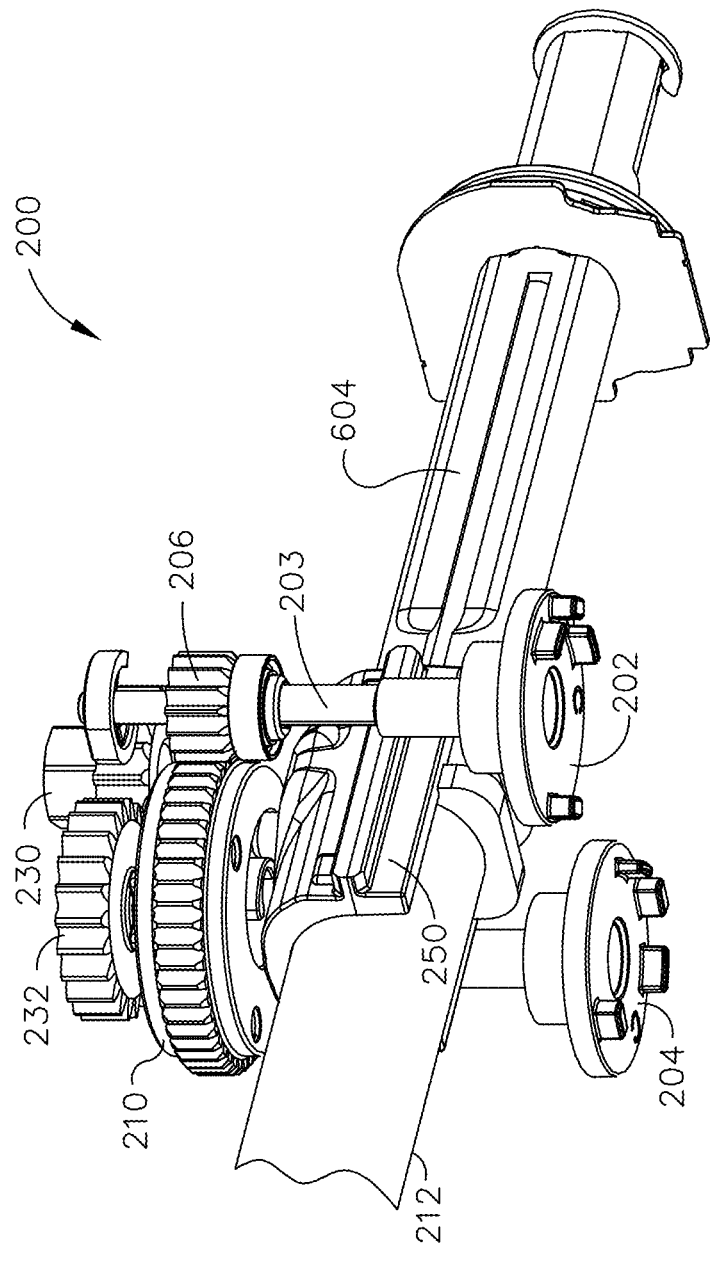
FIG. 7C is another detail view of a closure subsystem, according to aspects of the present disclosure.
Figure 7D:
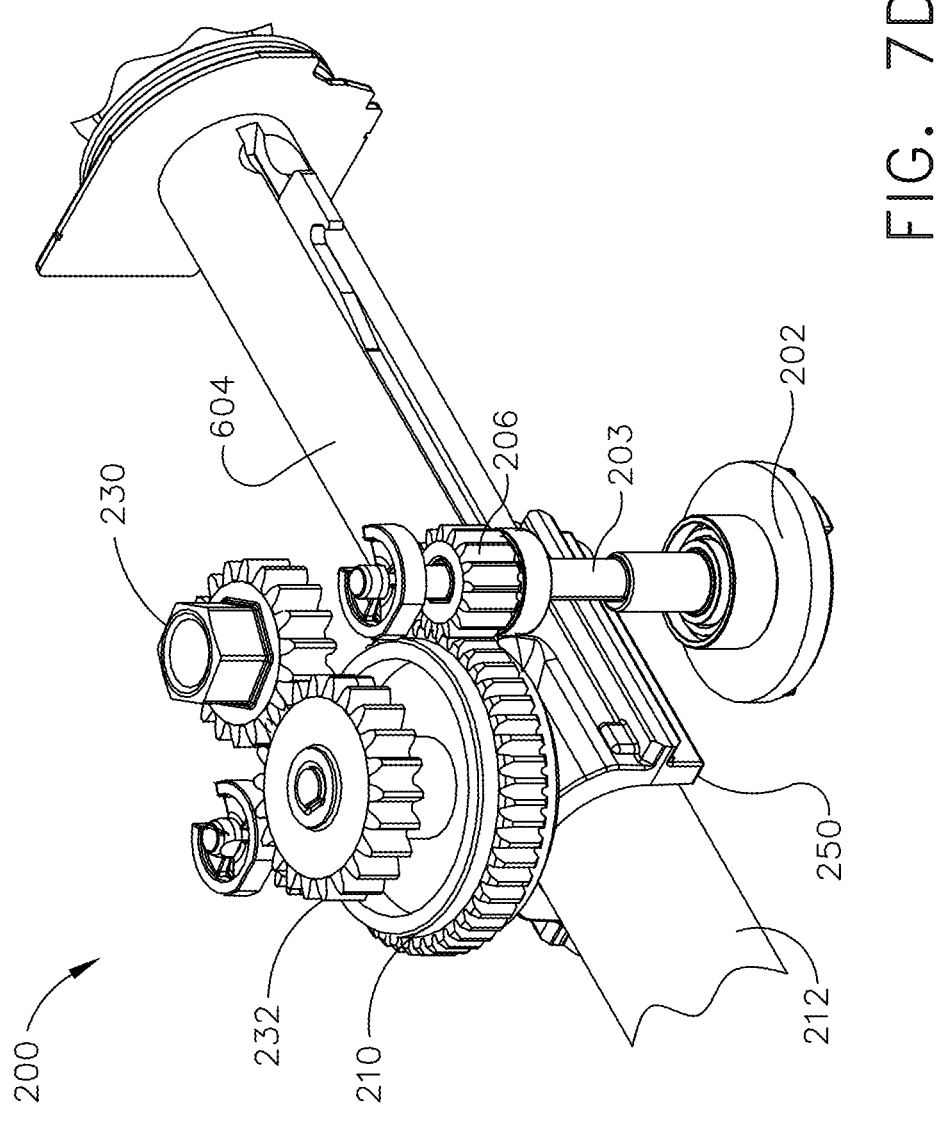
FIG. 7D is another detail view of a closure subsystem, according to aspects of the present disclosure.

FIGS. 7A, 7C, 7D, 7E, and 7I are detail views of a closure subsystem 200, according to aspects of the present disclosure. FIGS. 7A and 7D are top perspective views while FIG. 7C is a bottom perspective view of the closure subsystem 200. The closure subsystem 200 includes a first closure input puck 202 and a second closure input puck 204 (shown in FIG. 7C). The first closure input puck 202 can be configured to engage with a first rotating feature of the robotic arm and the second closure input puck 204 can be configured to engage with a second rotating feature of the robotic arm. In this way, the robotic arm can be configured to transmit a greater amount of force to the closure subsystem 200 to cause the anvil 152 to open and close than would be possible with only a single input puck.

The first closure input puck 202 can be coupled to a first closure input rod 203 that extends into the outer housing 102. The first closure input rod 203 can be further coupled to a first closure spur gear 206. Thus, when the first closure input puck 202 rotates, it will also cause the first closure input rod 203 and the first closure spur gear 206 to rotate. Similarly, the second closure input puck 204 can be coupled to a second closure input rod 205 that extends into the outer housing 102. The second closure input rod 205 can be further coupled to a second closure spur gear 208. Thus, when the second closure input puck 204 rotates, it will also cause the second closure input rod 205 and the second closure spur gear 208 to rotate. The first closure input rod 203 can be held in place by a first retention clip 218 and the second closure input rod 205 can be held in place by a second retention clip 220.

Figures 8A, 8B:
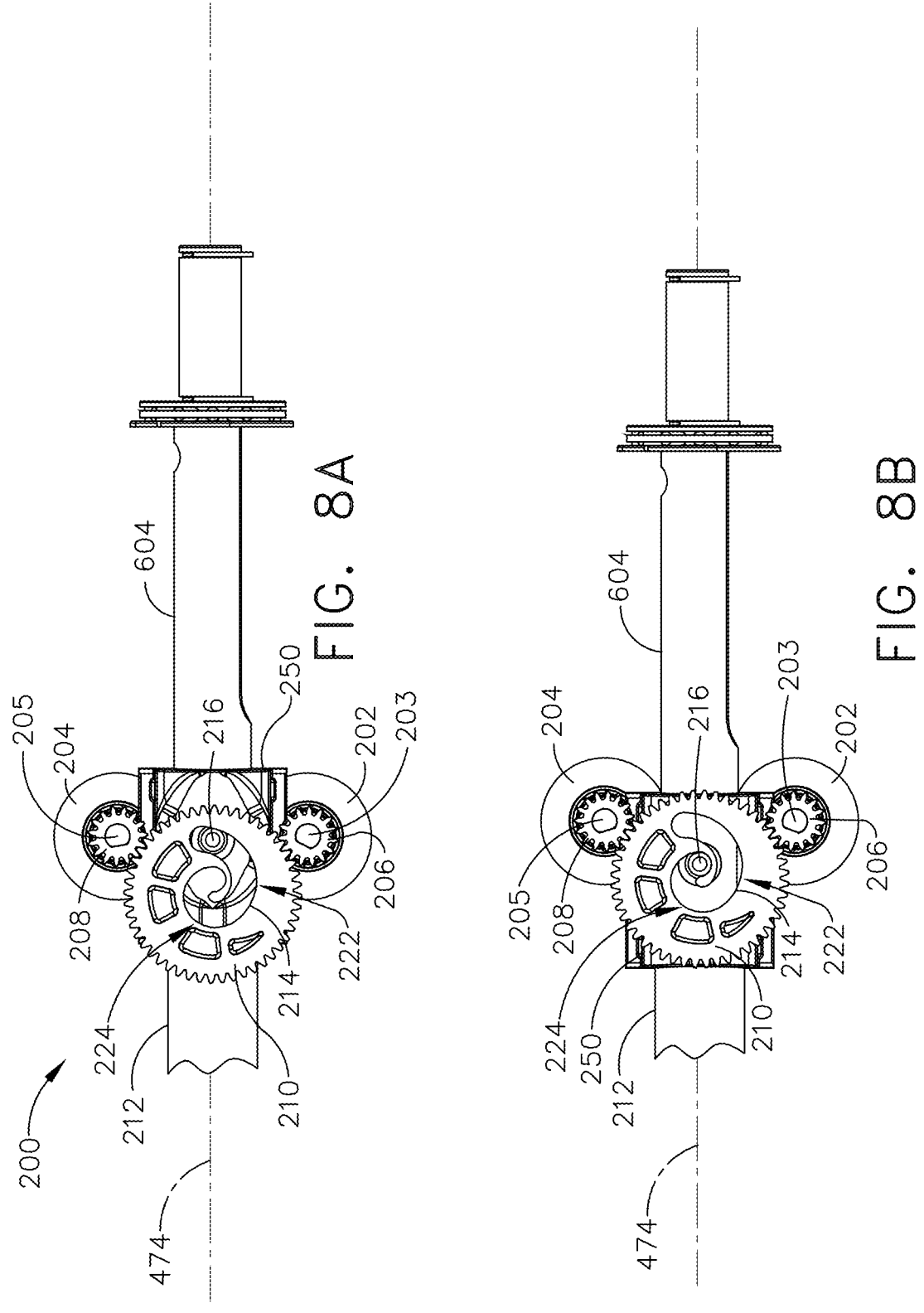
FIG. 8A is a top view of components of the closure subsystem in a first configuration while 8B is a top view of components of the closure subsystem in a second configuration, according to aspects of the present disclosure.

The first closure spur gear 206 and the second closure spur gear 208 can each be rotationally engaged with a closure cam gear 210. As shown in FIGS. 8A and 8B, the closure cam gear 210 includes a closure cam track 214 that can be configured to receive a yoke pin 216 that can be coupled to the closure yoke 250. As the closure cam gear 210 rotates, the closure cam track 214 causes the yoke pin 216 to slide proximally and distally, thereby causing the closure yoke 250 to slide proximally and distally. In other words, as the closure cam gear 210 is rotated in a first direction, the closure cam track 214 will guide the yoke pin 216 along the closure cam track 214 in either the proximal or distal direction. Because the yoke pin 216 is coupled to the closure yoke 250, movement of the yoke pin 216 proximally or distally causes the closure yoke 250 to move proximally or distally. As explained previously, movement of the closure yoke 250 causes the anvil 152 to open or close.

The closure cam track 214 can comprise a non-linear track that can be configured to have a changing movement profile as the closure cam gear 210 rotates. As shown in FIGS. 8A and 8B, a cam track 214 can include a non-linear profile. In some implementations, the cam track 214 can be a logarithmic spiral. The cam track 214 is not necessarily fully logarithmic, and in some instances can be represented by higher order polynomials, as some implementations can include a portion that is non-linear, a portion that has a constant radius, and a portion that connects the non-linear and constant radius portions. These different portions can be created by splines. One novel aspect of this non-linear cam track 214 design is that it can be shaped such that once the yoke pin 216 reaches a portion of the cam track 214 with a constant radius, the closure cam gear 210 rotates but the yoke pin 216 does not move axially. This feature can provide benefits by accounting for, and providing tolerance for, robotic inaccuracies.

Figure 8C:
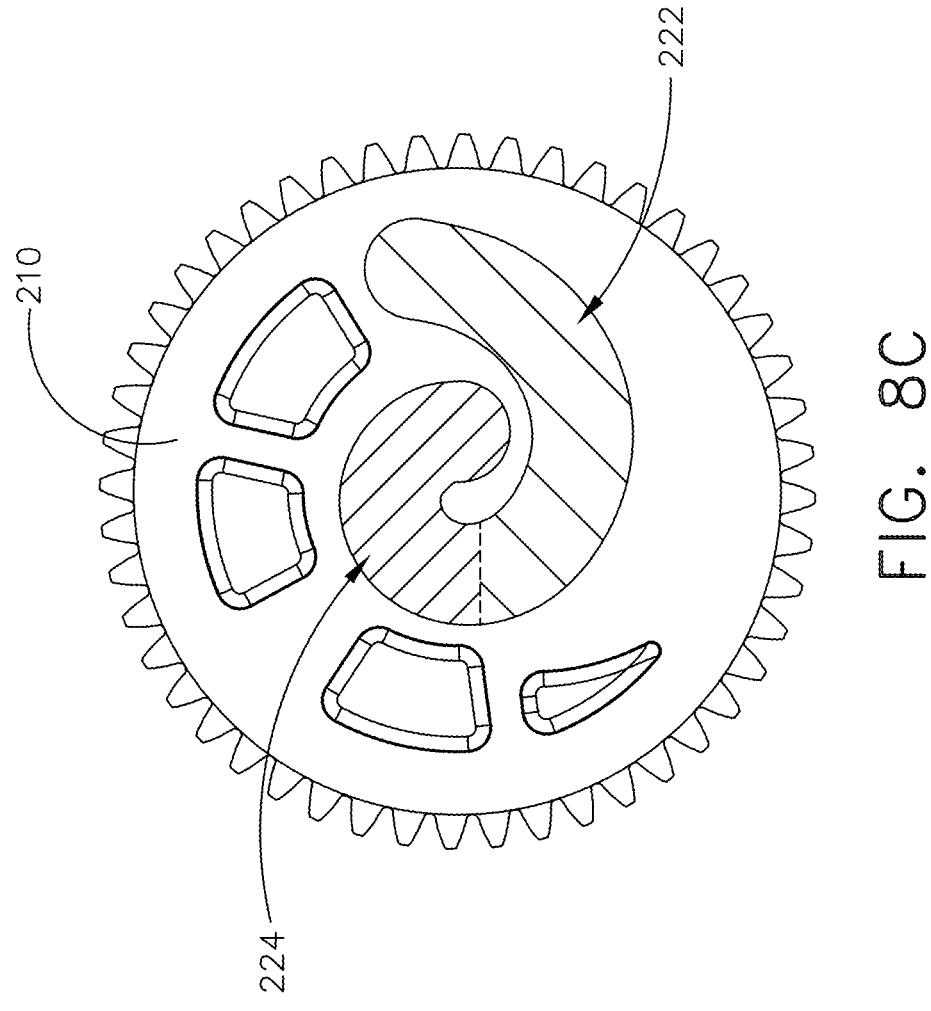
FIGS. 8C and 8D are detail views of a closure cam gear, according to aspects of the present disclosure.
Figure 8D:
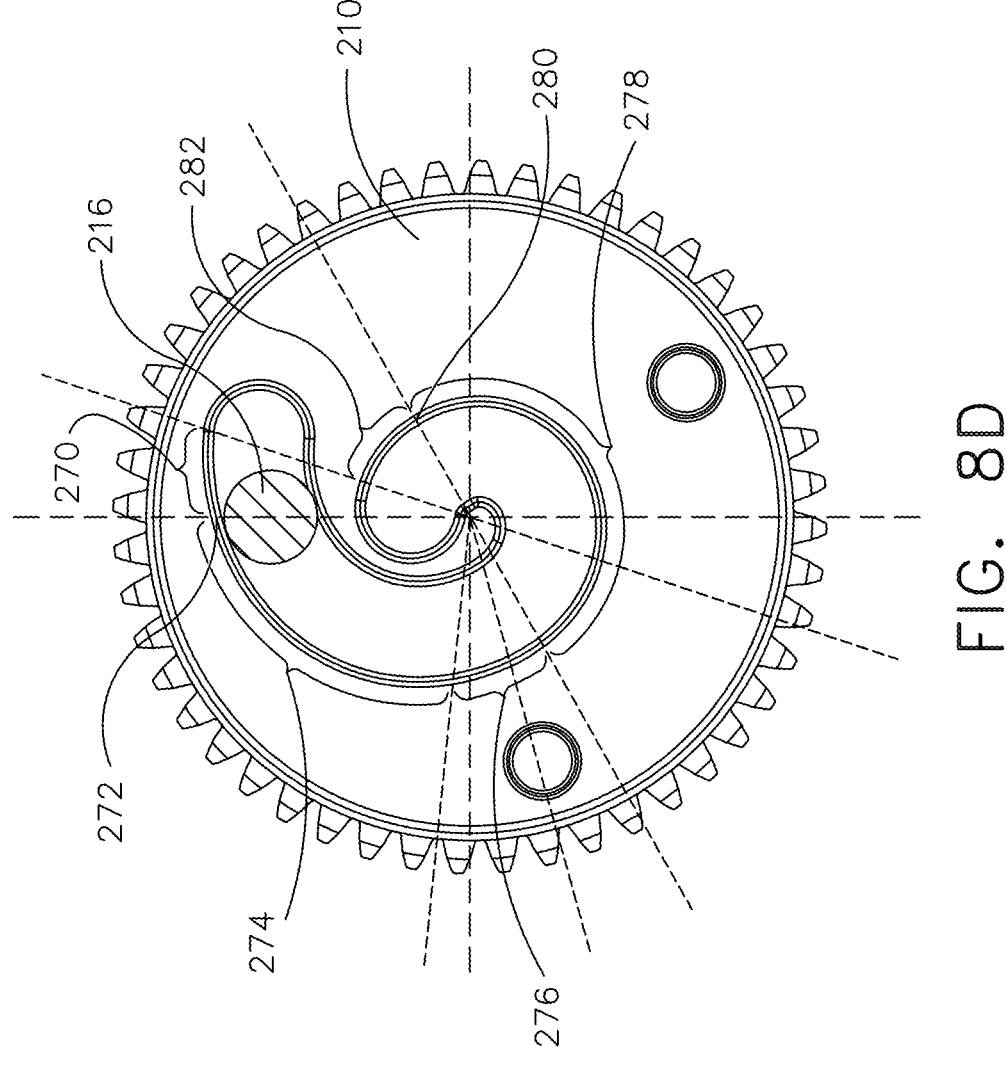

As shown in FIG. 8C, the closure cam track 214 can comprise a first zone 222 and a closure zone 224. The first zone 222 of the closure cam track 214 can be configured to cause the yoke pin 216 and, subsequently, the anvil 152 to compress tissue without causing a great amount of force. The closure zone 224 of the closure cam track 214, on the other hand, can be configured to cause the anvil 152 to compress down on tissue with a force sufficient to keep the end effector 150 in place for cutting and/or stapling of the tissue. The final rotational position of the closure cam track 214, and the overall configuration of the other components of the closure subsystem 200, creates a closure load that meets the requirements of the particular application. In other words, once the yoke pin 216 reaches a final rotational position, the combination of the closure subsystem 200 components can cause the anvil 152 to move to a closed position to close down on tissue. It will be appreciated, however, that the first zone 222 and the closure zone 224 can be configured to comprise alternative percentages of the closure cam track 214 depending on the particular application. Furthermore, the slope of the closure cam track 214 at the first zone 222 and the closure zone 224 can be varied to affect the speed and force with which the anvil 152 opens and closes. It will be understood that the cam track 214 is contiguous, non-linear, and smooth, so FIGS. 8C and 8D depicting the different "zones" is not to indicate that there is a break or discontinuity in certain sections of the cam track 214. FIG. 8A shows a fully open configuration, where the yoke pin 216 is at a position within the cam track 214 such that the anvil 152 is fully open, thereby maximizing the amount of tissue that can be placed in the jaws (e.g., anvil and channel) of the end effector 150. FIG. 8B shows a fully closed configuration, where the yoke pin 216 is within a constant radius portion of the cam track 214 (in this view the yoke pin 216 is also at the very end of the cam track 214).

A fully closed configuration can indicate that the surgical instrument 100 is ready to proceed with firing (e.g., transection and/or stapling). Partially open configurations can exist between the examples shown in FIGS. 8A and 8B wherein the system can grasp tissue.

Referring now to FIG. 8D, which is a bottom view of the closure cam gear 210, the view shows different regions of the cam track 214 that can provide different movement profiles for the yoke pin 216. Referencing this view in FIG. 8D, as the closure cam gear 210 rotates clockwise, the yoke pin 216 translates downward in the view (downward being distally in relation to the shaft 604, see FIGS. 8A and 8B). The regions of the cam track 214 can provide different movement profiles depending on where in the cam track 214 the yoke pin 216 is located. For example, the closure cam gear 210 in FIG. 8D has indications of degrees for reference, up being labeled 0°, left being labeled 90°, down being labeled 180°, and right being labeled 270°. The cam track 214 can include an open dead zone 270 that exists between around −20° and around 0°. The open dead zone 270 is a region beyond an open position 272 that provides a level of tolerance should the closure cam gear 210 be rotated beyond the open position 272. The open position 272, or home position, can be a hard stop position where the closure ring 226 is positioned proximally, allowing the anvil 152 to be fully open (see FIG. 5B). The cam track 214 of FIG. 8D includes a high speed compression region 274 positioned in the next portion of the cam track 214 beyond the open position 272. This high speed compression region 274 can extend from around 0° to around 90°. The high speed compression region 274 has a curvature that enables the yoke pin 216 to transition distally quickly while providing a low amount force (for example clamping force on the anvil 152). This high speed compression region 274 can enable the surgical instrument 100 to grab and position the target tissue. At around 90° on the closure cam gear 210 of FIG. 8D is a force transition region 276. Extending beyond the force transition region 276 is a high force region 278. The high force region 278 can extend from around 90° to around 300° on the closure cam gear 210 of FIG. 8D. This region provides a low speed, high force movement profile for the distal movement of the yoke pin 216. The high force region 278, for example, can be a portion of the movement profile that begins to put pressure on the tissue that is being cut and/or stapled. At around 300° on the closure cam gear 210 of FIG. 8D is a closing target 280. Any point beyond the closing target 280 can be considered as closed, as in the force and distal movement yoke pin 216 are considered met. Extending beyond the closing target 280, and from about 300° to the end of the cam track 214, is a constant force region 282. Like the constant radius portion described above, the constant force region 282 can be a section of the cam track 214 where the closure cam gear 210 rotates but the yoke pin 216 does not move axially. This can help to provide tolerance for any positional error by the surgical robot 1100.

The closure subsystem 200 can further include a manual closure spur gear 230 that is coupled to a manual closure handle 234 (as shown in FIGS. 7B and 7E-7I) that extends through the outer housing 102. The manual closure handle 234 can be used, for example, by a surgical staff if the surgical robot is unable to open or close the anvil 152. The manual closure spur gear 230 can be rotationally coupled to a manual closure cam gear 232 that can be keyed to the closure cam gear 210. In this way, rotation of the manual closure handle 234 will cause the manual closure spur gear 230 and the manual closure cam gear 232 to rotate, thereby causing the closure cam gear 210 to rotate and open or close the anvil 152. As will be appreciated, the manual closure handle 234 provides a surgical staff with the ability to open and close the anvil 152 when the surgical instrument 100 is disconnected from a surgical robot or to override the opening or closing of the anvil 152 when connected to the surgical robot.

As shown in FIGS. 7E-7I, the manual closure handle 234, in some examples, includes a manual closure handle grip 236 and a manual closure handle clip 238. The manual closure handle grip 236 can extend beyond an outer portion of the housing 102 such that the physician or surgical staff can grip the manual closure grip 236 and rotate it to cause the anvil 152 to open or close. The manual closure handle clip 238 can be configured to extend through the manual closure handle grip 236 and into the housing 102 to attached the manual closure handle 234 to the housing 102. The manual closure handle clip 238 can include one or more protruding features that can snap into place when pushed into the housing 102 to attached the manual closure handle 234 to the housing 102. In other examples, the manual closure handle grip 236 and the manual closure handle clip 238 can be integrated into a single component.

Figure 7F:
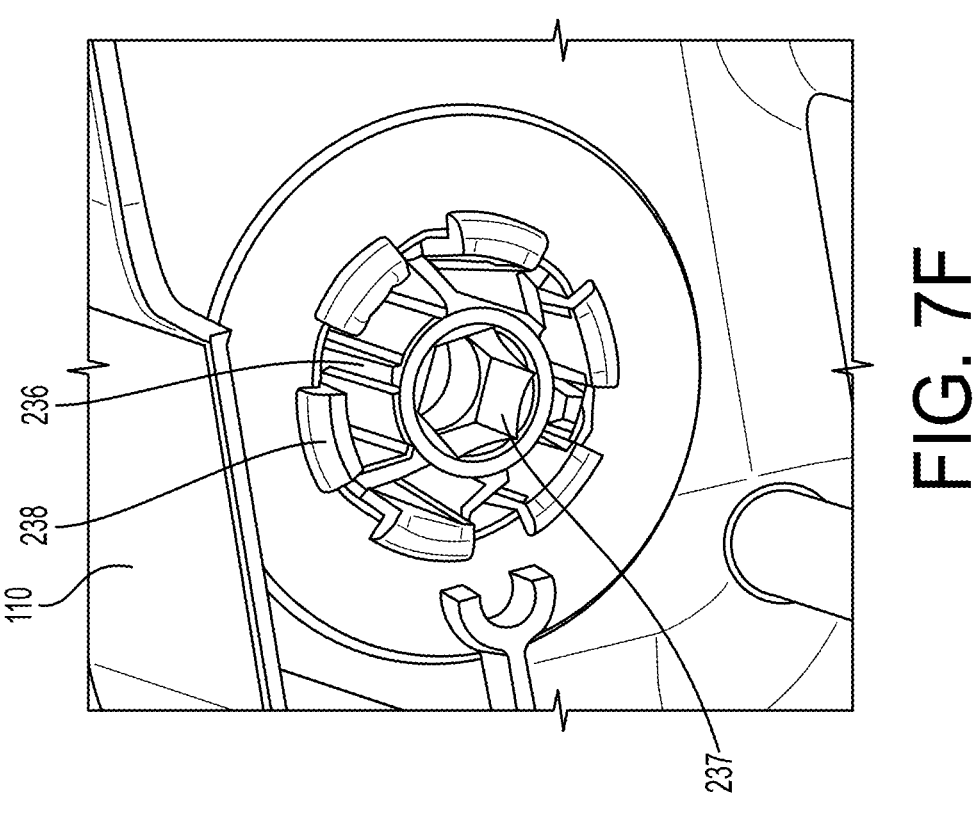
FIG. 7F is an underside perspective view of the manual closure handle, according to aspects of the present disclosure.
Figure 7E:
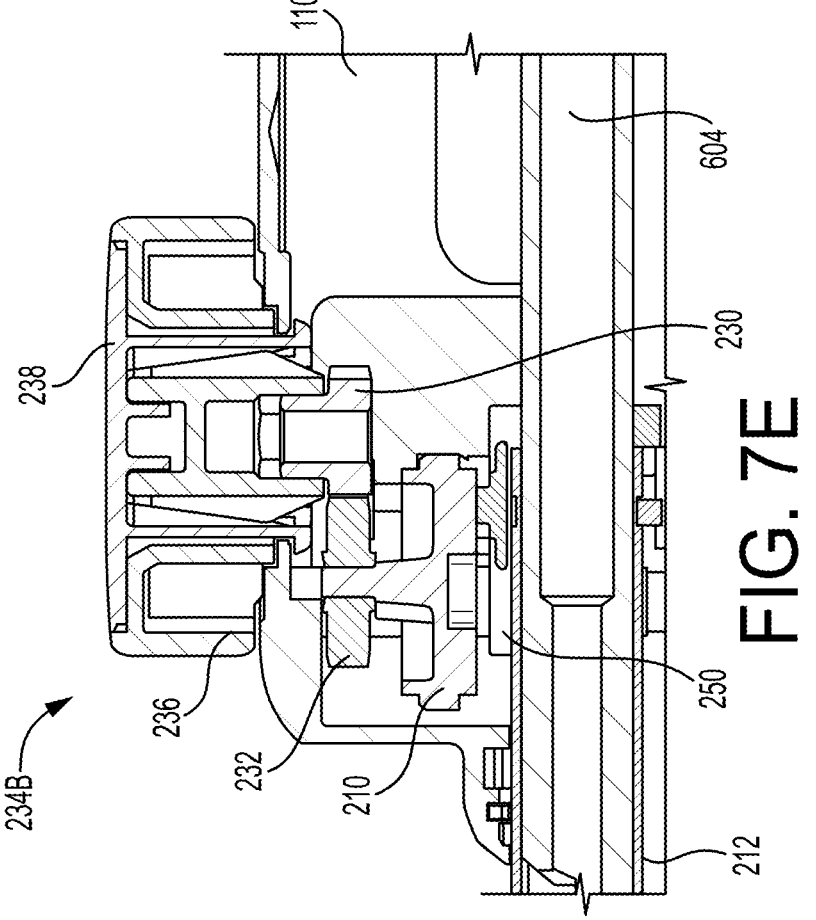
FIG. 7E is a cross-sectional view taken vertically along the longitudinal axis of the surgical instrument and showing details of a manual closure handle, according to aspects of the present disclosure.
Figure 7H:
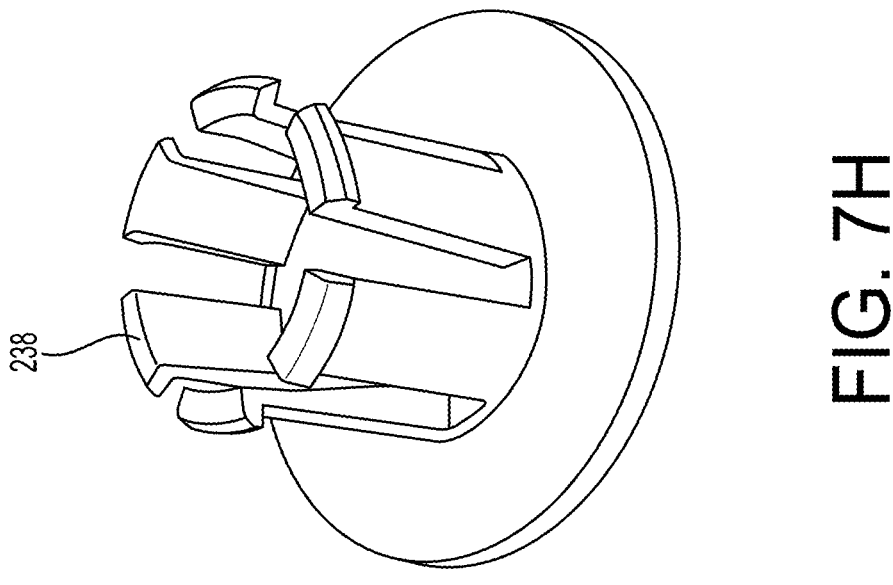
FIG. 7H is a detail view of a manual closure handle clip, according to aspects of the present disclosure.
Figure 7G:
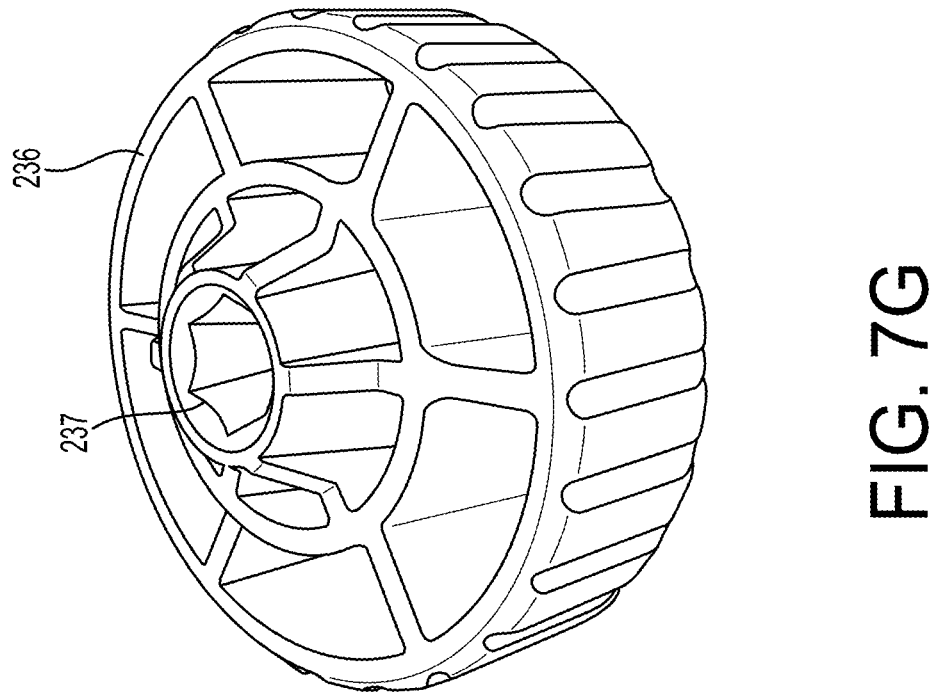
FIG. 7G is a detail view of a manual closure handle grip, according to aspects of the present disclosure.
Figure 7I:
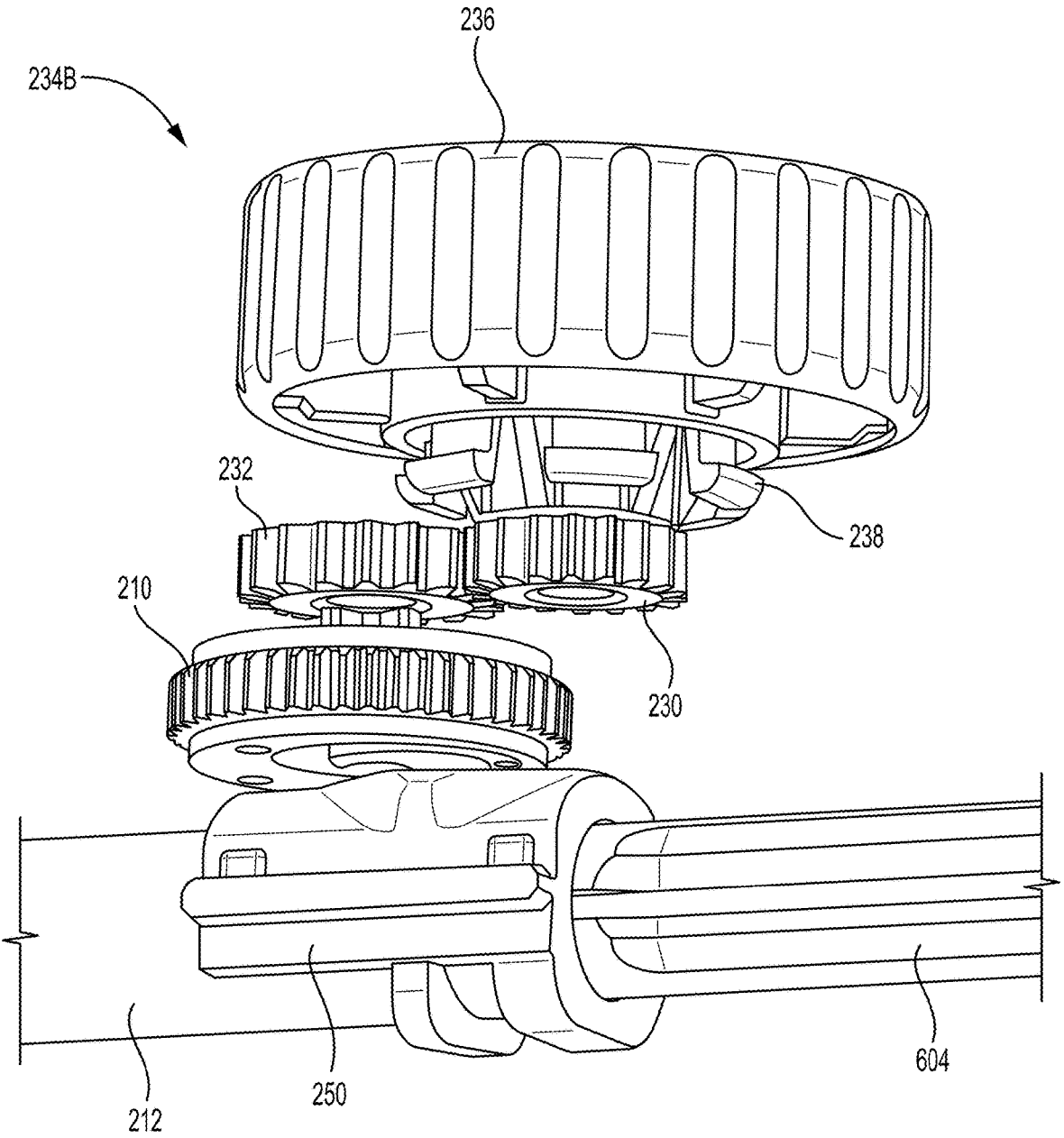
FIG. 7I is a detail view of the closure subsystem with manual closure handle, according to aspects of the present disclosure.

The manual closure handle grip 236 can attach to the manual closure spur gear 230 by, for example but not limitation, receiving a protrusion of the manual closure spur gear 230 into a recess formed into the manual closure handle grip 236 (as shown in FIGS. 7E and 7F). The manual closure handle grip 236 can include engagement surfaces 237 that can align with corresponding engagement surfaces of the manual closure spur gear 230 to transfer forces from the manual closure handle grip 236 to the manual closure spur gear 230 when rotated. For example, the protrusions of the manual closure spur gear 230 and the recess of the manual closure handle grip 236 can be a hex head or other similar features.

Although not shown, in some examples, the manual closure handle grip 236 could include geometry that limits the travel, or provides some resistance to the travel, of the manual closure handle grip 236 at predetermined locations such that the manual closure handle grip 236 is stopped or at least slowed at positions corresponding to desired positions of the opening and closing of the anvil 152. Alternatively, or in addition, the manual closure handle grip 236 or the manual closure handle clip 238 can include markings, colors, protrusions, recesses, etc. that indicate the position of the anvil 152. In some examples. The manual closure handle grip 236 or the manual closure handle clip 238 can include transparent features that reveal indicators at certain positions of rotation to indicate the status. Furthermore, the manual closure handle 230 and/or the closure subassembly 200 can include torque limiting features to prevent over torquing of the closure subassembly 200.

Articulation Subsystem

Figure 9:
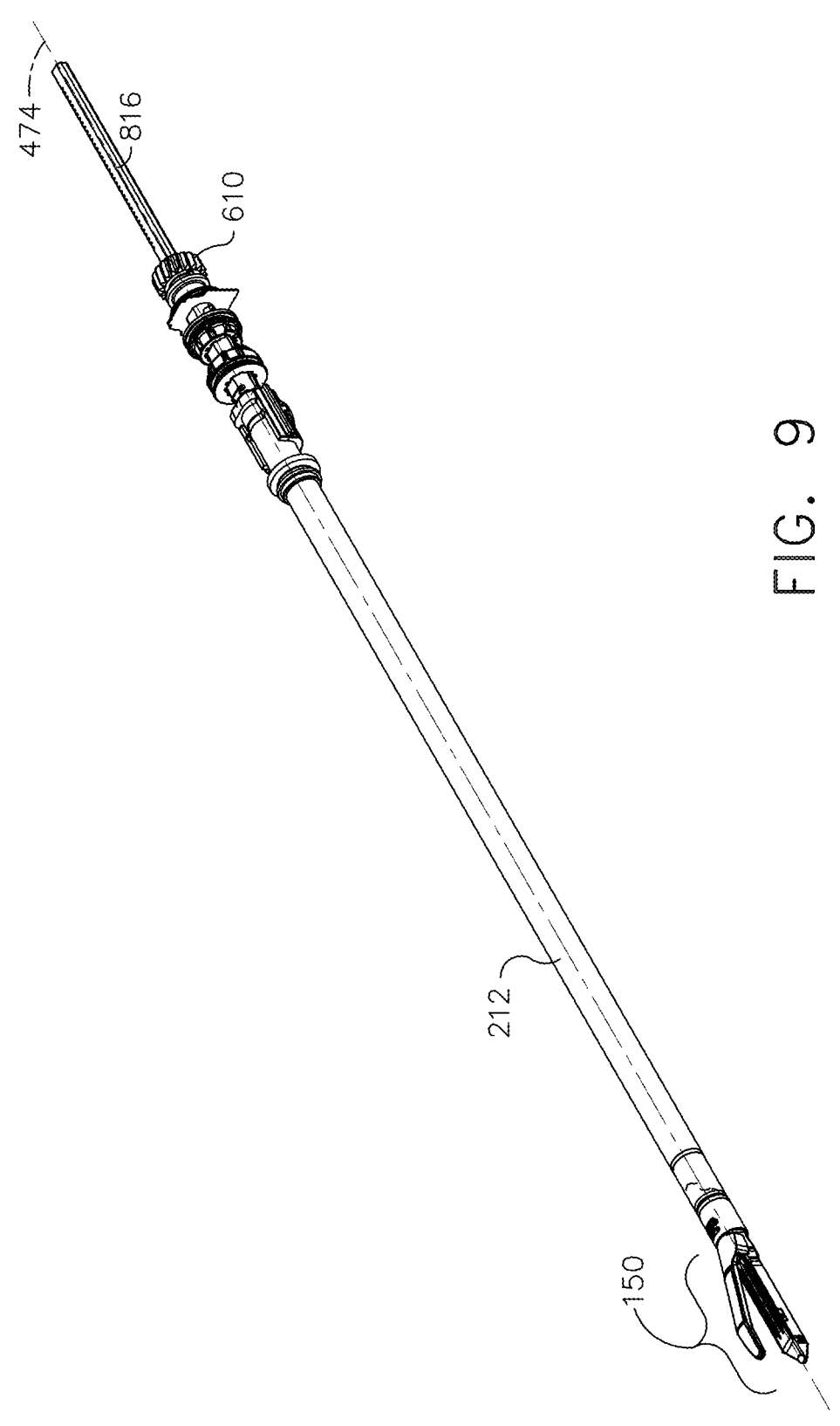
Figure 10:
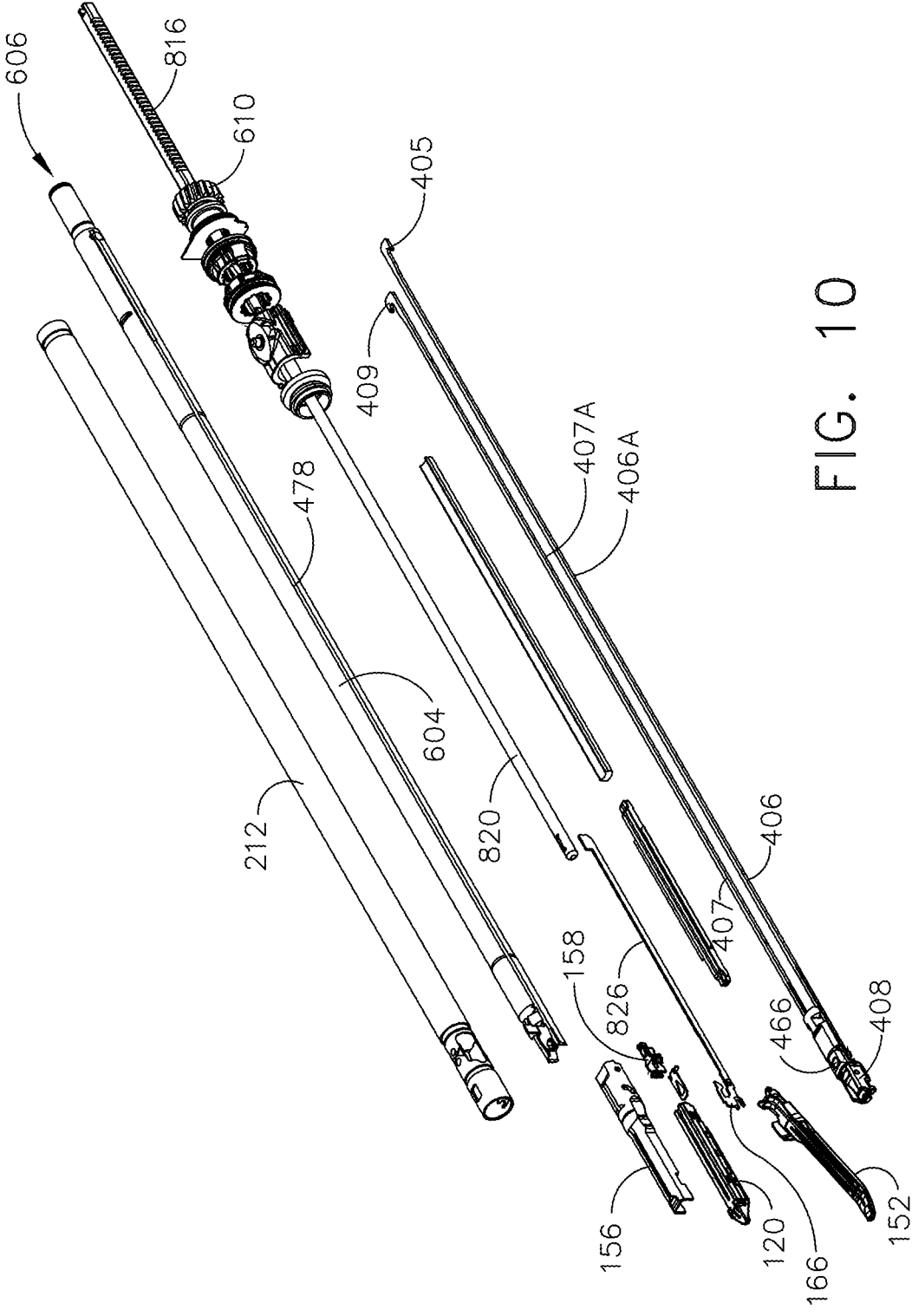
FIG. 10 is an exploded view of the surgical instrument, according to aspects of the present disclosure.

FIG. 9 is a perspective view of the surgical instrument 100 while FIG. 10 is an exploded perspective view of the surgical instrument 100. As shown, the surgical instrument 100 includes a cartridge 120 that includes staples configured to staple tissue. The surgical instrument 100 can further include a knife guide 158, a firing rod 820, and a firing rack 816 that can cause a knife to cut tissue, as will be described in greater detail herein. Furthermore, the surgical instrument 100 includes a shaft 604 having a shaft lumen 606. The shaft 604, as will be described in greater detail herein, can be disposed within the closure tube 212 and be coupled to a worm follower 610 that can cause the shaft 604 and end effector to rotate about the longitudinal axis 474 of the surgical instrument 100.

The surgical instrument 100 includes an articulation subsystem 400. As shown in FIG. 10, the surgical instrument 100 includes a first articulation rod 406A and a second articulation rod 407A that can be configured to cause a distal channel retainer 408 and, subsequently, the end effector 150 to articulate in a first and second direction transverse to a longitudinal axis 474 of the surgical instrument 100. The first articulation rod 406A and the second articulation rod 407A can be configured to be at least partially disposed in a rod groove 478 disposed on either side of the shaft 604.

Views of the articulation of the distal end of the surgical instrument 100 are shown in FIGS. 11A, 11B, 12A, 12B, and 12C while detailed views of the proximal portions of an example articulation subsystem 400 are provided in FIGS. 13A-15C. The articulation subsystem 400 includes a first articulation rod 406A and a second articulation rod 407A that each extend distally to a distal channel retainer 408. The proximal end of the first articulation rod 406A and the second articulation rod 407A can each include a hook (first articulation rod hook 405 and second articulation rod hook 409, shown in FIGS. 10, 15A, 15B, and 15C) or other attachment that constrains the articulation rod proximally (e.g., to a first articulation bushing 426 and a second articulation bushing 428). In some examples, the first articulation rod 406A and the second articulation rod 407A can each be pinned, bolted, welded, adhered, or otherwise attached to a first rack 414A and a second rack 418A, respectively. The distal end of the first articulation rod 406A and the second articulation rod 407A can each be connected to a distal channel retainer 408 that can pivot back and forth (e.g., left and right) to move, or articulate, an end effector 150 of the surgical instrument 100. The first articulation rod 406A can be attached to the distal channel retainer 408 via a first channel retainer pin 410 and the second articulation rod 407A can be attached to the distal channel retainer 408 via a second channel retainer pin 411. An attachment end 468 of the distal channel retainer 408 can, for example, be attached to a channel 156 of the end effector 150 to articulate the end effector 150. The attachment end 468 can also include a band slot 484 for a series of bands 826 to pass through as part of the transection subsystem 800.

Figures 11A, 11B:
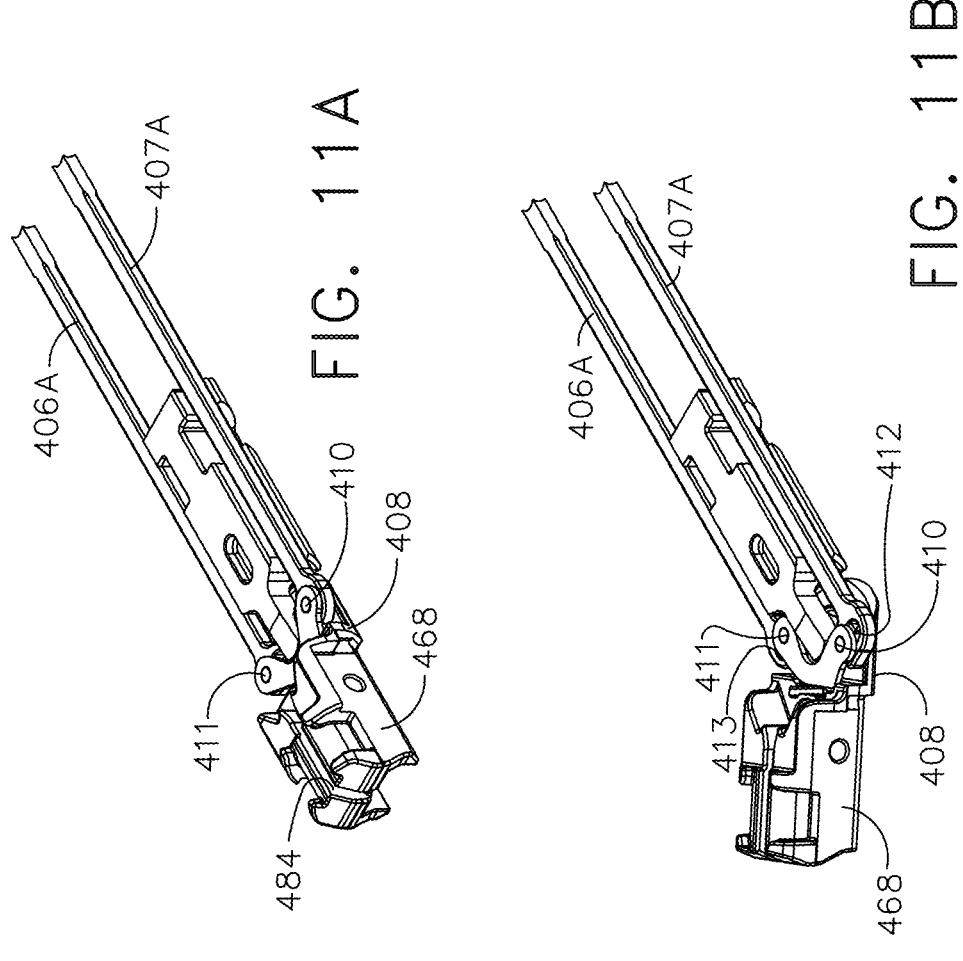
FIGS. 11A and 11B show detail views of components of the articulation subsystem, according to aspects of the present disclosure.
Figure 12A:
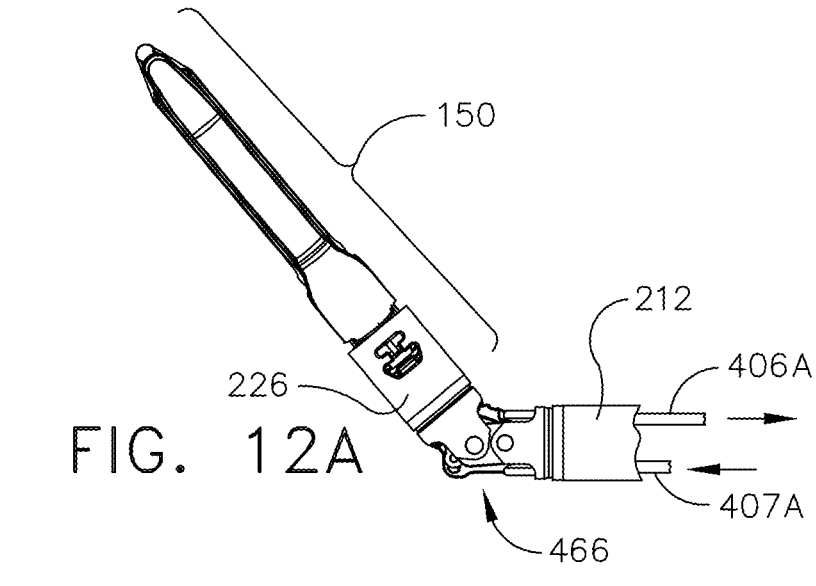
FIG. 12A shows the articulation system fully articulated in one direction.
Figure 12B:
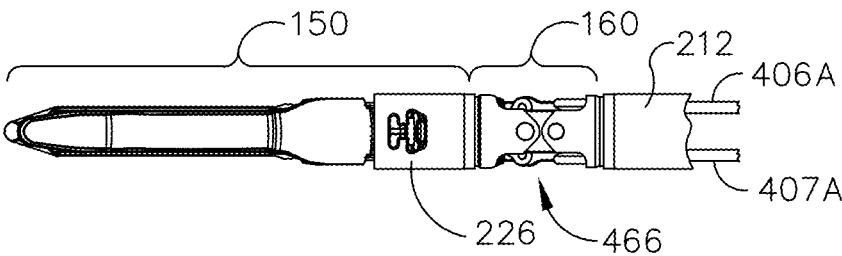
FIG. 12B shows the articulation system at 0° degrees of articulation.
Figure 12C:
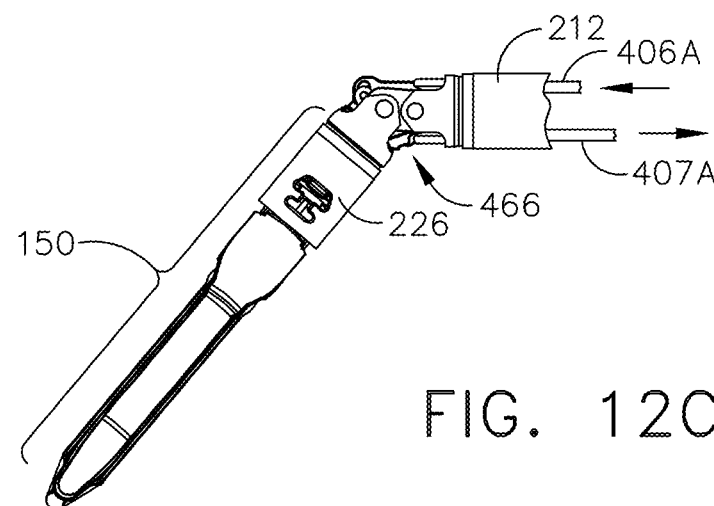
FIG. 12C shows the articulation system fully articulated in another direction.

Referring now to FIGS. 12A, 12B, and 12C, the first articulation rod 406A and the second articulation rod 407A can articulate the distal channel retainer 408 back and forth about an articulation pivot point 466 by pushing or pulling a respective side of the distal channel retainer 408. FIG. 12A illustrates the end effector 150 articulated to a first position, FIG. 12B illustrates the end effector 150 in a central position, and FIG. 12C illustrates the end effector 150 is a second position. To articulate the end effector 150 back and forth, the distal channel retainer 408 includes the first retainer pin 410 (as shown in FIG. 11B), and the first articulation rod 406A includes a first rod aperture 412 distally that engages the first retainer pin 410. Similarly, the distal channel retainer 408 includes the second retainer pin 411, and the second articulation rod 407A includes a second rod aperture 413 distally that engages the second retainer pin 411. As the first articulation rod 406A translates proximally (as shown by the arrow in FIG. 12C), the first articulation rod 406A pulls the first retainer pin 410 proximally and thus articulates the distal channel retainer 408 about the articulation pivot point 466 in one direction. The second articulation rod 407A can translate distally to permit the channel retainer 408 to articulate about the articulation pivot point 466. Similarly, as the second articulation rod 407A translates proximally (as shown by the arrow in FIG. 12A), the second articulation rod 407A pulls the second retainer pin 411 proximally and thus articulates the distal channel retainer 408 about the articulation pivot point 466 in the opposite direction. The first articulation rod 406A can translate distally to permit the channel retainer 408 to articulate about the articulation pivot point 466. The first articulation rod aperture 412 and the second articulation rod aperture 413 can each be oblong, as shown in FIG. 11B, to account for the translation of the first and second retainer pins 410, 411 laterally as the distal channel retainer 408 rotates, since the first articulation rod 406A and second articulation rod 407A moves only axially and is constrained to the shaft 604 within a rod groove 478. FIG. 10 shows a view of the rod groove 478 along the length of the shaft 604. Note that in other examples, the proximal and distal motions can be reversed. For example, the rotation illustrated in FIG. 12A can be accomplished by any one of distal movement of the first articulation rod 406A, proximal movement of the second articulation rod 407A or the coordinated movements of both articulation rods 406A, 407A. The same holds true for the entire articulation range of motion.

Figure 13A:
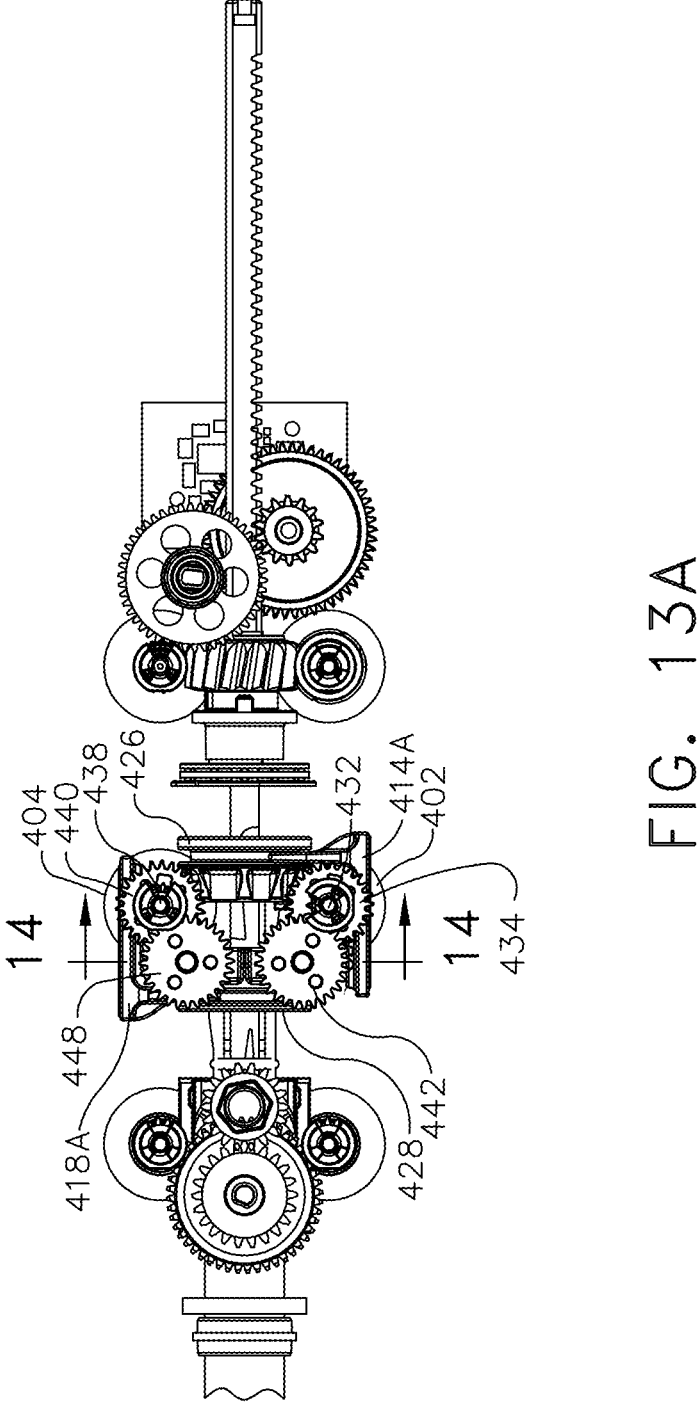
FIG. 13A is a detailed view of components of the articulation subsystem, according to aspects of the present disclosure.
Figure 13B:
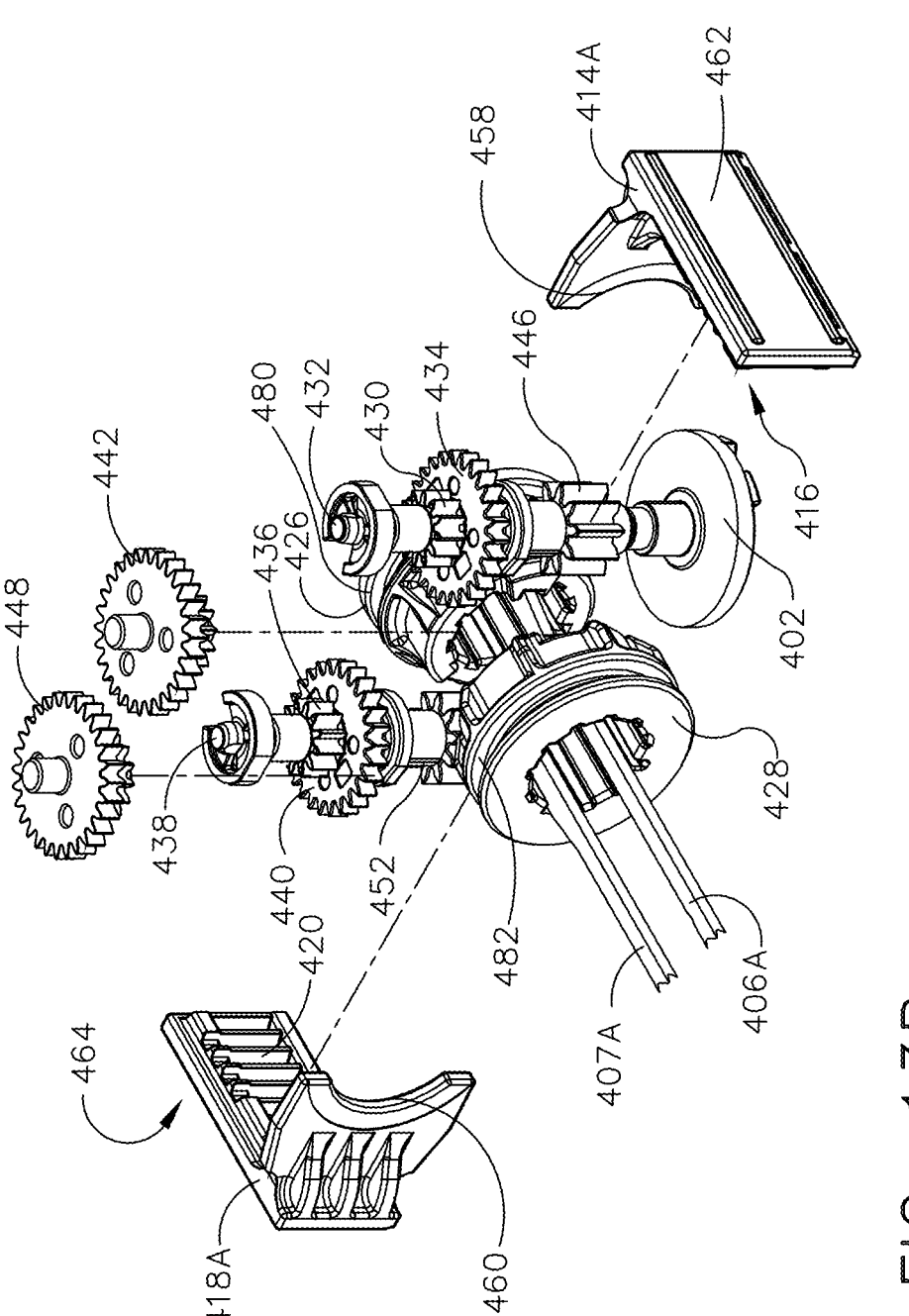
FIG. 13B is an exploded view of components of the articulation subsystem, according to aspects of the present disclosure.
Figure 14:
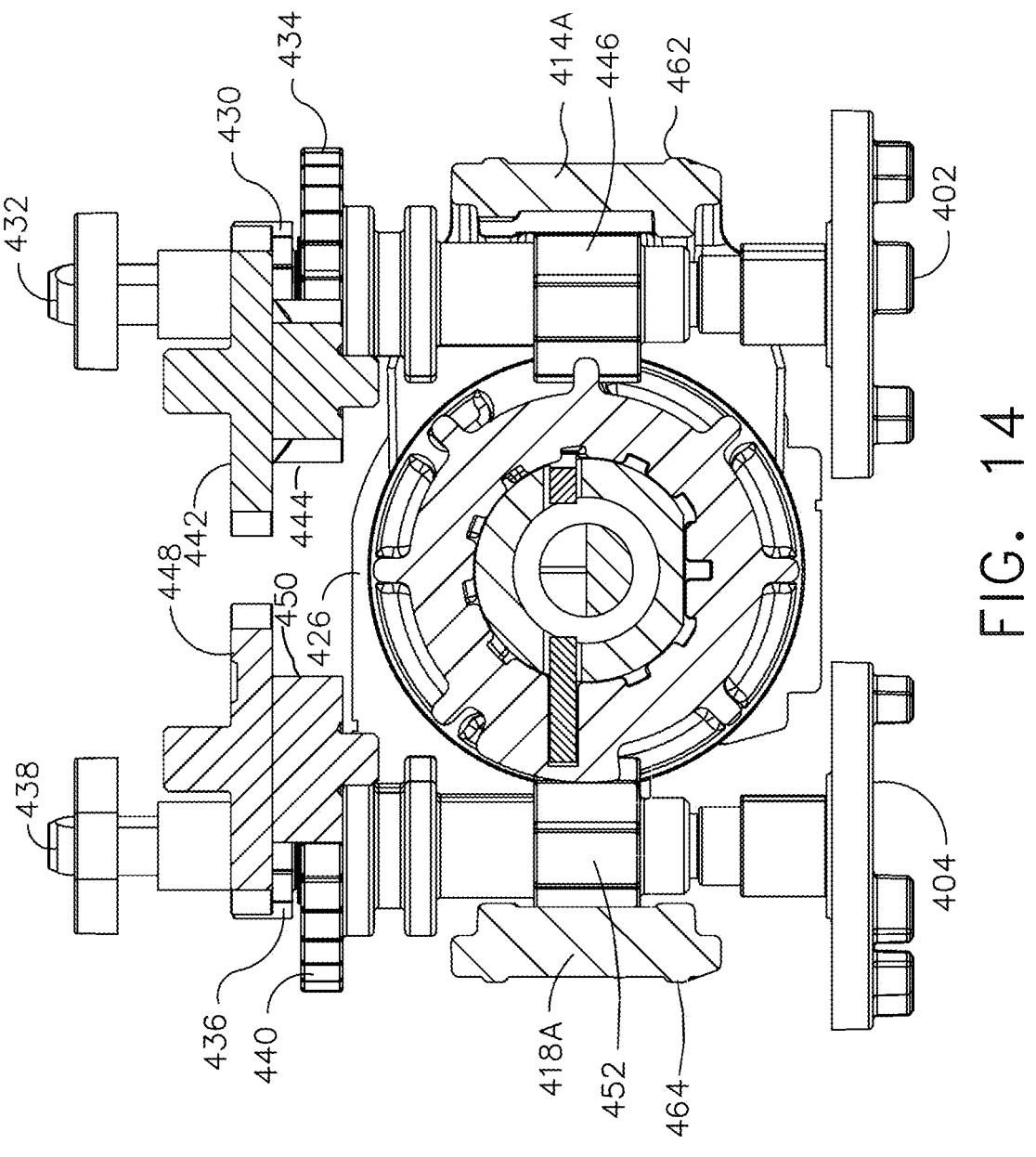
FIG. 14 is a cross-sectional view of the components of the articulation subsystem, according to aspects of the present disclosure.

Referring now to FIGS. 13A and 13B, which are a detailed view and an exploded of the proximal portions of the articulation subsystem 400, respectively. Additionally, FIG. 14 shows a cross-sectional view of the articulation subsystem 400 taken along line A-A of FIG. 13A. The articulation subsystem 400 includes features that accommodate the roll functions of the surgical instrument 100. As will be described in greater detail below with respect to the roll subsystem 600, the surgical instrument 100 includes a shaft 604 that can roll, i.e., rotate with respect to a longitudinal axis 474 of the surgical instrument 100, to allow a full range of articulation for the end effector 150. To elaborate, the shaft 604 can be directly connected to the end effector 150, and therefore the combination of rolling of the shaft 604 (via the roll subsystem 600) and articulating the end effector 150 (via the articulation subsystem 400) enables the end effector 150 to articulate with more degrees of freedom than simply left to right by pivoting the distal channel retainer 408. Access to the surgical site is thereby improved due to the combination of the articulation, roll, and insertion of the surgical instrument 100.

Figure 15A:
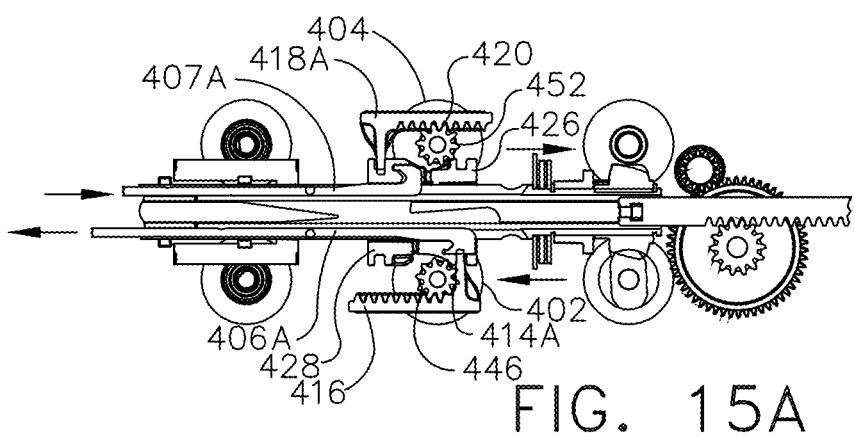
FIGS. 15A-15C show detail views of the articulation subsystem, according to aspects of the present disclosure.
Figure 15B:
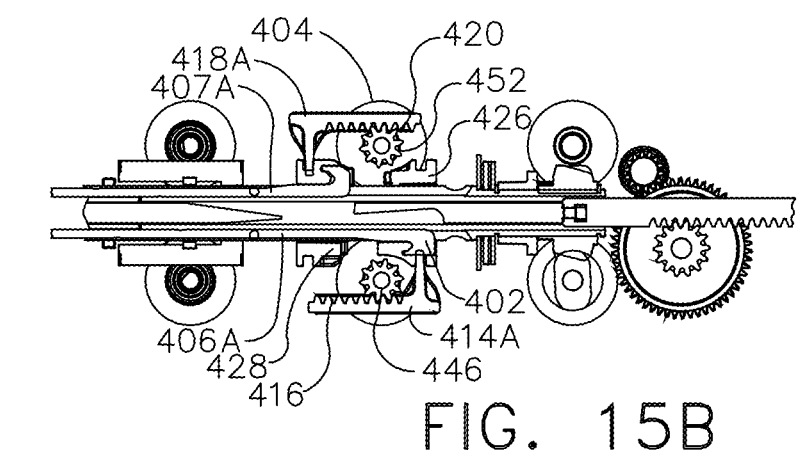
Figure 15C:
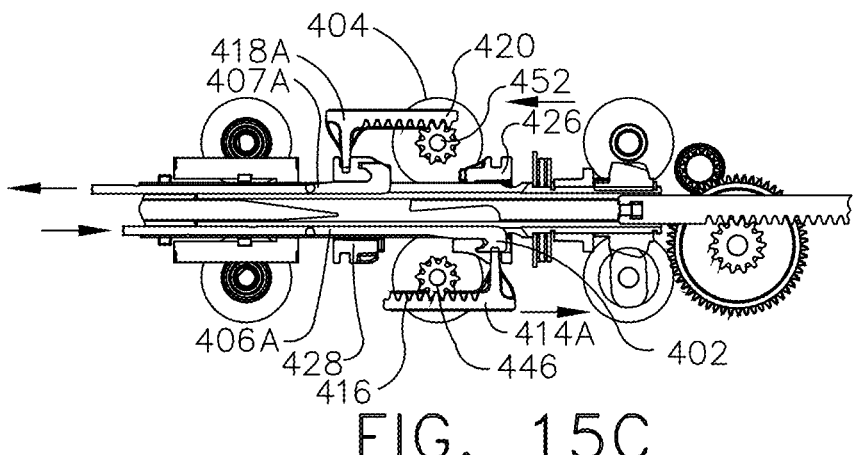

The first articulation rod 406A and the second articulation rod 407A each extend along the rotatable shaft 604, for example within the rod groove 478. To account for the ability of the first articulation rod 406A and the second articulation rod 407A to rotate with the shaft 604, the articulation subsystem 400 includes bushings (i.e., first articulation bushing 426 and second articulation bushing 428) that allow the rotatable robotic outputs to move the articulation subsystem 400 proximally and distally (for example to move the first articulation rod 406A and the second articulation rod 407A) along the shaft 604, while also allowing the shaft 604 to rotate within the articulation subsystem 400. The articulation subsystem 400 includes a first rack 414A that can be moved via a series of gearing by rotation of the first articulation input puck 402, the first articulation input puck 402 being engageable with a corresponding rotatable robotic output. The inside of the first rack 414A includes rack gearing 416 (as shown in FIGS. 15A, 15B, and 15C) that facilitates axial translation of the first rack 414A (e.g., distal and proximal within the outer housing 102 as indicated by the arrows in FIGS. 15A and 15C). The articulation subsystem 400 includes a second rack 418A that can be moved via a series of gearing by rotation of the second articulation input puck 404, the puck 404 being engageable with a corresponding rotatable robotic output. The inside of the second rack 418A includes rack gearing 420 (as shown in FIGS. 15A, 15B, and 15C) that enables axial translation of the second rack 418A (e.g., distal and proximal within the outer housing 102 as indicated by the arrows in FIGS. 15A and 15C).

To account for the rotation of the shaft 604, the articulation subsystem 400 includes a first articulation bushing 426 that is rotatable with the shaft 604 and is rotatably independent of the first rack 414A. In other words, the rolling of the shaft 604 will also roll the first articulation bushing 426, all while the first rack 414A remains rotationally stable within the outer housing 102. The first articulation bushing 426 can slide from a first position to a second position along a longitudinal axis 474 of the rotatable shaft 604, thereby moving the first articulation rod 406A proximally and distally. The first rack 414A includes a first housing track surface 462 (as shown in FIG. 14) that moves axially within a corresponding track in the outer housing 102, thereby enabling the first rack 414A to slide axially but not rotationally. The first housing track surface 462 and the first bushing bearing surface 458 can be at 90° with respect to each other. The articulation subsystem 400 includes a second articulation bushing 428 that is rotatable with the shaft 604 and is rotatably independent of the second rack 418A. In other words, the rolling of the shaft 604 will also roll the second articulation bushing 428, all while the second rack 418A remains rotationally stable within the outer housing 102. The second articulation bushing 428 can slide from a first position to a second position along the longitudinal axis 474 of the rotatable shaft 604, thereby moving the second articulation rod 407A proximally and distally. The second rack 418A includes a second housing track surface 464 (as shown in FIG. 14) that moves axially within a corresponding track in the outer housing 102, thereby enabling the second rack 418A to slide axially but not rotationally. The second housing track surface 464 and the second bushing bearing surface 460 can be at 90° with respect to each other.

The articulation subsystem 400 includes a first articulation drive shaft 432 extending from the first articulation input puck 402 and including a first drive gear 430 that can be keyed to the first articulation drive shaft 432. Rotation of the first articulation input puck 402 by the corresponding robotic output can therefore rotate the first drive gear 430. The articulation subsystem 400 includes a first rack gear 434, which can in some instances be a hollow tube gear that slides over the first articulation drive shaft 432, thereby providing a mechanical advantage to the system while also conserving space within the outer housing 102. The first rack gear 434 can be rotatably coupled to the first articulation drive shaft 432 by means of a first compound gear 442 that has stepped teeth 444, one portion of the stepped teeth 444 being engaged with the first drive gear 430, and the other portion of the stepped teeth 444 being engaged with the first rack gear 434. As such, rotation of the first articulation drive shaft 432 rotates the first drive gear 430, rotation of the first drive gear 430 rotates the first compound gear 442, and rotation of the first compound gear 442 rotates the first rack gear 434 that is surrounding the first articulation drive shaft 432. Further, the first rack gear 434 includes first rack gear teeth 446 that engage with the rack gearing 416 of the first rack 414A. Rotation of the first rack gear 434 therefore causes the first rack 414A to translate proximally and distally to move the first articulation bushing 426. With this configuration, rotation of the first input puck 402 in a clockwise direction (when viewed from a perspective showing the surface of the first input puck 402 that is configured to engage with the robotic arm 1100 (e.g., when viewing the outer-facing surface of first input puck 402)) can cause the first rack 414A to move proximally and rotation of the first puck 402 in a counter-clockwise direction can cause the first rack 414A to move distally.

Similarly, the articulation subsystem includes a second articulation drive shaft 438 extending from the second articulation input puck 404 and including a second drive gear 436. Rotation of the second articulation input puck 404 by the corresponding robotic output can therefore rotate the second drive gear 436. The articulation subsystem 400 includes a second rack gear 440, which can in some instances be a hollow tube gear that slides over the second articulation drive shaft 438. The second rack gear 440 can be rotatably coupled to the second articulation drive shaft 438 by means of a second compound gear 448 that has stepped teeth 450, one portion of the stepped teeth 450 being engaged with the second drive gear 436, and the other portion of the stepped teeth 450 being engaged with the second rack gear 440. As such, rotation of the second articulation drive shaft 438 rotates the second drive gear 436, rotation of the second drive gear 436 rotates the second compound gear 448, and rotation of the second compound gear 448 rotates the second rack gear 440 that is surrounding the second articulation drive shaft 438. Further, the second rack gear 440 includes second rack gear teeth 452 that engage with the rack gearing 420 of the second rack 418A. Rotation of the second rack gear 440 therefore causes the second rack 418A to translate proximally and distally to move the second articulation bushing 428. With this configuration, rotation of the second input puck 404 in a clockwise direction (when viewed from a perspective showing the surface of the second input puck 404 that is configured to engage with the robotic arm 1100 (e.g., when viewing the outer-facing surface of second input puck 404)) can cause the second rack 418A to move distally and rotation of the second input puck 404 in a counter-clockwise direction can cause the second rack 418A to move proximally.

Referring again to the articulation bushings and racks, the first rack 414A can engage with the first articulation bushing 426 in a manner that enables proximal or distal movement of the first articulation bushing 426, while the first articulation bushing 426 remains able to rotate with the shaft 604. The first rack 414A includes a first bushing bearing surface 458 that abuts the first articulation bushing 426. The first articulation bushing 426 includes a first rack groove 480 around the perimeter of the bushing in which the first bushing bearing surface 458 extends. As the first articulation bushing 426 rotates, the first bushing bearing surface 458 can track through the first rack groove 480. As such, the first bushing bearing surface 458 can be semicircular. Similarly, the second rack 418A can engage with the second articulation bushing 428 in a manner that enables proximal or distal movement of the second articulation bushing 428, while the second articulation bushing 428 remains able to rotate with the shaft 604. The second rack 418A includes a second bushing bearing surface 460 that abuts the second articulation bushing 428. The second articulation bushing 428 includes a second rack groove 482 around the perimeter of the bushing in which the second bushing bearing surface 460 extends. As the second articulation bushing 428 rotates, the second bushing bearing surface 460 can track through the second rack groove 482. As such, the second bushing bearing surface 460 can be semicircular.

Referring now to FIGS. 15A, 15B, and 15C which show the actuation of the articulation subsystem 400 by movement of the first rack 414A and the second rack 418A. FIG. 15B shows an articulation subsystem 400 at a neutral, e.g., 0° state, of articulation. To move the first articulation bushing 426, the first rack gear 434 can rotate in a first angular direction, and the first rack gear teeth 446 move through the first rack gearing 416 of the first rack 414A. As shown in FIG. 15A, when the first rack gear 434 rotates and causes the first rack 414A to move proximally, the first articulation rod hook 405 is pulled proximally and causes the first articulation rod 406A to be pulled proximally. The second articulation rod 407A can be let out by the robotic arm to allow the end effector 150 to move in a first direction, in this example to the right (as shown in FIG. 12A).

FIG. 15C shows where the first rack 414A has moved distally and the second rack 418A has been moved proximally. Movement of the second rack 418A proximally causes the second articulation bushing 428 to translate proximally along the longitudinal axis 474 of the shaft 604. In turn, the second articulation rod 407A will translate proximally, thereby pivoting the distal channel retainer 408 such that the end effector 150 pivots in a second direction, in this example to the left (as shown in FIG. 12C (the end effector in FIGS. 12A-12C being rotated 180 degrees compared to FIGS. 15A-15C)). The first articulation rod 406A can be let out by the robotic arm to allow the end effector 150 to move in the second direction. In this example, the first articulation rod 406A and the second articulation rod 407A only cause actuation of the end effector 150 when caused to move proximally, thereby pulling the distal channel retainer 408 to pivot from left to right. In other words, the first articulation rod 406A and the second articulation rod 407A only cause the end effector 150 actuate when pulled in this example. In other examples, the first articulation rod 406A and the second articulation rod 407A can be configured to work together in a push/pull relationship. For example, as one of the first articulation rod 406A and the second articulation rod 407A is pulled in a proximal direction, the other of the first articulation rod 406A and the second articulation rod 407A can be pushed in a distal direction, thereby increasing the force applied to cause the articulation. That is the first articulation input puck 402 and the second articulation input puck 404 can be used together to cause the articulation system to actuate, thereby increasing the force applied to the articulation subsystem 400 for articulating the end effector 150.

In some examples, the articulation subsystem 400 described herein can achieve at least 60° of articulation in either direction, for example ±5°, ±10°, ±15°, ±20°, ±25°, ±30°, ±35°, ±40°, ±45°, ±50°, ±55°, and ±60°, or any intervening degree of articulation back and forth. It will be noted that the joint 160 shown in FIG. 12B that holds the end effector 150 to the shaft 604 is exposed for visualization. The joint 160 can be concealed by a flexible sheath 174 to alleviate pinch points. The joint 160 described herein can include multiple articulation links that connect the closure tube 212 to the closure ring 226. This linking system can be a boss/hole configuration that provides a pinned joint. The exterior closure system can consist of the closure tube 212 pushing distally forward on the two articulation links of the joint 160, which in turn push on the closure ring 226.

Turning now to FIGS. 16A, 16B, 16C, 16D, 16E and 16F, an alternative example articulation subsystem 400 is herein described. As shown, the articulation subsystem 400 can include a first inboard rack 414B and a second inboard rack 418B. For example, the first inboard rack 414B can be positioned at least partially between the first rack gear 434 and the rotatable shaft 604 and the second inboard rack 418B can be positioned at least partially between the second rack gear 440 and the rotatable shaft 604. In this way, the articulation subsystem 400 will have a more compact layout and the forces applied by the first inboard rack 414B and the second inboard rack 418B can be distributed closer to the longitudinal axis, thereby reducing torque forces on the first inboard rack 414B and the second inboard rack 418B.

The first inboard rack 414B and the second inboard rack 418B can each be pushed or pulled together in a push/pull relationship. For example, if the first inboard rack 414B and the second inboard rack 418B are moved axially toward each other, the end effector 150 will articulate in a first direction (e.g., to the right). If the first inboard rack 414B and the second inboard rack 418B are moved axially away from each other, the end effector will articulate in a second direction (e.g., to the left). In this way, forces from the first articulation input puck 402 and the second articulation input puck 404 can work together to cause the end effector 150 to articulate in a first or a second direction.

Figure 16A:
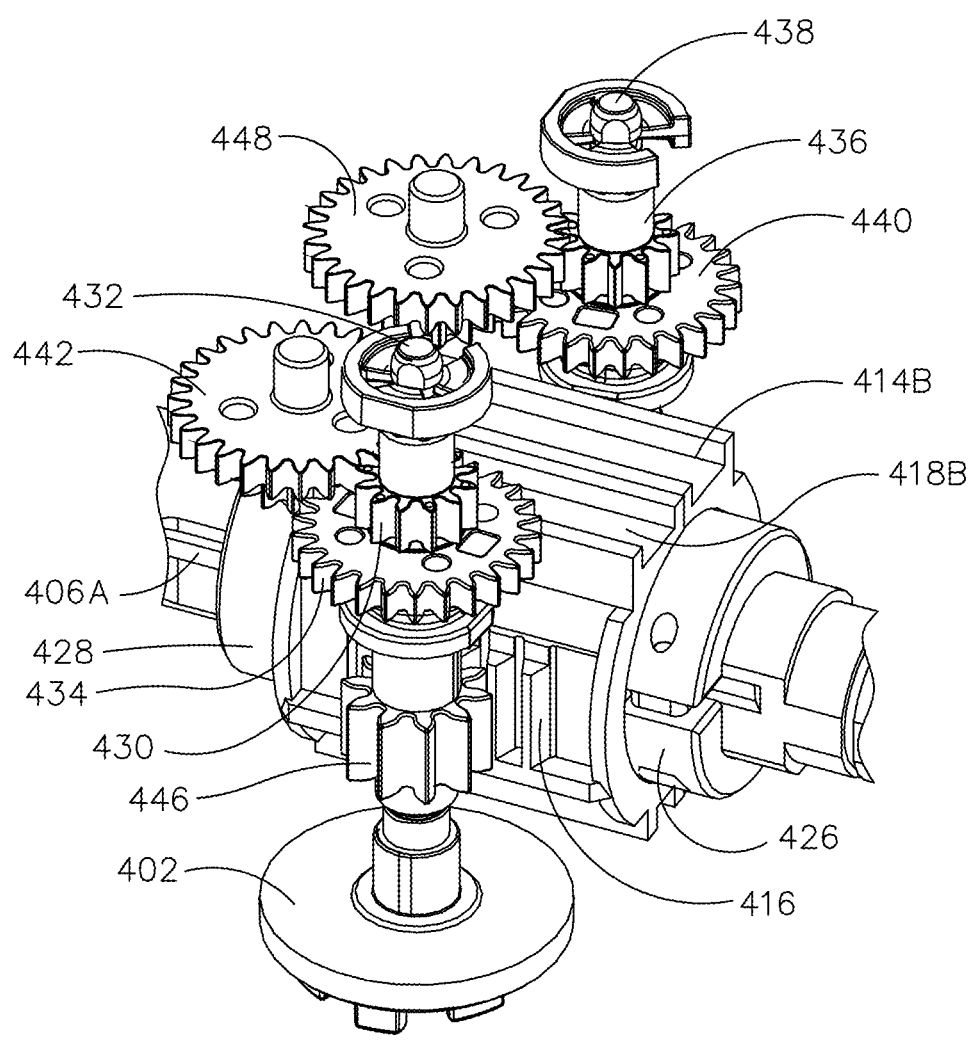
FIG. 16A is a detail view of an alternate articulation subsystem, according to aspects of the present disclosure.
Figure 16B:
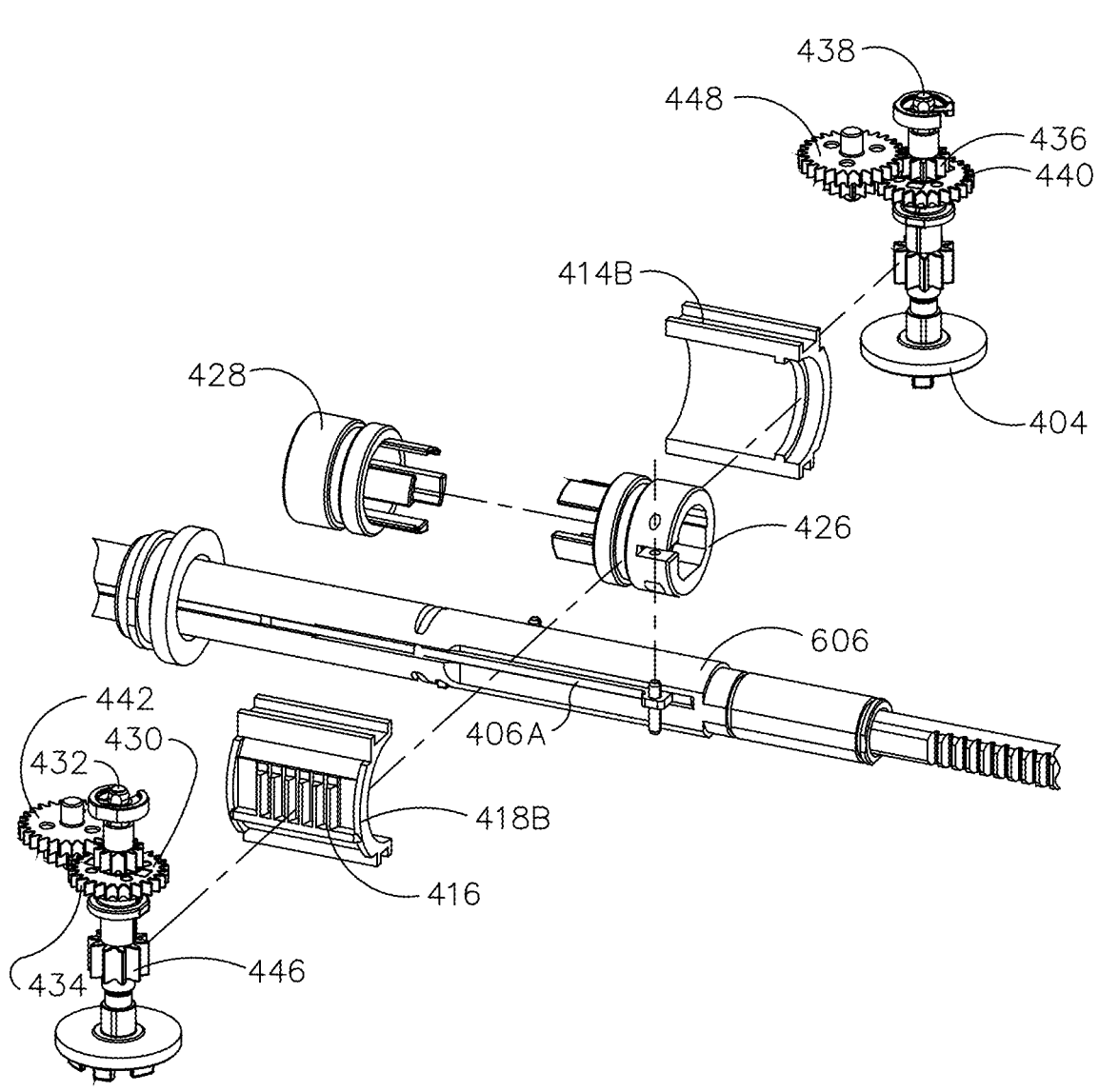
FIG. 16B is an exploded view of the alternate articulation subsystem of FIG. 16A, according to aspects of the present disclosure.
Figure 16C:
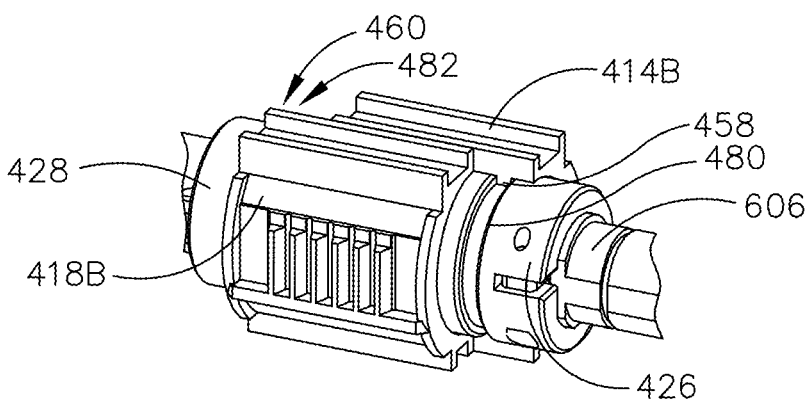
FIG. 16C is a detail view of articulation racks of the alternate articulation subsystem of FIG. 16A, according to aspects of the present disclosure.
Figure 16D:
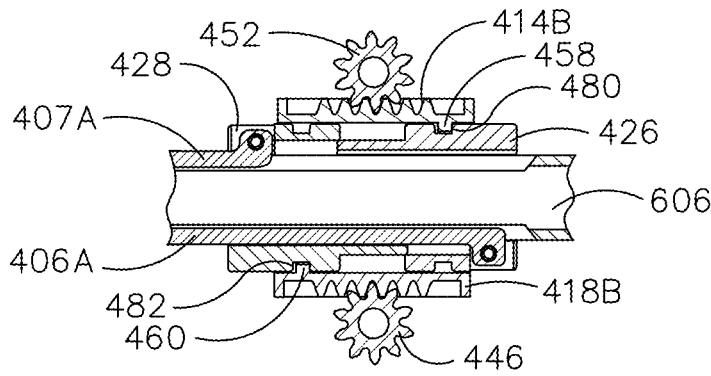
FIG. 16D is a section view of the alternate articulation subsystem taken horizontally along the longitudinal axis, according to aspects of the present disclosure.

Similar to the first rack 414A and the second rack 418, the first inboard rack 414B and the second inboard rack 418B can be configured to cause the first articulation rod 406A and the second articulation rod 407A to move proximally and distally via a first articulation bushing 426 and a second articulation bushing 428. Because the first inboard rack 414B and the second inboard rack 418B are positioned at least partially around the rotatable shaft 604 adjacent the first articulation bushing 426 and the second articulation bushing 428, the first inboard rack 414B and the second inboard rack 418B can push on the first articulation bushing 426 and the second articulation bushing 428, respectively, without the need for a portion of the racks to extend outwardly and engage with the bushings. As shown in FIGS. 16C and 16D, similar to the first rack 414 and the first articulation bushing 426, the first inboard rack 414B includes a first bushing bearing surface 458 that engages with a first rack groove 480. Similarly, the second inboard rack 418B includes a second bushing bearing surface 460 that engages with the second rack groove 482. In this way, the first inboard rack 414B and the second inboard rack 418B can be configured to move the first articulation bushing 426 and the second articulation bushing 428 proximally and distally but remain rotationally independent of the first articulation bushing 426 and a second articulation bushing 428.

Figure 16E:
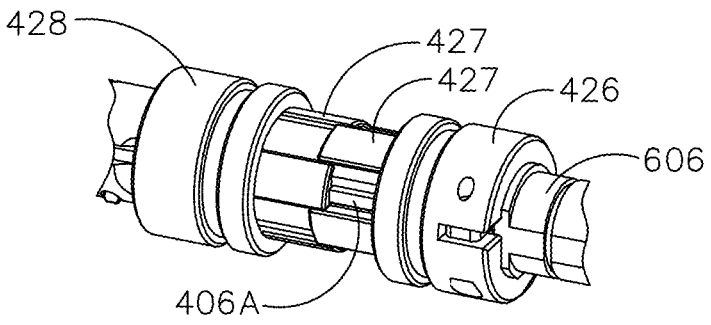
FIG. 16E is a detail view of articulation bushings of the alternate articulation subsystem, according to aspects of the present disclosure.

As shown in FIG. 16E, the first articulation bushing 426 and the second articulation bushing 428 can each include one or more bushing extensions 427 that protrude from the first articulation bushing 426 and the second articulation bushing 428 in a direction along the longitudinal axis. In this way, the bushing extensions 427 can help to prevent the first articulation bushing 426 and the second articulation bushing 428 from binding when being pushed or pulled proximally or distally.

Figure 16F:
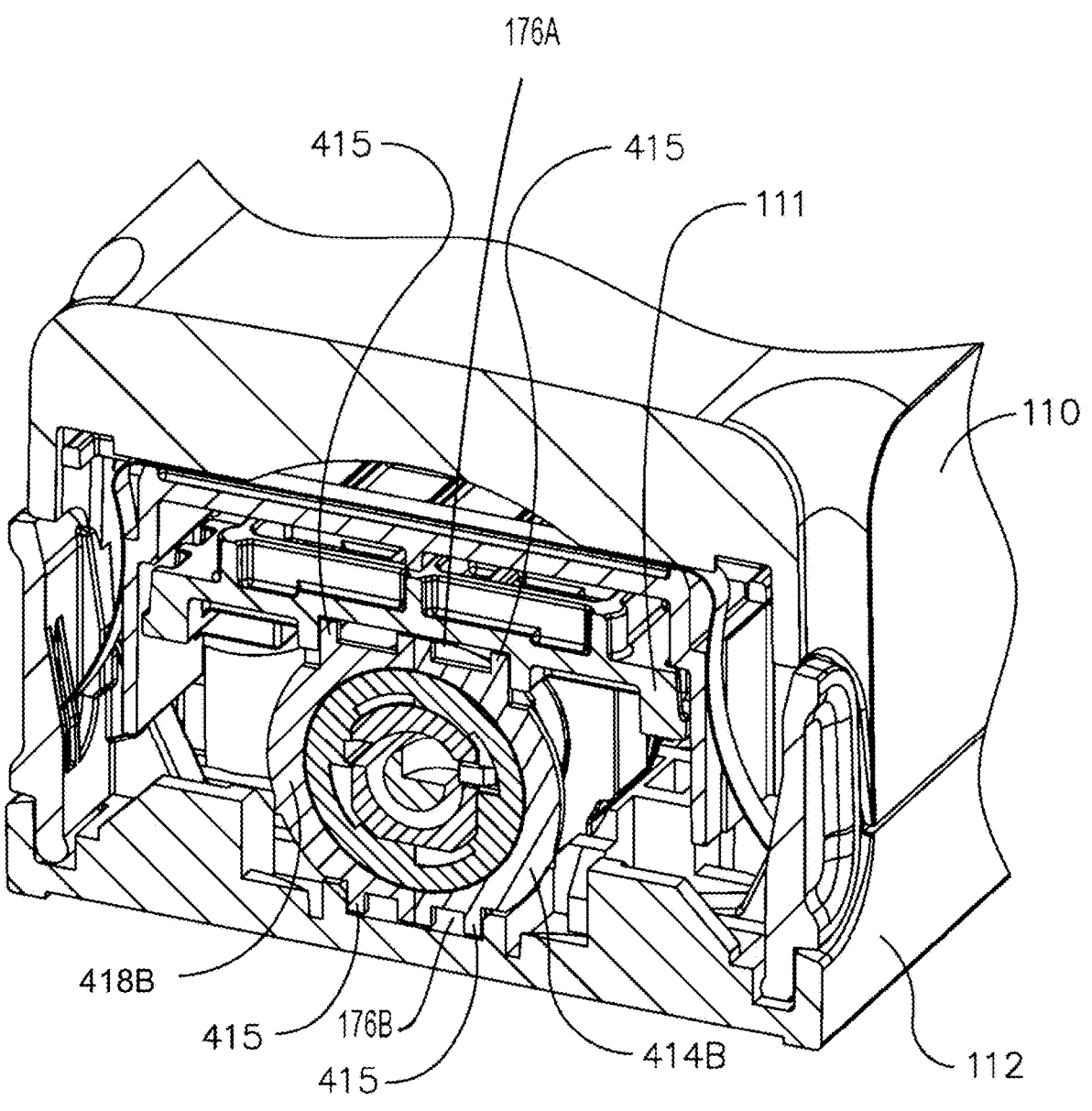
FIG. 16F is a detail view of the alternate articulation subsystem contacting a housing of the surgical instrument, according to aspects of the present disclosure.

As shown in FIG. 16F, the first inboard rack 414B and the second inboard rack 418B can each have a housing track surface 415 that moves axially within a corresponding track 176B in the first portion 112 of the housing 102 and a track 176A of the intermediate housing 111, thereby enabling the first inboard rack 414B to slide axially but not rotationally. In other words, the housing track surfaces 415 of the first inboard rack 414B and the second inboard rack 418B are configured to slide along the tracks 176A, 17B of the first portion 112 of the housing 102 and the intermediate housing 111 disposed in the housing 102. In this way, any rotational force applied to the first inboard rack 414B and the second inboard rack 418B by the roll subsystem 600 will not cause the first inboard rack 414B and the second inboard rack 418B to rotate within the housing 102.

Turning now to FIGS. 17A, 17B, 17C, 17D, 17E, 17F, and 17G, yet another alternate example of the articulation subsystem 400 will be shown and described. As shown, the articulation subsystem 400 can include a single inboard rack 414C that extends around the rotatable shaft 604. The first tube drive teeth 446 can engage with the single inboard rack 414C on a first side and the second tube drive teeth 452 can engage with the single inboard rack 414C on a second side. That is, the first tube drive teeth 446 and the second tube drive teeth 452 can engage the singe inboard rack 414C together. The single inboard rack 414C can be engaged with a single articulation bushing 429 that is coupled to a single articulation rod 403. That is, compared to the previous examples shown and described herein, the example articulation subsystem 400 shown in FIGS. 17A-17G can include a single articulation rod 403 that can be both pulled and pushed by a single articulation bushing 429 and a single inboard rack 414C.

Figure 17A:
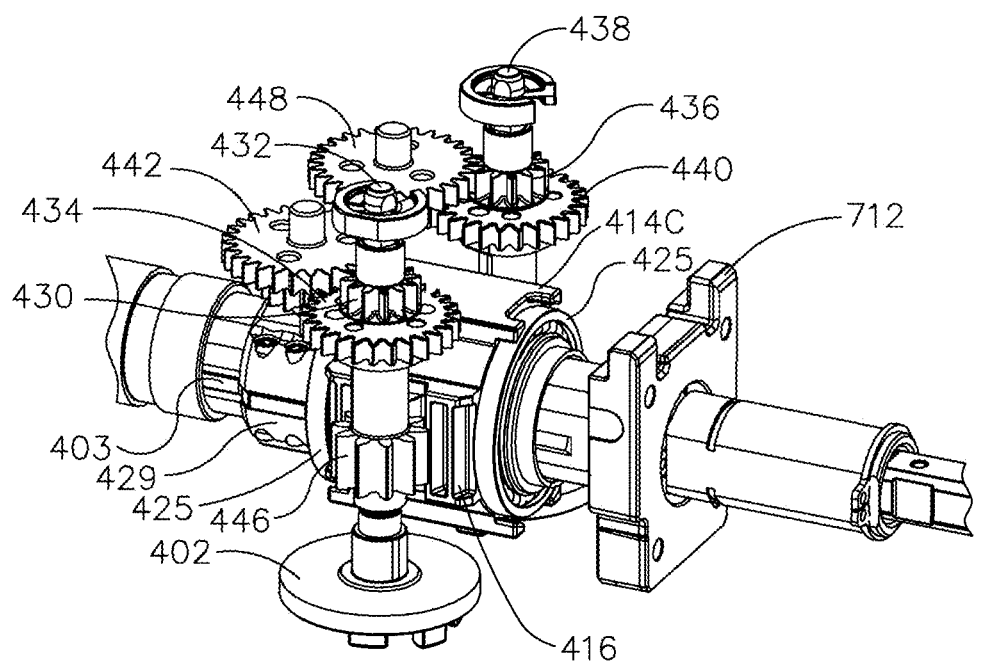
FIG. 17A is a detail view of another alternative articulation subsystem, according to aspects of the present disclosure.
Figure 17B:
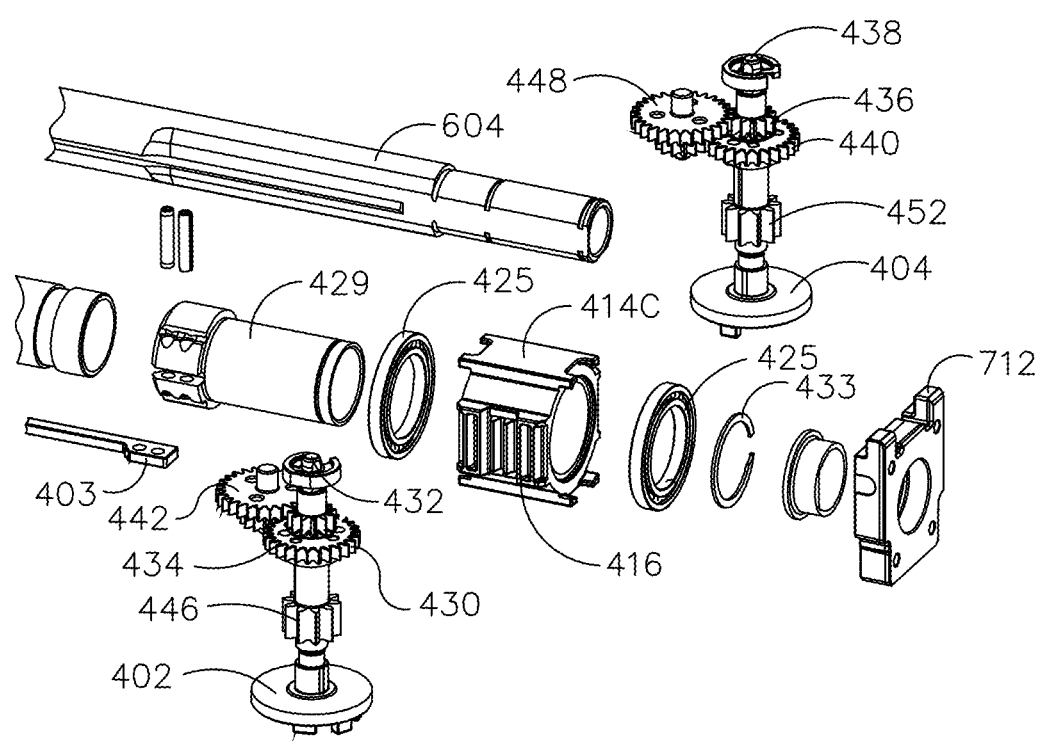
FIG. 17B is an exploded view of the other alternative articulation subsystem of FIG. 17A, according to aspects of the present disclosure.
Figure 17C:
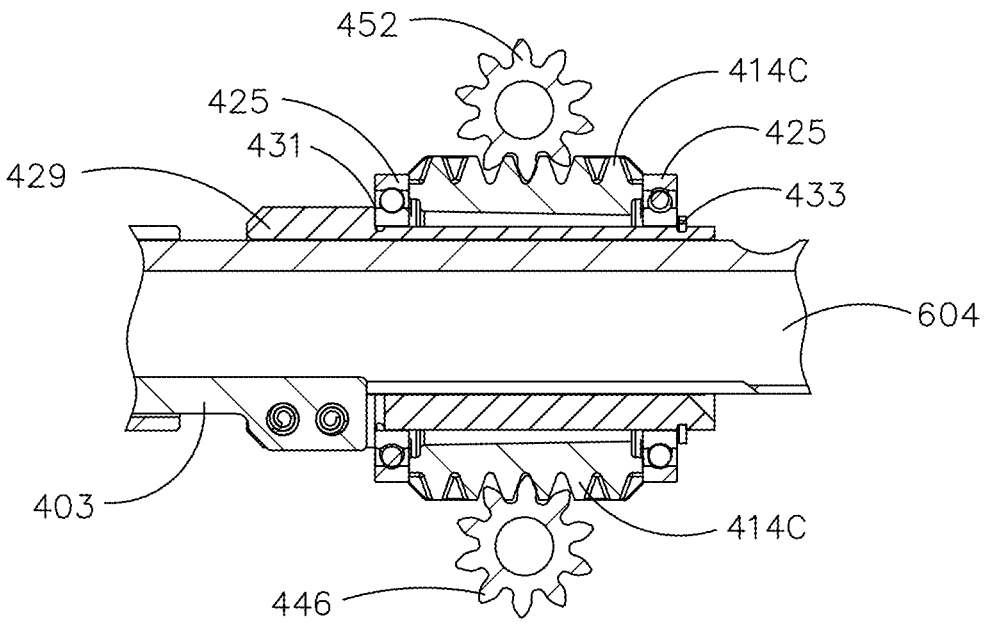
FIG. 17C is a section view of the other alternative articulation subsystem of FIG. 17A taken horizontally along the longitudinal axis, according to aspects of the present disclosure.
Figure 17D:
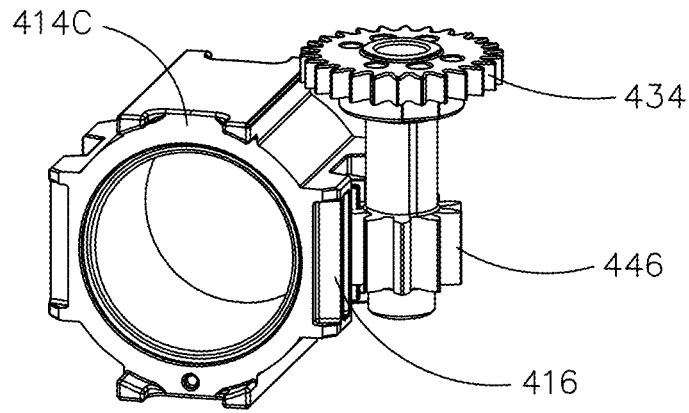
FIG. 17D is a detail view of an articulation rack and drive teeth of the other alternative articulation subsystem, according to aspects of the present disclosure.
Figure 17E:
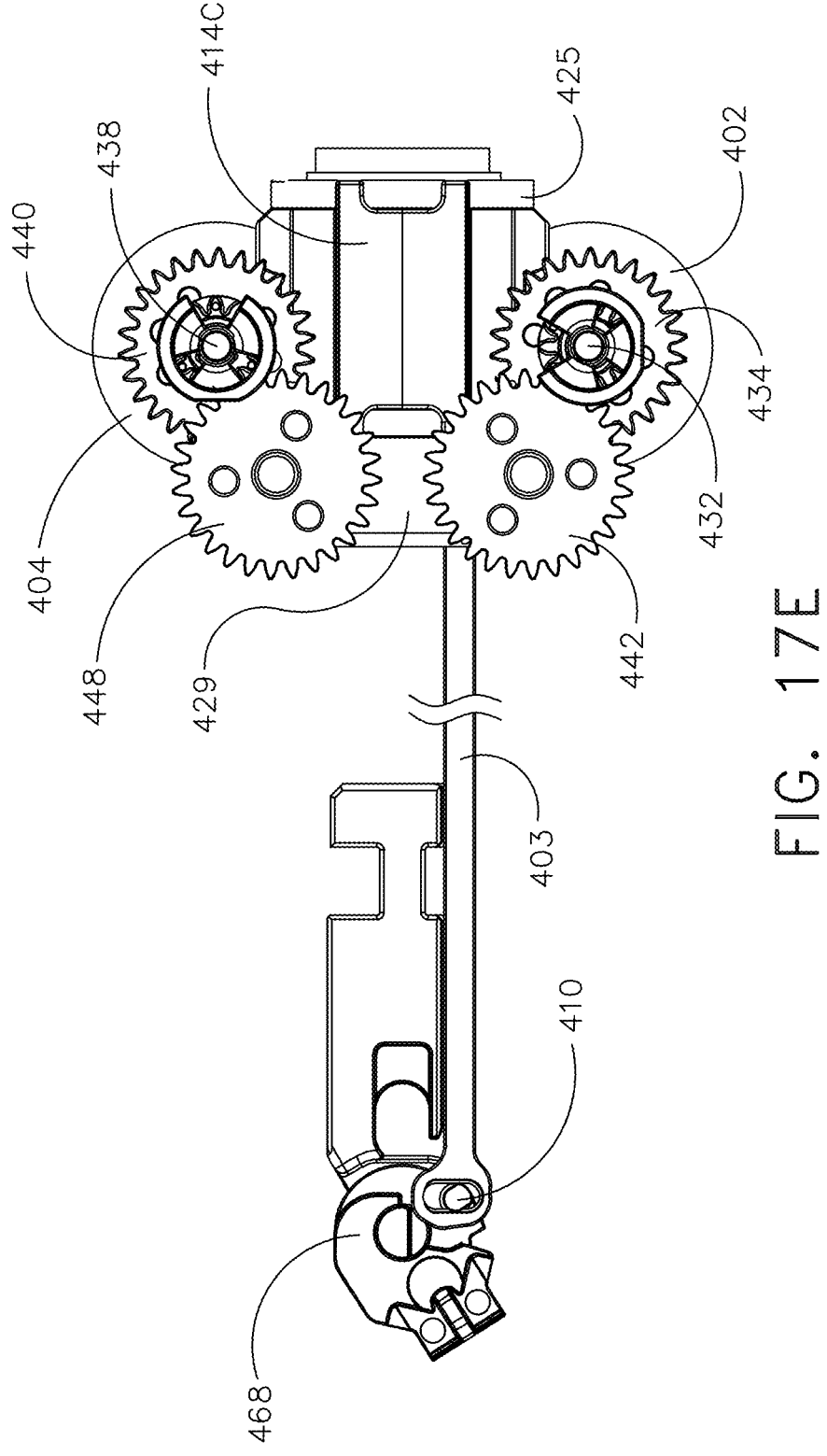
FIG. 17E is a top perspective view of the other alternative articulation subsystem of FIG. 17A, according to aspects of the present disclosure.

As shown in FIG. 17C, the single inboard rack 414C is separated from the single articulation bushing 429 by one or more bearings 425. The a first bearing 425 is constrained distally by a flange 431 and a second bearing 425 is constrained proximally by a locking ring 433. Constrained as such, movement of the single inboard rack 414C causes the single articulation bushing 420 to move axially. By including the bearings 425, the single inboard rack 414C can be rotationally independent of the single articulation bushing 429 but still be configured to cause the single articulation bushing 429 (and, consequently, the single articulation rod 403) to translate proximally and distally. Furthermore, because the first tube drive teeth 446 and the second tube drive teeth 452 engage the single inboard rack 414C together, it will be appreciated that forces from the first articulation input puck 402 and the second articulation input puck 404 can work together to cause the end effector 150 to translate in a first and in a second direction.

Figure 17F:
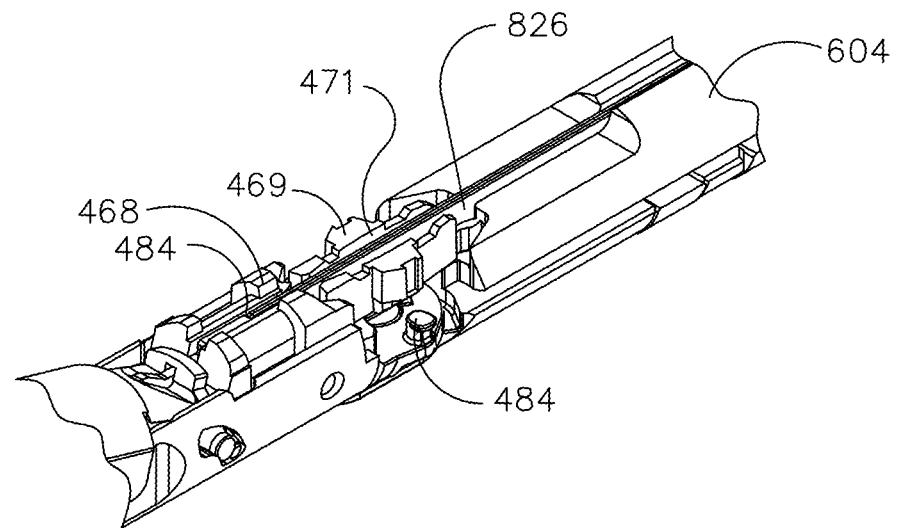
FIGS. 17F and 17G are detail views of an articulation joint of the articulation subsystem, according to aspects of the present disclosure.
Figure 17G:
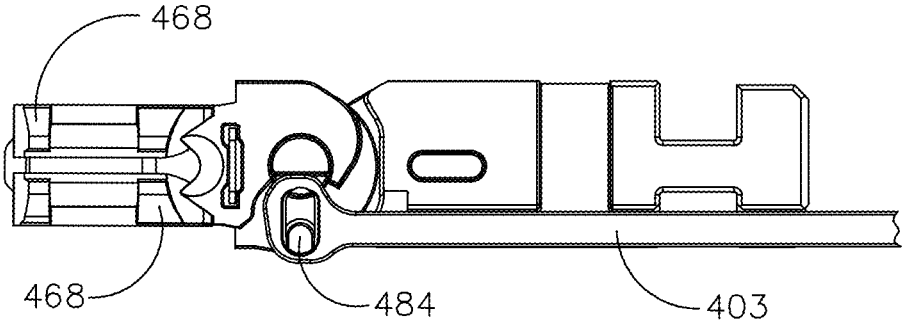

Turning now to FIGS. 17F and 17G, the articulation subsystem 400 can include a knife guide 469 that can be positioned between the attachment end 468 and the proximal end of the shaft 604. The knife guide 469 can include a band slot 471 similar to the band slot 484 of the attachment end 468 that can help to guide the bands 826 that translate proximally and distally. The knife guide 469 can help to prevent the bands 826 from buckling, twisting, or otherwise becoming bound when translating proximally or distally, thereby helping to ensure the knife 166 can also more proximally and distally.

As shown in FIGS. 17F and 17G, the articulation subsystem 400 can include an articulation rod post 484 that can receive the single articulation rod 403, The articulation rod post 484 can couple the single articulation rod 403 to the attachment end 468 to cause the end effector 150 to articulate left and right when the single articulation rod 403 is moved proximally and distally.

Roll Subsystem

Figure 18A:
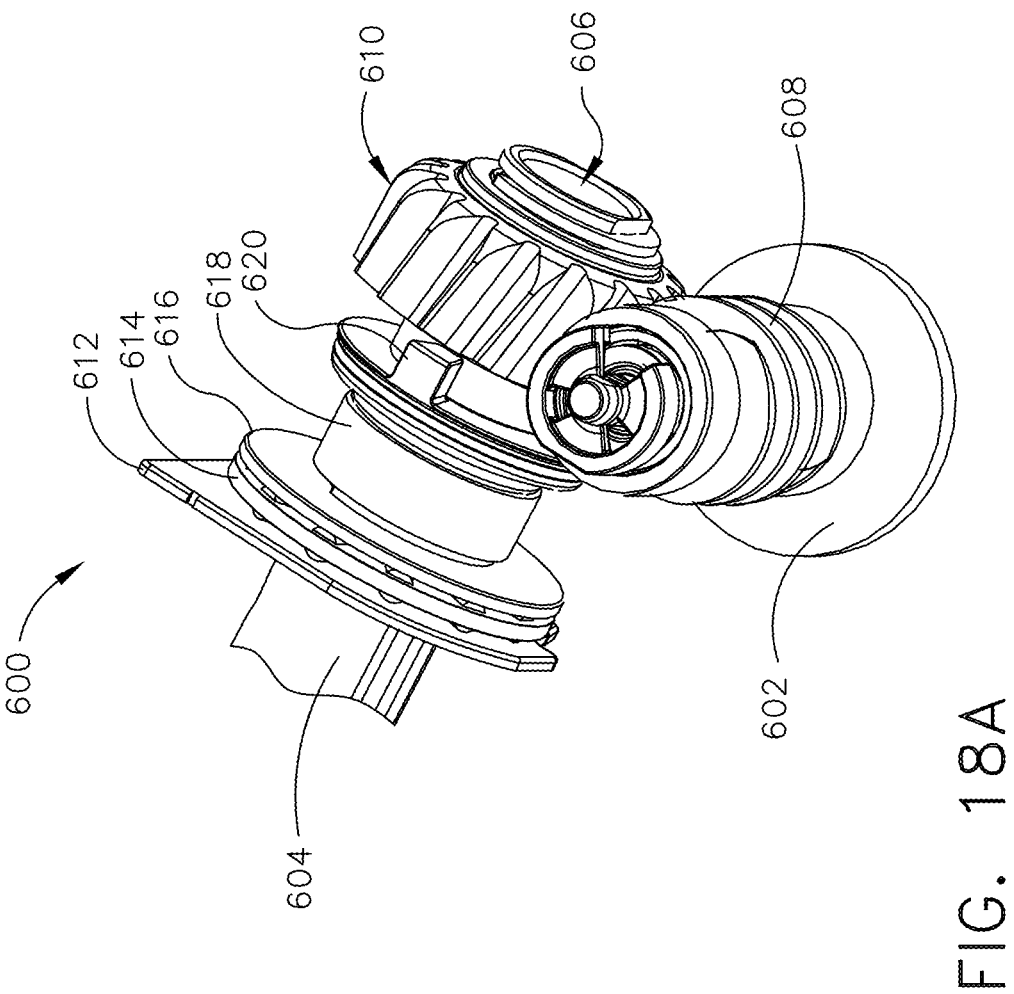
FIG. 18A is a detail view of components of a roll subsystem, according to aspects of the present disclosure.
Figure 18B:
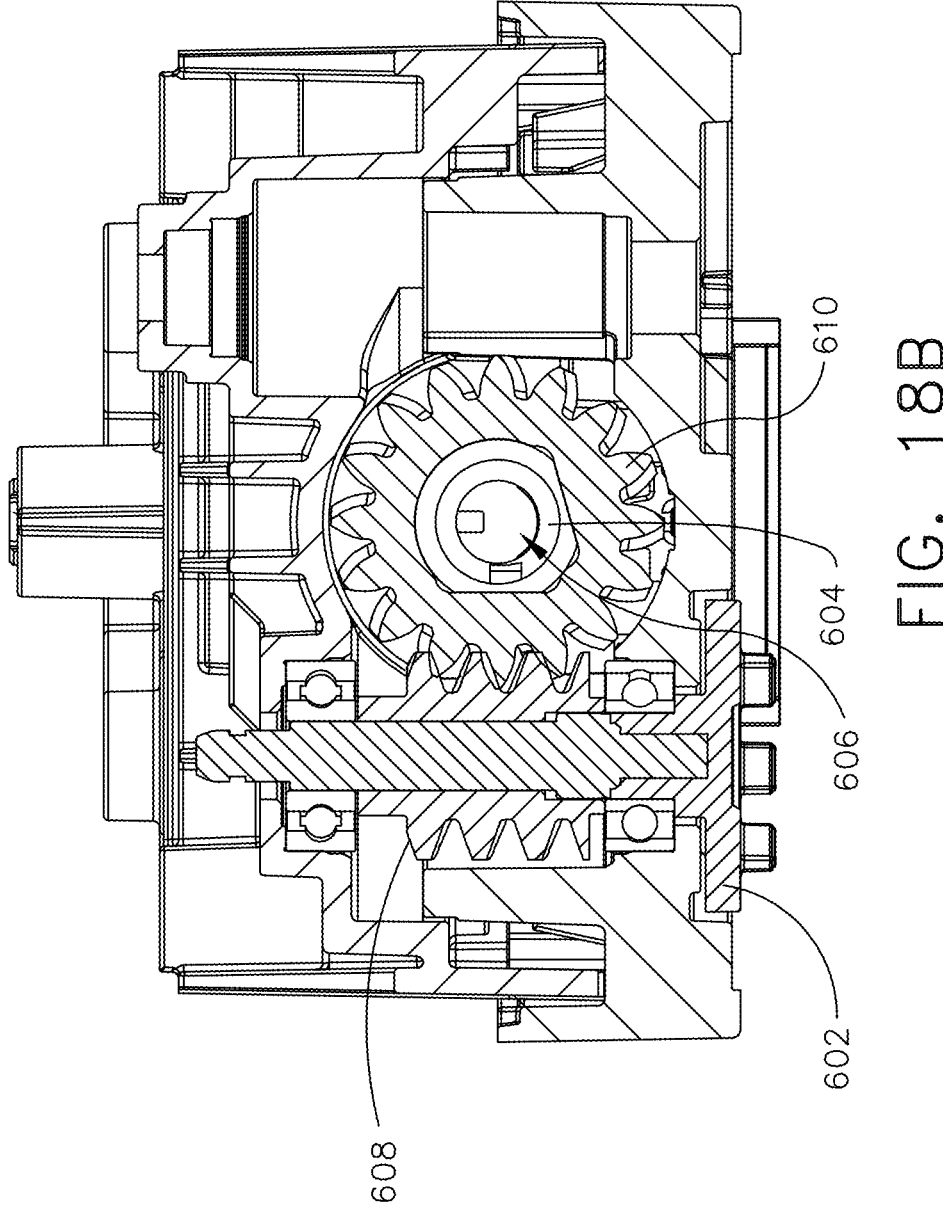
FIG. 18B is a cross-sectional view of components of the roll subsystem, according to aspects of the present disclosure.

The surgical instrument 100 includes a roll subsystem 600. Detailed views of the proximal portions of an example roll subsystem 600 are provided in FIGS. 18A, 18B, 18C, 18D, and 18E. Referring specifically to FIGS. 18A and 18B, the roll subsystem 600 includes a series of gears that allow the shaft 604 to rotate distally along a longitudinal axis 474 of the surgical instrument 100. The shaft 604 can be directly connected to the end effector 150, and therefore rolling of the shaft 604 enables the end effector 150 to roll a single articulation plane to any orthogonal position. The shaft 604 includes a shaft lumen 606 extending therethrough, and distal portions of a transection subsystem 800 extend through the shaft lumen 606. The transection subsystem 800 is described in greater detail below.

The roll subsystem 600 includes a roll input puck 602 that is engageable with a corresponding rotatable robotic output. The roll input puck 602 can be rotationally engaged with a worm gear 608 extending therefrom, such that rotation of the roll input puck 602 turns the worm gear 608 either clockwise or counter-clockwise. Since the roll input puck 602 is positioned perpendicular to the length of the surgical instrument 100, and therefore perpendicular to the shaft 604, the roll subsystem 600 includes a worm follower 610 that is engaged with the worm gear 608. The worm follower 610 can be coupled to the shaft 604, allowing rotation of the shaft 604. To keep the worm follower 610 positioned at the correct location relative to the worm gear 608, the roll subsystem 600 includes a stabilization plate 612 that surrounds the shaft 604 distal to the worm follower 610. The stabilization plate 612 can be positioned within a corresponding slot within the outer housing 102 to prevent the stabilization plate 612 from sliding axially along the shaft 604, while also providing the shaft 604 lateral alignment within the housing 102. The roll subsystem 600 can also include a roll bearing 614 and a roll bearing plate 616, the roll bearing 614 being positioned between the stabilization plate 612 and the roll bearing plate 616.

In some examples, the roll subsystem 600 includes a roll stop bushing 618 engaged with the rotatable shaft 604. The roll stop bushing 618 can be coupled to the worm follower 610 and/or shaft 604 and provide feedback on positioning of the rotatable shaft 604. For example, the roll stop bushing 618 includes a stop 620 positioned thereon that can contact a housing tab 626 positioned on the outer housing 102. The roll subsystem 600 can roll the shaft 604 to a first position where the roll stop bushing 618 contacts the housing tab 626 at a first side, and then roll the shaft 604 to a second position where the roll stop bushing 618 contacts the housing tab 626 at a second, opposite side. The robotic output that actuates the roll subsystem 600 can use the hard stops at the housing tab 626 to determine a baseline, or 0°, rotation for the shaft 604. This example can provide the shaft 604 greater than 300° of rotation, for example greater than 305°, greater than 310°, greater than 315°, greater than 320°, greater than 325°, greater than 330°, greater than 335°, greater than 340°, greater than 345°, greater than 350°, greater than 355° of rotation, or more.

In some examples, the roll subsystem 600 does not include a housing tab 626 and allows the roll subsystem 600 to continue to roll indefinitely. In this configuration, the control device of the robotic arm 1100 can be programmed to determine a home position and can be configured to track and accurately determine the position of the roll subsystem 600 and/or the end effector 150 at any given point of rotation.

Figures 18C, 18D, 18E:
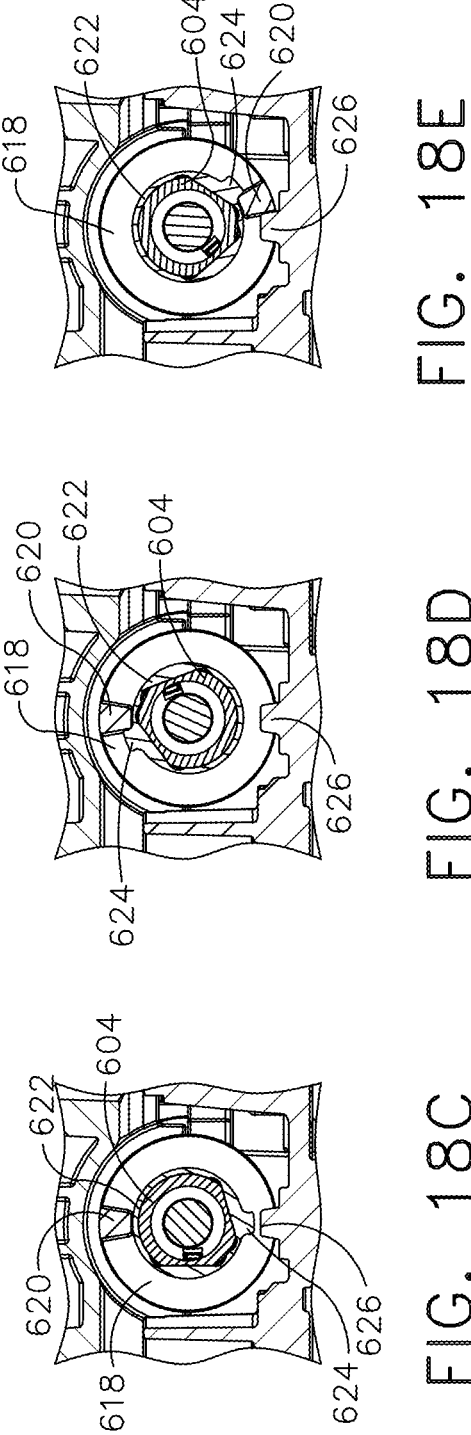
FIGS. 18C, 18D, and 18E are end views of bushings for a roll system, according to aspects of the present disclosure.

In some examples, the roll subsystem 600 can also include a follower bushing 622 (as shown in FIGS. 18C, 18D, and 18E) having a follower bushing stop 624 extending therefrom. In this example, the follower bushing 622 can be positioned between the shaft 604 and the roll stop bushing 618. The shaft 604 and follower bushing 622 can be directly coupled to each other, and the roll stop bushing 618 and the follower bushing 622 can rotate relative to each other. The roll subsystem 600 can roll the shaft 604 to a first position where the roll stop bushing 618 contacts the housing tab

626, and the follower bushing 622 contacts the roll stop bushing 618 at a first side (see FIG. 18C). The roll subsystem 600 can then rotate the shaft 604 until the follower bushing 622 contacts the roll stop bushing 618 at the other side (see FIG. 18D), and then continue rotating by pushing the roll stop bushing 618 circumferentially until the roll stop bushing 618 contacts the housing tab 626 and the follower bushing 622 contacts the roll stop bushing 618 at a second, opposite side (see FIG. 18E). This example using the follower bushing 622 can provide a greater degree of rotation, for example greater than 360° of rotation, or in some instances about 320° of rotation in either direction (e.g., 640° in total). Referring briefly to FIG. 10, which shows distal portions of the roll subsystem 600, the view shows how the rod groove 478 of the shaft 604 can extend along the length of the shaft 604. The first articulation rod 406A can extend through the rod groove 478 of the shaft 604, and rotation of the shaft 604 by the roll subsystem 600 can therefore rotate the articulation rod 406A.

Figure 19B:
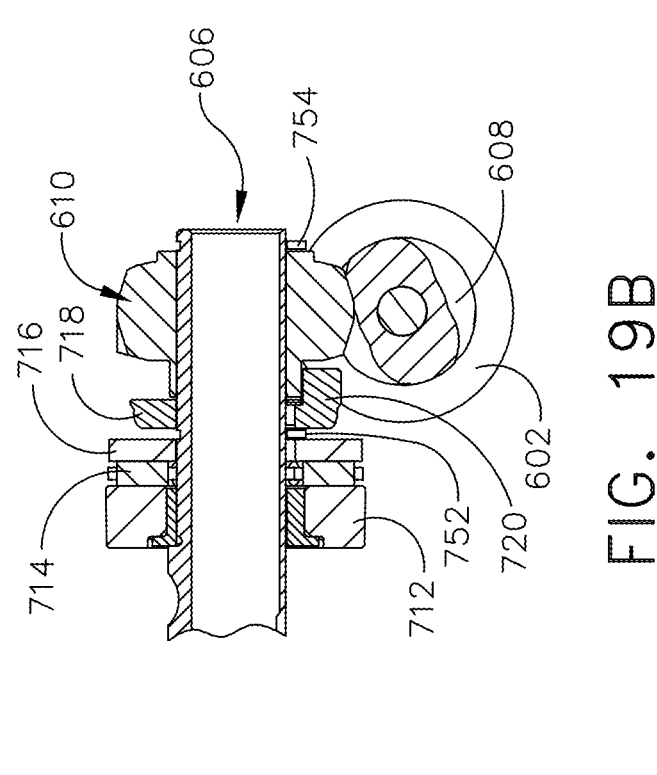
FIGS. 19A and 19B show alternative components of a roll subsystem, according to aspects of the present disclosure.
Figure 19A:
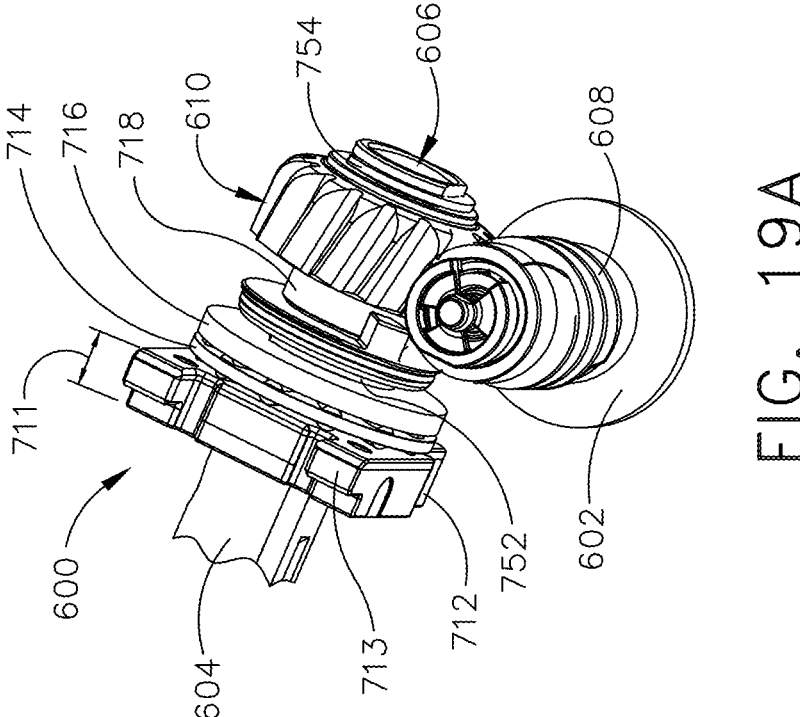

FIGS. 19A and 19B show alternative components of a roll subsystem 600 to the one shown in FIGS. 18A-18E, according to aspects of the present disclosure. FIG. 19A is a perspective view of the components of the roll subsystem 600. In the embodiment shown, the stabilization plate 612 comprises a thick thrust block 712. The thrust block 712 is positioned near the proximal end of the shaft 604 so as to counteract axial forces on the shaft 604 caused by distal movement of the closure tube 212 (see FIG. 1). Providing a more robust thrust block 712, including a thickness 711 greater than 1.0 cm, or greater than 1.5 cm, can provide better loading scenarios (to stop deflection) and can better share the load with the housing 102. The thrust block 712 includes supports 713 that engage with a buttress 178, such as the buttress 178 shown in FIG. 19I. As shown in FIG. 19I, the buttress 178 sits within the housing 102 and distributes loads applied to the buttress 178 from the thrust block 712 (as well as other components) to the housing 102. FIG. 19A shows additional components that can be included in the alternative design, including a roll bearing 714, which can be substantially similar to the roll bearing 614 in 18A, and a roll bearing plate 716, which can be substantially similar to the roll bearing plate 616 in FIG. 18A (in FIG. 19A, the bearing plate 716 is thicker than the roll bearing plate 616 to further add to the robustness and load sharing at this component). FIG. 19A also shows a roll stop bushing 718, which can be substantially similar to roll stop bushing 618. FIG. 19B is a top, cross-sectional view of the components of the roll subsystem 600. The roll subsystem 600 includes a first locking ring 752 and a second locking ring 754. The locking rings 752, 754 can be positioned such that they secure the worm follower 610 and the roll stop bushing 718 together. The stop 730 of the roll stop bushing 718 is also shown; the stop 720 can be substantially similar to the stop 620 described above.

Figures 19C, 19D, 19E, 19F:
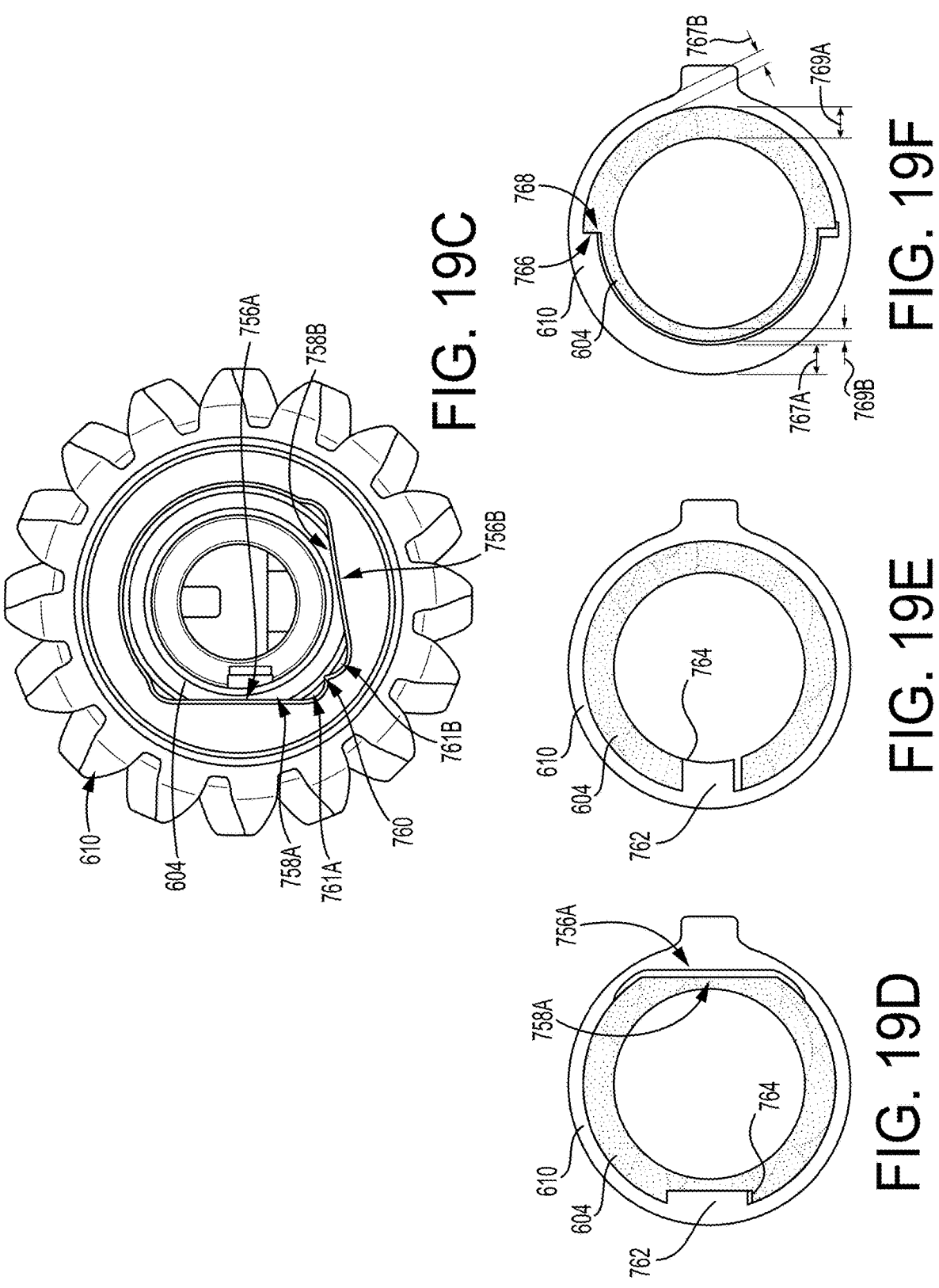
FIGS. 19C-19F provide examples of anti-backlash features for a worm follower engaged with a rotatable shaft, according to aspects of the present disclosure.

Referring to FIG. 19C for reference, as shown, the inside of the worm follower 610 may not be entirely round and, similarly, the outside surface of the shaft 604 may not be entirely round. Instead, the worm follower 610 and the shaft 604 can have corresponding anti-backlash features. It is desirable to reduce backlash in the gearing of a surgical instrument 100 to improve accuracy and to ensure proper calibration. For instance, a robot can home and/or calibrate roll by rolling the shaft 604 from one mechanical calibration position to another mechanical calibration position (see FIGS. 18C-18E for a discussion of rotational constraints for the roll subsystem 600). Therefore, backlash reduction can help to ensure accurate calibration. The implementations shown in FIGS. 19C-19F provide examples of such anti-backlash features.

FIG. 19C is a detailed view of the worm follower 610. Here, the inside area of the worm follower 610 (i.e., the portion engaged with the shaft 604) includes one or more gear flats 756. A gear flat 756 can be used to ensure that the worm follower 610 constrains the shaft 604 so that they rotate together. The one or more gear flats 756 are positioned to abut and/or contact one or more corresponding shaft flats 758 on the exterior surface of shaft 604. In the example shown, the worm follower 610 comprises a first gear flat 756A and a second gear flat 756B, and the rotatable shaft 604 comprises (i) a first shaft flat 758A positioned to correspond to the first gear flat 756A and (ii) a second shaft flat 758A positioned to correspond to the second gear flat 756B. Having more than one flat can further limit backlash between the two components. In certain implementation, the first gear flat 756A can coincide with the portion of the shaft 604 that houses the rod groove 478 (see, e.g., FIG. 10).

The one or more gear flats 756 may be milled, broached, or formed into the worm follower 610 and, as such, tight corners between the flat and curved section may not be possible or may not be desired, for instance because abrupt corners could be a location for stress fractures. Accordingly, the transitions between the one or more gear flats 756 and the curved section to provide gaps between the worm follower 610 and the shaft 604 at certain positions. Two such gaps are shown in FIG. 19C and are labeled as first gap 761A and second gap 761B. A first end of the first gear flat 756A is rounded and inwardly turned so as to come to a singular point 760. A first end of the second gear flat 756B is rounded and inwardly turned so as to come to the singular point 760. A portion of the worm follower 610 between the first gear flat 756A and the singular point 760 is separated from the rotatable shaft 604 by the aforementioned first gap 761A. A portion of the worm follower 610 between the second gear flat 756B and the singular point 760 is separated from the rotatable shaft 604 by the second gap 761B. The singular point 760 contacts the rotatable shaft 604 to provide the circumferential control of the shaft 604 within the worm follower 610.

FIGS. 19D-19F show additional or alternative anti-backlash features for the worm follower 610 and shaft 604. In FIG. 19D, the worm follower 610 includes a key 762 that engages with a keyway 734 in the shaft 604. Alternatively, the shaft 604 could include the key and the worm follower 610 the keyway. In some examples, the key/keyway could be combined with one of the other anti-backlash features, such as first shaft flat 758A and first gear flat 756A, as shown. In FIG. 19E, the example shown also includes a key 762 and a keyway 734, but the keyway 734 extends entirely through the wall of the shaft 604. In FIG. 19F, the worm follower 610 has different wall thickness, as measured to the inside surface of the worm follower 610 that contacts the shaft 604. The worm follower 610 has a first portion with a first wall thickness 767A and a second portion with a second wall thickness 767B, the first wall thickness 767A being thicker than the second wall thickness 767B. This change in interior wall geometry thereby forms a gear step 766. Similarly, the rotatable shaft 604 has a first portion with a first wall thickness 769A and a second portion with a second wall thickness 769B, the first wall thickness 769A being thicker than the second wall thickness 769B. This change in the interior wall geometry of the shaft 604 thereby forms a shaft step 768. The gear step 766 is sized and positioned to engage with the shaft step 768 to reduce backlash as the worm gear 608 actuates the worm follower 610. It is also contemplated that the worm follower 610 and shaft 604 are inseparably connected, such as with a weld or adhesive, though manufacturing a connected embodiment may take additional steps in manufacturing.

Figure 19H:
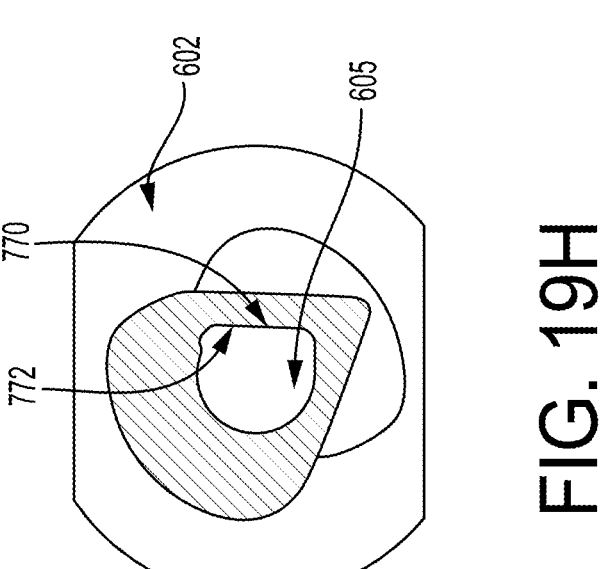
FIGS. 19G and 19H show example anti-backlash features for a worm gear, according to aspects of the present disclosure.
Figure 19G:
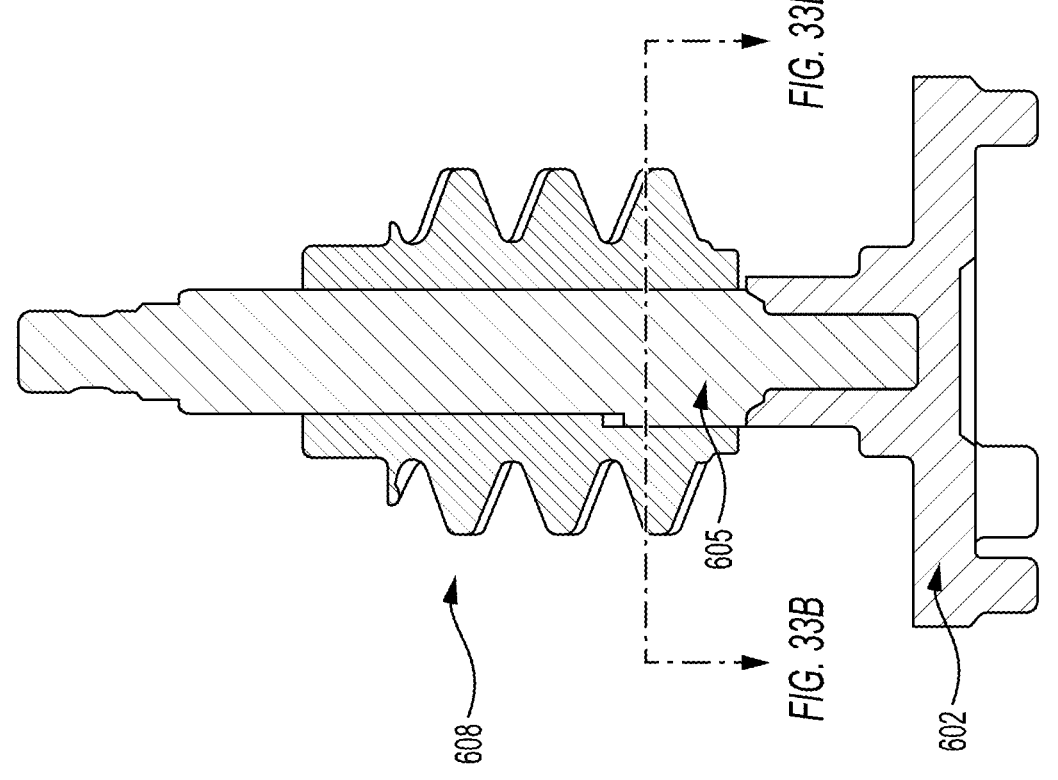
Figure 191:
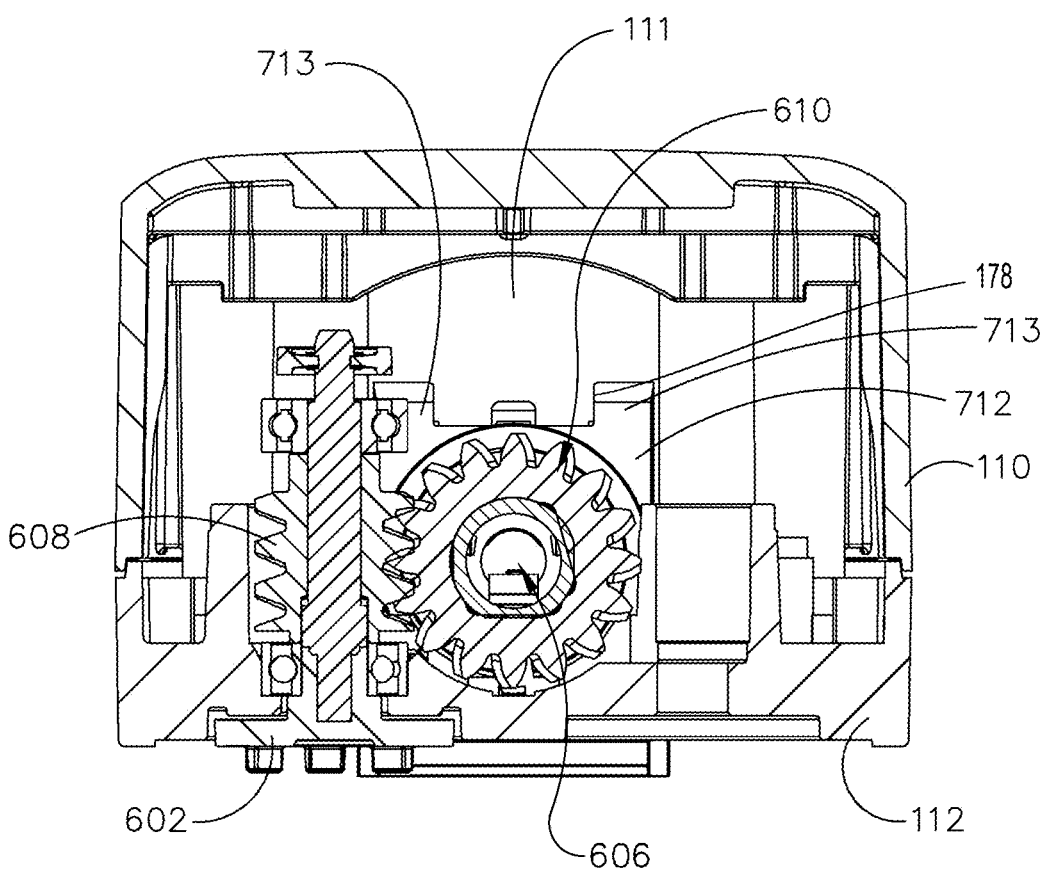

FIGS. 19G and 19H show example anti-backlash features for a worm gear 608, according to aspects of the present disclosure. The disclosure above discussed reducing backlash at the connection between the shaft 604 and worm follower 610, but another point of potential backlash in the roll subsystem 600 is where the roll input puck 602 and its respective input shaft 605 engages with the worm gear 608. FIG. 19G shows the placement of the input puck 602, input shaft 605, and worm gear 608, whereas the top FIG. 19H cross sectional view shows the example anti-backlash features. The input shaft 605 extends at least partially through the worm gear 608. The input shaft 605 includes a flat section 772 positioned to correspond to a worm drive flat 770 of the worm gear 608. This flat-on-flat feature is similar to the gear flats 756 and shaft flats 758 discussed with respect to FIG. 19C and helps to reduce backlash in the system.

Any of the closure subsystems 200, articulation subsystems 400, roll subsystems 600, or transection subsystems 800 described herein can be, respectively, substituted by or combined with any of the closure subsystems 200, articulation subsystems 400, roll subsystems 600, or transection subsystems 800 described in U.S. Provisional Application No. 63/514,972 or those described in U.S. Provisional Application No. 63/634,201, both of which are incorporated herein by reference in their entireties. Any of the end effectors 150 described herein can be substituted by or combined with any of the end effectors 150 described in U.S. Provisional Application No. 63/514,972 or those described in U.S. Provisional Application No. 63/634,201, both of which are incorporated herein by reference in their entireties.

Clauses

Examples of the present disclosure can be implemented by any of the following numbered clauses:

Clause 1: An articulation subsystem (400) for a surgical instrument (100) comprising: a rotatable shaft (604) having a longitudinal axis (474); a distal channel retainer (408) coupled to an end effector (150), the distal channel retainer (408) being pivotable about an articulation pivot point (466); an articulation bushing (426, 428) slidable between a proximal position and a distal position along the longitudinal axis (474) of the rotatable shaft (604); an articulation rod (406A, 407A, 406B, or 407B) extending distally from the articulation bushing (426) and coupled at a distal end (472) to the distal channel retainer (408); and a rack (414A, 418A, 414B, 418B, or 414C) movable with respect to the longitudinal axis (474) of the rotatable shaft (604), wherein movement of the rack (414) with respect to the longitudinal axis (474) imparts an axial force onto the articulation bushing (426) moving the articulation bushing (426) between the proximal position and the distal position, and wherein movement of the articulation bushing (426) between the distal position and the proximal position actuates the articulation rod (406A, 407A, 406B, or 407B) causing the distal channel retainer (408) to pivot about the articulation pivot point (466).

Clause 2: The articulation subsystem (400) according to Clause 1, wherein the articulation bushing (426) is rotationally independent of the rack (414A, 418A, 414B, 418B, or 414C).

Clause 3: The articulation subsystem (400) according to Clause 1 or Clause 2 further comprising a rack gear (434) engaged with the rack (414A, 418A, 414B, 418B, or 414C), rotation of the rack gear (434) moving the rack (414A, 418A, 414B, 418B, or 414C) with respect to the longitudinal axis (474).

Clause 4: The articulation subsystem (400) according to Clause 3 further comprising: an articulation input puck (402) engageable with an articulation robotic output; an articulation drive shaft (432) extending from the articulation input puck (402) and comprising a drive gear (430); and a compound gear (442) engaged with the drive gear (430) and the rack gear (434), wherein rotation of the articulation input puck (402) rotates the rack gear (434) moving the rack (414A, 418A, 414B, 418B, or 414C) with respect to the longitudinal axis (474).

Clause 5: The articulation subsystem (400) according to Clause 4, wherein the rack gear (434) is a tube gear, and the articulation drive shaft (432) is positioned within the rack gear (434).

Clause 6: The articulation subsystem (400) according to any of Clauses 3 to 5, wherein the rack (414A, 418A) is positioned at least partially on a side of the rack gear (434) opposite the rotatable shaft (604).

Clause 7: The articulation subsystem (400) according to any of Clauses 3 to 5, wherein the rack (414B, 418B, 414C) is positioned at least partially between the rack gear (434) and the rotatable shaft (604).

Clause 8: The articulation subsystem (400) according to any of Clauses 3 to 7, wherein the rack gear (434) is a first rack gear, the articulation subsystem further comprising: a second rack gear (440) engaged with the rack (414C), rotation of the first rack gear (434) and the second rack gear (440) together moving the rack (414C) with respect to the longitudinal axis (474).

Clause 9: The articulation subsystem (400) according to Clause 8, wherein the first rack gear (434) and the second rack gear (440) simultaneously rotate in opposite directions to cause the rack (414C) to move with respect to the longitudinal axis (474).

Clause 10: The articulation subsystem (400) according to any one of Clauses 1 to 9, wherein the articulation bushing is a first articulation bushing (426), the rack is a first rack (414A, 414B), and the articulation rod is a first articulation rod (406A, 406B), the articulation subsystem further comprising: a second articulation bushing (428) slidable between a second proximal position and a second distal position along the longitudinal axis (474) of the rotatable shaft (604); and a second rack (418A, 418B) movable with respect to the longitudinal axis (474) of the rotatable shaft (604), wherein movement of the second rack (418A, 418B) with respect to the longitudinal axis (474) imparts an axial force onto the second articulation bushing (428) to move the second articulation bushing (428) between the second proximal position and the second distal position, wherein movement of the second articulation bushing (428) between the second distal position and the second proximal position actuates a second articulation rod (406) causing the distal channel retainer (408) to pivot about the articulation pivot point (466).

Clause 11: The articulation subsystem (400) according to Clause 10, wherein movement of the first articulation bushing (426) from the distal position to the proximal position actuates the distal channel retainer (408) in a first direction, and wherein movement of the second articulation bushing (428) from the second distal position to the second proximal position actuates the distal channel retainer (408) in a second direction.

Clause 12: The articulation subsystem (400) according to Clause 10 or Clause 11 further comprising a second rack gear (440) engaged with the second rack (418A, 418B), rotation of the second rack gear (440) moving the second rack (418) with respect to the longitudinal axis (474).

Clause 13: The articulation subsystem (400) according to Clause 12 further comprising: a second articulation input puck (404) engageable with a second articulation robotic output; a second articulation drive shaft (438) extending from the second articulation input puck (404) and comprising a second drive gear (436); and a proximal compound gear (442) engaged with the second drive gear (436) and the second rack gear (440), rotation of the second articulation input puck (404) rotates the second rack gear (440) moving the second rack (418A, 418B) with respect to the longitudinal axis (474).

Clause 14: The articulation subsystem (400) according to Clause 11, wherein the second rack gear (440) is a tube gear, and the second articulation drive shaft (438) is positioned within the second rack gear (440).

Clause 15: The articulation subsystem (400) according to any of Clauses 10 to 14, wherein the first rack (414) is positioned at least partially on a side of the first rack gear (434) opposite the rotatable shaft (604) and the second rack (418) is positioned at least partially on a side of the second rack gear (440) opposite the rotatable shaft (604).

Clause 16: The articulation subsystem (400) according to any of Clauses 8 to 12, wherein the first rack (414) is positioned at least partially between the first rack gear (434) and the rotatable shaft (604) and the second rack (418) is positioned at least partially between the second rack gear (440) and the rotatable shaft (604).

Clause 17: The articulation subsystem (400) according to any one of Clauses 1 to 16, wherein the articulation rod (406A, 406B, 407A, or 407B) is slidable through a rod groove (478) in the rotatable shaft (604).

Clause 18: An articulation subsystem (400) for a surgical instrument (100) comprising: a rotatable shaft (604) having a longitudinal axis (474); an articulation rod (406) extending along the longitudinal axis (474) of the rotatable shaft (604) and rotationally coupled to the rotatable shaft (604); a first articulation bushing (426) slidable from a first position to a second position along the longitudinal axis (474) of the rotatable shaft (604), the first articulation bushing (426) being rotationally coupled to the rotatable shaft (604); a first rack (414) movable with respect to the longitudinal axis (474) of the rotatable shaft (604), the first rack (414) being rotationally independent of the rotatable shaft (604) and the first articulation bushing (426); and a first rack gear (434) engaged with the first rack (414), wherein rotation of the first rack gear (434) moves the first rack (414) with respect to the longitudinal axis (474), and wherein movement of the first rack (414) with respect to the longitudinal axis (474) imparts an axial force onto the first articulation bushing (426) moving the first articulation bushing (426) from the first position to the second position.

Clause 19: The articulation subsystem according to Clause 18, wherein movement of the articulation bushing from the first position to the second position causes an end effector of the surgical instrument to pivot about an articulation pivot point.

Clause 20. The articulation subsystem according to Clause 18, wherein the rack gear is rotationally engaged with an articulation input puck, the articulation input puck being engageable with an articulation robotic output.

The invention is not necessarily limited to the examples described, which can be varied in construction and detail. The terms "distal" and "proximal" are used throughout the preceding description and are meant to refer to a positions and directions relative to a treating physician. As such, "distal" or distally" refer to a position distant to or a direction away from the physician. Similarly, "proximal" or "proximally" refer to a position near or a direction towards the physician. Furthermore, the singular forms "a," "an," and "the" include plural referents unless the context clearly dictates otherwise. Furthermore, the use of "couple", "coupled", or similar phrases should not be construed as being limited to a certain number of components or a particular order of components unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

In describing example embodiments, terminology has been resorted to for the sake of clarity. As a result, not all possible combinations have been listed, and such variants are often apparent to those of skill in the art and are intended to be within the scope of the claims which follow. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology.

What is claimed is:

1. An articulation subsystem for a surgical instrument comprising:

a rotatable shaft having a longitudinal axis;

a distal channel retainer coupled to an end effector, the distal channel retainer being pivotable about an articulation pivot point;

an articulation bushing slidable between a proximal position and a distal position along the longitudinal axis of the rotatable shaft;

an articulation rod extending distally from the articulation bushing and coupled at a distal end to the distal channel retainer;

a rack movable with respect to the longitudinal axis of the rotatable shaft; and a rack gear engaged with the rack, rotation of the rack gear moving the rack with respect to the longitudinal axis, wherein the rack is positioned at least partially between the rack gear and the rotatable shaft, wherein movement of the rack with respect to the longitudinal axis imparts an axial force onto the articulation bushing moving the articulation bushing between the proximal position and the distal position, and wherein movement of the articulation bushing between the distal position and the proximal position actuates the articulation rod causing the distal channel retainer to pivot about the articulation pivot point.

2. The articulation subsystem according to claim 1, wherein the articulation bushing is rotationally independent of the rack.

3. The articulation subsystem according to claim 1 further comprising:

a an articulation input puck engageable with an articulation robotic output;

an articulation drive shaft extending from the articulation input puck and comprising a drive gear; and a compound gear engaged with the drive gear and the rack gear, wherein rotation of the articulation input puck rotates the rack gear, moving the rack with respect to the longitudinal axis.

4. The articulation subsystem according to claim 3, wherein the rack gear is a tube gear, and the articulation drive shaft is positioned within the rack gear.

5. The articulation subsystem according to claim 3, wherein the rack gear is a first rack gear, the articulation subsystem further comprising:

a second rack gear engaged with the rack, rotation of the first rack gear and the second rack gear together moving the rack with respect to the longitudinal axis.

6. The articulation subsystem according to claim 5, wherein the first rack gear and the second rack gear simultaneously rotate in opposite directions to cause the rack to move with respect to the longitudinal axis.

7. The articulation subsystem according to claim 5, wherein the rack is positioned at least partially between the second rack gear and the rotatable shaft.

8. The articulation subsystem according to claim 5, wherein the articulation bushing is a first articulation bushing, the rack is a first rack, and the articulation rod is a first articulation rod, the articulation subsystem further comprising:

a second articulation bushing slidable between a second proximal position and a second distal position along the longitudinal axis of the rotatable shaft; and a second rack movable with respect to the longitudinal axis of the rotatable shaft, wherein movement of the second rack with respect to the longitudinal axis imparts an axial force onto the second articulation bushing to move the second articulation bushing between the second proximal position and the second distal position, wherein movement of the second articulation bushing between the second distal position and the second proximal position actuates a second articulation rod causing the distal channel retainer to pivot about the articulation pivot point.

9. The articulation subsystem according to claim 8, wherein movement of the first articulation bushing from the distal position to the proximal position actuates the distal channel retainer in a first direction, and wherein movement of the second articulation bushing from the second distal position to the second proximal position actuates the distal channel retainer in a second direction.

10. The articulation subsystem according to claim 8, the articulation subsystem further comprising a second rack gear engaged with the second rack, rotation of the second rack gear moving the second rack with respect to the longitudinal axis.

11. The articulation subsystem according to claim 10 further comprising:

a second articulation input puck engageable with a second articulation robotic output;

a second articulation drive shaft extending from the second articulation input puck and comprising a second drive gear; and a proximal compound gear engaged with the second drive gear and the second rack gear, rotation of the second articulation input puck rotates the second rack gear moving the second rack with respect to the longitudinal axis.

12. The articulation subsystem according to claim 11, wherein the first rack is positioned at least partially on a side of the first rack gear opposite the rotatable shaft and the second rack is positioned at least partially on a side of the second rack gear opposite the rotatable shaft.

13. The articulation subsystem according to claim 11, wherein the second rack gear is a tube gear, and the second articulation drive shaft is positioned within the second rack gear.

14. The articulation subsystem according to claim 8, wherein the second rack is positioned at least partially between the second rack gear and the rotatable shaft.

15. The articulation subsystem according to claim 1, wherein the articulation rod is slidable through a rod groove in the rotatable shaft.

16. The articulation subsystem according to claim 1, wherein the rack gear is a first rack gear, the articulation subsystem further comprising:

a second rack gear engaged with the rack, rotation of the first rack gear and the second rack gear together moving the rack with respect to the longitudinal axis, wherein the first rack gear and the second rack gear simultaneously rotate in opposite directions to cause the rack to move with respect to the longitudinal axis, and wherein rack is positioned at least partially between the second rack gear and the rotatable shaft.

17. An articulation subsystem for a surgical instrument comprising:

a rotatable shaft having a longitudinal axis;

an articulation rod extending along the rotatable shaft and rotationally coupled to the rotatable shaft;

an articulation bushing slidable from a first position to a second position along the longitudinal axis of the rotatable shaft, the articulation bushing being rotationally coupled to the rotatable shaft;

a first rack movable with respect to the longitudinal axis of the rotatable shaft, the first rack being rotationally independent of the rotatable shaft and the articulation bushing;

a second rack movable with respect to the longitudinal axis of the rotatable shaft, the second rack being rotationally independent of the rotatable shaft and the articulation bushing; and a rack gear engaged with at least one of the first rack or the second rack, wherein the first rack or the second rack is positioned at least partially between the rack gear and the rotatable shaft, wherein rotation of the rack gear moves the first rack with respect to the longitudinal axis, and wherein movement of the first rack with respect to the longitudinal axis imparts an axial force onto the articulation bushing moving the articulation bushing from the first position to the second position.

18. The articulation subsystem according to claim 17, wherein movement of the articulation bushing from the first position to the second position causes an end effector of the surgical instrument to pivot about an articulation pivot point.

19. The articulation subsystem according to claim 17, wherein the rack gear is rotationally engaged with an articulation input puck, the articulation input puck being engageable with an articulation robotic output.

20. The articulation subsystem according to claim 17, wherein the first rack and the second rack are integral.

21. A system for a surgical instrument comprising:

a rotatable shaft having a longitudinal axis;

a rack movable with respect to the longitudinal axis of the rotatable shaft, the rack being rotationally independent of the rotatable shaft;

an articulation bushing slidable from a first position to a second position along the longitudinal axis of the rotatable shaft, the articulation bushing being rotationally coupled to the rotatable shaft; and a rack gear engaged with the rack, and wherein the rack is positioned at least partially between the rack gear and the rotatable shaft, wherein rotation of the rack gear moves the rack with respect to the longitudinal axis, and wherein movement of the rack with respect to the longitudinal axis imparts an axial force onto the articulation bushing moving the articulation bushing from the first position to the second position.

22. The system according to claim 21 further comprising:

an end effector; and an articulation rod extending distally from the articulation bushing, wherein movement of the articulation bushing from the first position to the second position causes the end effector to pivot at a first angle relative to the longitudinal axis.

23. The system according to claim 22, wherein movement of the articulation bushing from the first position to the second position causes the end effector to pivot at an articulation pivot point.

24. The system according to claim 23, wherein the rack gear is a first rack gear, the system further comprising:

a second rack gear engaged with the rack, rotation of the first rack gear and the second rack gear together moving the rack with respect to the longitudinal axis.

25. The system according to claim 24, wherein the first rack gear and the second rack gear are configured to simultaneously rotate in opposite directions to cause the rack to move with respect to the longitudinal axis.

26. The system according to claim 25, wherein the rack is positioned at least partially between the second rack gear and the rotatable shaft.

27. The system according to claim 26 further comprising:

a first bearing positioned proximate a distal end of the rack; and a second bearing positioned proximate a proximal end of the rack, wherein the first bearing and the second bearing enable the articulation bushing to rotate independent of the rack.

28. The system according to claim 27, wherein the first bearing is constrained distally by a flange of the articulation bushing, and the second bearing is constrained proximally by a locking ring engaged with the articulation bushing.

29. The system according to claim 21 further comprising:

a first bearing positioned proximate a distal end of the rack; and a second bearing positioned proximate a proximal end of the rack, wherein the first bearing and the second bearing enable the articulation bushing to rotate independent of the rack, and wherein the first bearing is constrained distally by a flange of the articulation bushing, and the second bearing is constrained proximally by a locking ring engaged with the articulation bushing.

* * * * *